(12) United States Patent
Bannen et al.

(10) Patent No.: US 10,641,778 B2
(45) Date of Patent: May 5, 2020

(54) SYSTEM AND METHOD FOR ANALYSIS OF PEPTIDE SYNTHESIS FIDELITY

(71) Applicant: Roche Sequencing Solutions, Inc., Pleasanton, CA (US)

(72) Inventors: Ryan Bannen, Madison, WI (US); Sarah Barilovits, Madison, WI (US); Jigar Patel, Verona, WI (US); Eric Sullivan, Madison, WI (US); John Tan, Madison, WI (US)

(73) Assignee: ROCHE SEQUENCING SOLUTIONS, INC., Madison, WI (US)

( * ) Notice: Subject to any disclaimer, the term of this patent is extended or adjusted under 35 U.S.C. 154(b) by 426 days.

(21) Appl. No.: 15/233,543

(22) Filed: Aug. 10, 2016

(65) Prior Publication Data

US 2017/0059578 A1    Mar. 2, 2017

Related U.S. Application Data

(60) Provisional application No. 62/209,766, filed on Aug. 25, 2015.

(51) Int. Cl.
| | | |
|---|---|---|
| *G01N 33/68* | (2006.01) | |
| *B01J 19/00* | (2006.01) | |
| *G01N 21/64* | (2006.01) | |
| *C40B 40/10* | (2006.01) | |

(52) U.S. Cl.
CPC .......... *G01N 33/6845* (2013.01); *B01J 19/00* (2013.01); *B01J 19/0046* (2013.01); *C40B 40/10* (2013.01); *G01N 21/6428* (2013.01); *G01N 21/6452* (2013.01); *B01J 2219/00623* (2013.01); *B01J 2219/00725* (2013.01)

(58) Field of Classification Search
None
See application file for complete search history.

(56) References Cited

U.S. PATENT DOCUMENTS

2015/0185216 A1 *   7/2015   Albert et al. ........ G01N 33/573
                                                      506/1

FOREIGN PATENT DOCUMENTS

| EP | 1645639 A2 | 4/2006 | |
|---|---|---|---|
| WO | 2004003233 A1 | 1/2004 | |
| WO | WO-2004003233 A1 * | 1/2004 | ............ B82Y 30/00 |
| WO | 2014145123 A2 | 9/2014 | |
| WO | 2015097077 A2 | 7/2015 | |

* cited by examiner

*Primary Examiner* — Kaijiang Zhang
(74) *Attorney, Agent, or Firm* — Foley & Lardner LLP

(57) ABSTRACT

The present invention provides a system and method for assessing the fidelity of a synthetic peptide population including interrogating a population of peptide features in the presence of a receptor having an affinity for a plurality of binder sequences. A first amino acid is at a defined position within a first one of the binder sequences, and the population of peptide features includes a first control peptide feature synthesized to have an amino acid sequence including the first one of the binder sequences. The system and method further includes detecting a signal output characteristic of an interaction of the receptor with the first control peptide feature. The signal output is indicative of the fidelity of incorporation of the first amino acid into the first control peptide at the defined position within the first one of the binder sequences.

19 Claims, 44 Drawing Sheets

Specification includes a Sequence Listing.

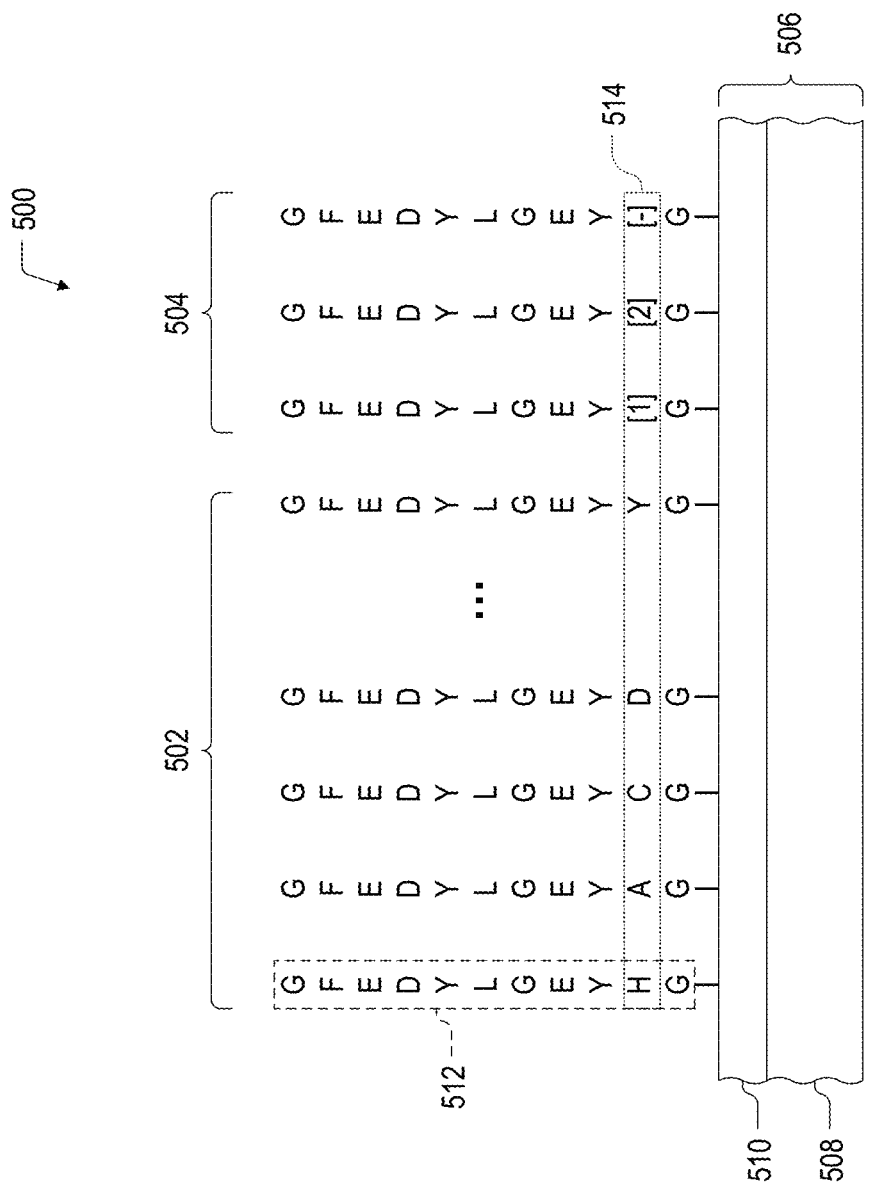

SYSTEM AND METHOD FOR ANALYSIS OF PEPTIDE SYNTHESIS FIDELITY

CROSS-REFERENCE TO RELATED APPLICATIONS

This application is based on, claims the benefit of, and incorporates herein by reference, U.S. Provisional Application Ser. No. 62/209,766, filed on 25 Aug. 2015 and entitled, "System and Method for Analysis of Peptide Synthesis Fidelity."

STATEMENT REGARDING FEDERALLY SPONSORED RESEARCH

Not applicable.

SEQUENCE LISTING

The instant application contains a Sequence Listing which has been submitted electronically in ASCII format and is hereby incorporated by reference in its entirety. Said ASCII copy, created on Jul. 14, 2017, is named 32946-US1_SL.txt and is 12,159 bytes in size.

BACKGROUND OF THE INVENTION

The disclosure relates, in general, to evaluating peptide synthesis and, more particularly, to a system and method for identifying and implementing quality control oligopeptide sequences for assaying peptide synthesis fidelity.

Peptides are biological polymers assembled, in part, through the formation of amide bonds between amino acid monomer units. In general, peptides may be distinguished from their protein counterparts based on factors such as size (e.g., number of monomer units or molecular weight), complexity (e.g., number of peptides, presence of coenzymes, cofactors, or other ligands), and the like. Experimental approaches for the identification of binding motifs, epitopes, mimotopes, disease markers, or the like may successfully employ peptides instead of larger or more complex proteins that may be more difficult to obtain or manipulate. As a result, the study of peptides and the capability to synthesize those peptides are of significant interest in the biological sciences and medicine.

Several methods exist for the synthesis of peptides including both in vivo and in vitro translation systems, as well as organic synthesis routes such as solid phase peptide synthesis. Solid phase peptide synthesis is a technique in which an initial amino acid is linked to a solid surface such as a bead, a microscope slide, or another like surface. Thereafter, subsequent amino acids are added in a step-wise manner to the initial amino acid to form a peptide chain. Because the peptide chain is attached to a solid surface, operations such as wash steps, side chain modifications, cyclization, or other treatment steps may be performed with the peptide chain maintained in a discrete location.

Recent advances in solid phase peptide synthesis have led to automated synthesis platforms for the parallel assembly of millions of unique peptide features in an array on a single surface (e.g., a ~75 mm×~25 mm microscope slide). The utility of such peptide arrays is, at least in part, dependent on the accuracy and fidelity with which the synthesis is carried out. For example, if the reagents used for synthesis are degraded, contaminated or improperly transported to the array surface during synthesis, a given peptide feature may have an altered, incomplete, or truncated peptide sequence. Other errors in peptide synthesis may also occur. However, it is generally impractical with currently available technologies to assay the quality of every individual feature on a routine basis due to both the number of features synthesized on a given array, and the associated material mass synthesized for each feature.

Accordingly, there is a need for improved processes and systems for the analysis of synthesis fidelity for peptide arrays as well as for peptide synthesis in general.

SUMMARY OF THE INVENTION

The present invention overcomes the aforementioned drawbacks by providing a system and method for analysis of peptide synthesis fidelity.

In accordance with one aspect of the present disclosure, a method of assessing the fidelity of a synthetic peptide population includes interrogating a population of peptide features in the presence of a receptor having an affinity for a plurality of binder sequences. A first amino acid is at a defined position within a first one of the binder sequences, and the population of peptide features includes a first control peptide feature synthesized to have an amino acid sequence including the first one of the binder sequences. The method further includes detecting a signal output characteristic of an interaction of the receptor with the first control peptide feature. The signal output is indicative of the fidelity of incorporation of the first amino acid into the first control peptide at the defined position within the first one of the binder sequences.

In one aspect, the method further includes detecting a signal output characteristic of an interaction of the receptor with a second control peptide feature. The signal output is indicative of the fidelity of incorporation of a second amino acid into the second control peptide at a defined position within a second one of the binder sequences. The first amino acid is different from the second amino acid, and the first one of the binder sequences is different from the second one of the binder sequences.

In another aspect, the signal output is further indicative of the fidelity of incorporation of a second amino acid into the first control peptide at a defined position within the first one of the binder sequences different from that of the first amino acid within the first one of the binder sequences, where the first amino acid is different from the second amino acid.

In yet another aspect, the first amino acid is selected from D-amino acids and L-amino acids.

In a further aspect, the receptor is streptavidin.

In still another aspect, the method further includes contacting the population of peptide features in the presence of the receptor with a fluorescent probe capable of binding to the receptor. The signal output is a fluorescence intensity obtained through fluorophore excitation-emission, the fluorescence intensity reflecting at least one of an abundance of a portion of the receptor associated with the first control peptide and a binding affinity of the receptor to the first control peptide.

In one aspect, the population of peptide features is covalently bound to a solid surface in an array. In some embodiments, the peptide features are bound to the solid surface at a density of at least about 100,000 features per square centimeter.

In another aspect, the population of peptide features includes less than twenty unique control peptide features. Each of the unique control peptide features are synthesized to have an amino acid sequence including a selected one of the binder sequences. In some embodiments, the signal output is further characteristic of an interaction of the receptor with the less than twenty control peptide features. The signal output is indicative of the fidelity of incorporation of each of the twenty natural amino acids into a selected one of the less than twenty unique control peptides at defined positions within the selected one of the binder sequences.

In yet another aspect, the output signal of the receptor is known for each of the plurality of binder sequences.

In still another aspect, the signal output is indicative of the presence of a contaminant in at least one of the amino acid synthesis reagents. In one example, the contaminant is acetic acid.

In accordance with another aspect of the present disclosure, a method of assessing the fidelity of a synthetic peptide population includes synthesizing a population of peptide features on a solid surface. The population of peptide features includes a plurality of sample peptide features and a plurality of control peptide features. The control peptide features include a first control peptide synthesized to have an amino acid sequence including a first one of a plurality of binder sequences having a first amino acid at a defined position within the first one of the binder sequences, and a second control peptide synthesized to have an amino acid sequence including a second one of the plurality of binder sequences having a second amino acid at a defined position within the second one of the binder sequences. The method further includes contacting the population of peptide features on the solid surface with a receptor having an affinity for the plurality of binder sequences, and detecting an output characteristic of an interaction of the receptor with each of the first control peptide feature and the second control peptide feature. The output is indicative of the fidelity of incorporation of the first amino acid into the first control peptide at the defined position within the first one of the binder sequences, and the second amino acid into the second control peptide at the defined position within the second one of the binder sequences.

In one aspect, each of the first amino acid and the second amino acid is selected from D-amino acids and L-amino acids.

In another aspect, the receptor is streptavidin.

In yet another aspect, the method further includes contacting the population of peptide features in the presence of the receptor with a fluorescent probe capable of binding to the receptor. The signal output is a fluorescence intensity obtained through fluorophore excitation-emission, the fluorescence intensity reflecting at least one of an abundance of a portion of the receptor associated with the first control peptide and a binding affinity of the receptor to the first control peptide.

In a further aspect, each of the sample peptide features has a defined sequence. In some embodiments the peptide features are bound to the solid surface at a density of at least about 100,000 features per square centimeter.

In still another aspect, the population of peptide features includes less than twenty unique control peptide features. Each of the unique control peptide features are synthesized to have an amino acid sequence including a selected one of the binder sequences. In some embodiments, the signal output is further characteristic of an interaction of the receptor with the less than twenty control peptide features. The signal output is indicative of the fidelity of incorporation of each of the twenty natural amino acids into a selected one of the less than twenty unique control peptides at defined positions within the selected one of the binder sequences.

In one aspect, the output signal of the receptor is known for each of the plurality of binder sequences.

In another aspect, the population of peptide features is prepared using maskless array synthesis.

In yet another aspect, the signal output is indicative of the presence of a contaminant in at least one of the amino acid synthesis reagents. In one example, the contaminant is acetic acid.

In accordance with a yet another aspect of the present disclosure, a synthetic peptide array includes an array substrate including a solid support having a reactive surface, and a population of peptide features immobilized on the reactive surface. The population of peptide features includes a plurality of control peptide features synthesized to have an amino acid sequence including a selected one of a plurality of binder sequences. Each of the binder sequences has a selected amino acid at a defined position within a corresponding one of the binder sequences. Detecting a signal output characteristic of an interaction of a receptor with each of the control peptide features is indicative of the fidelity of incorporation of the selected amino acid at the defined position within the corresponding one of the binder sequences.

In one aspect, the number of unique control peptide sequences is less than twenty.

In another aspect, the selected amino acid is one of the twenty canonical amino acids, and the interaction of the receptor with each of the control peptide features is indicative of the fidelity of incorporation of each of the twenty canonical amino acids.

In accordance with a further aspect of the present disclosure, a method of identifying a plurality of control peptides for assessing the fidelity of a synthetic peptide population includes identifying a plurality of peptide binder sequences capable of detectably interacting with a receptor having an affinity for the peptide binder sequence. Each of the peptide binder sequences includes at least about five amino acids. The method further includes profiling each of the identified plurality of peptide binder sequences to identify at least one detectable and distinguishable change in the interaction of the receptor molecules with the peptide features for at least one of a substitution and a deletion, and selecting at least a portion of the peptide binder sequences. The interrogation of the portion of the peptide binder sequences assesses the fidelity of incorporation of each of the twenty canonical amino acids in the synthetic peptide population.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5 is a schematic illustration of an embodiment of a peptide array (SEQ ID NOS 1, 50, 51, 52, 53, 54, 54, and 54, respectively, in order of appearance) for the identification and characterization of control peptides.

Like numbers will be used to describe like parts from Figure to Figure throughout the following detailed description.

DETAILED DESCRIPTION OF THE INVENTION

I. Overview

Figure 1:
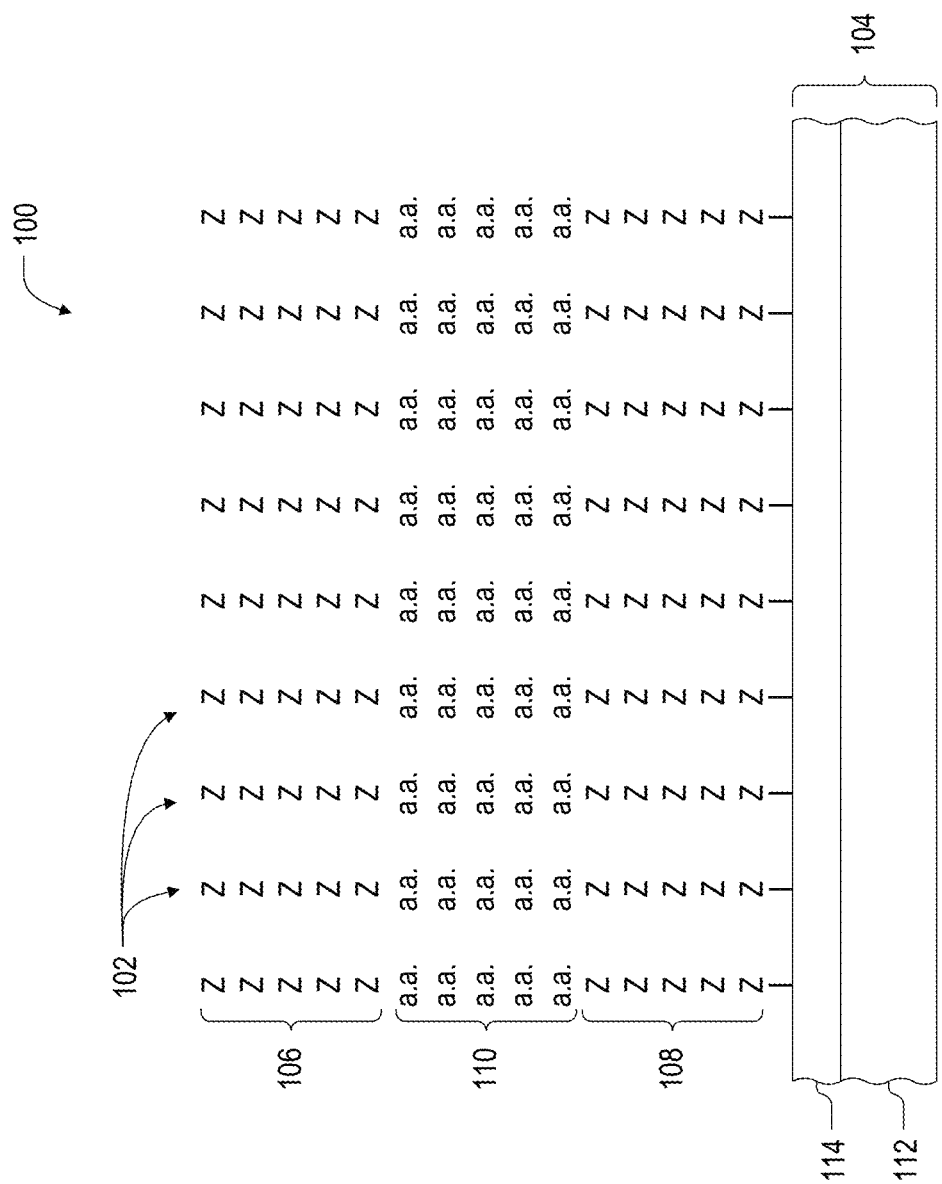
FIG. 1 is a schematic illustration of a peptide array for peptide binder discovery.

As also discussed above, in various situations it may be useful to provide quality control measures for assessing the fidelity of a plurality of synthetic peptides. In one example, it may be useful to check for successful incorporation of each type of amino acid or other monomer unit used in the synthesis of one or more peptide features in a solid phase peptide synthesis operation. In another example, it may be useful to monitor the quality of reagents used for solid phase peptide synthesis along with any associated process equipment for delivery of the reagents. In yet another example, it may be useful to determine the overall quality of an array in a non-destructive manner, by analyzing only a small subset of peptides, the like, or combinations thereof. Accordingly, many peptide synthesis schemes include various quality control sequences or analysis schemes to check for synthesis fidelity.

In one aspect, current quality control measures may pose several problems. For example, U.S. Pat. No. 6,955,915 to Fodor et al. describes a quality control method in which an initial binding profile may be measured for a fixed array design. Thereafter, binding profiles may be obtained for subsequent arrays of the same design for comparison with the initial binding profile. One challenge associated with this approach is that a new binding profile may need to be prepared for each unique array design. Further, a change in binding profiles between samples may not be informative as to the cause of the change. In an alternative example, a control peptide feature having a known sequence that is strongly bound by a detectable receptor may be synthesized at different spatial locations or beginning at different synthesis cycles as described for oligonucleotides in U.S. Pat. No. 7,569,343 to Marton et al. However, as discussed in the previous example, this method may only indicate the general occurrence of an error, or in some limited cases (e.g., vertical tiling in oligonucleotide arrays), the occurrence of an error during a particular synthesis cycle. Ultimately, the aforementioned quality control methods do not enable a determination of the particular cause of a synthesis error. Further challenges may arise depending on the number of peptide features, the category of the solid surface (e.g., beads vs. arrays) upon which the synthesis is performed, the size or complexity of the synthesized peptide features, and the like.

These and other challenges may be overcome with a system and method for assessing peptide synthesis fidelity according to the present disclosure. In one example, a system and method according to the present disclosure leverages measuring a signal output characteristic of an interaction of a receptor with a particular peptide sequence to detect an absolute or relative receptor affinity. The detected signal output can then be used to determine synthesis fidelity for a set of control peptides, and by extension, a broader population of peptides that includes the control peptides. In some embodiments, the control peptide sequences are selected to individually monitor successful incorporation of each of the twenty canonical amino acids. For example, a plurality of control peptides may be designed where each control peptide includes a unique binder sequence incorporating a selected one (or more) of the twenty canonical amino acids at a particular position (or positions) within the binder sequence. Accordingly, a substitution, deletion, or other synthesis error that affects a selected amino acid at the particular position will result in a measurable change in binding of the control peptide by a receptor having an affinity for the unique binder sequence.

In other embodiments, the control peptide sequences are selected to individually monitor the status of synthesis reagents, which can include solutions comprising one or more of the twenty canonical amino acids. In this example, a substitution, deletion, or other synthesis error caused by a degraded or otherwise compromised synthesis reagent that affects a selected amino acid at a particular position within a control peptide will result in a measurable change in binding of the control peptide by a receptor having an affinity for the unique binder sequence. Accordingly a measurement of synthesis fidelity can be indicative of both the quality of the synthesis reagents as well as the occurrence of synthesis errors (e.g., substitutions, deletions) during the various steps of the employed synthesis process.

In summary, according to one embodiment of the present disclosure, successful incorporation of an amino acid (e.g., glycine) into a population of peptides can be monitored by (i) characterizing a binder sequence-receptor pair where modification of the amino acid in the binder sequence results in a measurable change for a characteristic of an interaction (e.g., binding) of the receptor with the binder sequence, (ii) including in the population of peptides to be synthesized a control peptide having the characterized binder sequence, and (iii) detecting the characteristic of the interaction following synthesis of the population of peptides to determine whether the amino acid was successfully incorporated into the control peptide, and by extension, the population of peptides in general. Further a set of twenty or fewer unique control peptides can be designed to individually monitor successful incorporation of each of the twenty canonical amino acids following synthesis of a population of peptides including the control peptides.

In one aspect, the present disclosure provides a method of assessing the fidelity of a synthetic peptide population. For the purposes of the present disclosure, a synthetic peptide population includes any set of two or more peptides or peptide features (i.e., a grouping of two or more peptides having the same monomer sequence) prepared in a step-by-step chemical synthesis operation. For example, a synthetic peptide population may be prepared by solid phase peptide synthesis, where an initial amino acid is covalently bound to a solid surface either directly or via one or more linker molecules. Thereafter, subsequent amino acids may be added to the initial amino acid in directed or random fashion in order to prepare a population of peptide features arranged on a single surface such as a microscope slide, or distributed across a plurality of beads or other particle supports. One particular method for preparation of a population of synthetic peptides includes maskless array synthesis (MAS) technology (see, e.g., U.S. Pat. No. 8,658,572 to Albert et al.). However, other solid phase peptide synthesis methods, which are well known in the art, may be used for the formation of a synthetic peptide population according to the present disclosure.

For assessment of the synthetic peptide population, a method may include a first step of interrogating a population of peptide features in the presence of a receptor having an affinity for a plurality of binder sequences. A receptor includes any peptide, protein, antibody, small molecule, or other like structure that is capable of specifically binding a given peptide sequence or feature. In general, an aspect of the receptor should be detectable in order to determine whether the receptor is bound to a particular peptide or peptide feature. For example, the receptor itself may include a fluorophore that is detectable with a fluorescence microscope. Alternatively (or in addition), the receptor may be bound by a secondary molecule such as a fluorescent antibody. Further approaches will also fall within the scope of the present disclosure.

As described above the receptor is capable of binding to or otherwise interacting with a known binder sequence or affinity sequence. One example of a binder sequence is a defined amino acid sequence or motif. The defined amino acid sequence can represent at least a portion of a full length peptide within the synthetic peptide population. However, the binder sequence can itself be a full length peptide. For example, the eight amino acid peptide sequence Trp-Ser-His-Pro-Gln-Phe-Glu-Lys (SEQ ID NO:18) known as a "Strep-tag" exhibits intrinsic affinity towards an engineered form of the protein streptavidin. According to the present disclosure, a Strep-tag can be incorporated at either the N-terminus or the C-terminus of a given peptide or even incorporated at an intermediate point within a peptide. Thereafter, the peptide population including the peptides consisting of (or comprising) the Strep-tag binder sequence can be bound by the streptavidin receptor. Binding of streptavidin to the Strep-tag sequence can then be detected using various techniques. Further examples of binder sequences include the hexahistidine-tag (His-tag) (SEQ ID NO: 21), FLAG-tag, calmodulin-binding peptide, covalent yet dissociable peptide, heavy chain of protein C tag, and the like. Alternative (or additional) binder sequence-receptor pairs will also fall within the scope of the present disclosure.

With continued reference to binder sequences as disclosed herein, each binder sequence will have a particular or defined amino acid sequence. A binder sequence can include at least three amino acids. Example binder sequences disclosed here include between about five amino acids and about twelve amino acids. However, binder sequences having less than five or more than twelve amino acids can also be used. The positions of each amino acid in a particular binder sequence can be defined starting at either the N-terminus ([N]) or C-terminus ([C]). For example, the positions of the amino acids in the aforementioned Strep-tag binder sequence can be defined as [N]-Trp-Ser-His-Pro-Gln-Phe-Glu-Lys-[C] (SEQ ID NO:18). Accordingly, the position of the amino acid Histidine (His) is defined as the third amino acid from the N-terminus of the Strep-tag binder sequence. Notably, and as described above, the Strep-tag binder sequence can be flanked by one or more additional amino acids at either or both of the N-terminus and the C-terminus.

A population of peptide features as disclosed herein can further include one or more control peptides or features comprising multiple control peptides. A variety of control peptides having various functions or purposes can be included in a particular population of peptide features. However, at least a portion of these control peptides can be synthesized to have an amino acid sequence including a binder sequence. In one example, a control peptide amino acid sequence consists of the binder sequence. In another example, a control peptide amino acid sequence includes the binder sequence flanked by one or more additional amino acids at either or both of the N-terminus and the C-terminus. Control peptide features that are correctly synthesized and therefore include a binder sequence can be bound by a receptor having an affinity for the included binder sequence. On the other hand, control peptide features that are incorrectly synthesized may be bound with an altered affinity (or not bound at all) by the receptor. In the example case of the Strep-tag, a substitution or deletion including a selected one of the amino acids in the binder sequence (e.g., the amino acid His at the third position from the N-terminus of the Strep-tag binder sequence) may partially or completely disrupt the ability of the corresponding streptavidin receptor to bind the incorrectly synthesized control peptide that includes the Strep-tag binder sequence.

A method according to the present disclosure further includes detecting a signal output characteristic of an interaction of the receptor with the first control peptide feature. A step of detecting a signal output can include any manner of monitoring or otherwise observing a measurable aspect of one or more peptides or peptide features within a population of peptides in the presence or absence of a receptor. Example signal outputs include an optical output (e.g., luminescence), an electrical output, a chemical output, the like, and combinations thereof. As a result, the step of detecting the signal output can include measuring, recording, or otherwise observing the signal output using any suitable instrument. Example instruments include optical and digital detection instruments such as fluorescence microscopes, digital cameras, or the like. In some embodiments, detecting a signal output further includes a perturbation such as excitation with light at one or more wavelengths, thermal manipulation, introduction of one or more chemical reagents, the like, and combinations thereof.

In some embodiments of the present system and method, the detected signal output is characteristic of an interaction of the receptor with a control peptide feature. As discussed above, depending on the actual sequence of the control peptide synthesized to incorporate the binder sequence, the receptor may have a variable interaction with the control peptide. For an example receptor-binder sequence pair, the receptor exhibits a strong affinity for a control peptide having the correct binder sequence; however, for a different control peptide having the binder sequence but possessing a synthesis error (e.g., an amino acid substitution or deletion within the binder sequence), the receptor exhibits a relatively weaker affinity for the flawed control peptide. The affinity (or interaction) of the receptor for each of the correct and flawed control peptides may be detected as a signal output characteristic of the interaction. Therefore, a corresponding signal output can be indicative of the fidelity of incorporation of a particular amino acid into a control peptide at a defined position within a binder sequence.

Returning again to the Strep-tag example, two distinct control peptides are synthesized to have the Strep-tag binder sequence. One of the control peptides (control peptide A) is accurately synthesized and possesses the full length Strep-tag binder sequence. The other of the control peptides (control peptide B) is synthesized incorrectly and as a result includes a deletion of the amino acid His at the third position from the N-terminus within the Strep-tag binder sequence. In the case that the His in question contributes the affinity of the streptavidin receptor to the Strep-tag binder sequence, the streptavidin receptor will have a higher affinity for control peptide A as compared with control peptide B. As a result, incubating each of control peptide A and control peptide B with a fluorescently labelled streptavidin receptor leads to a relatively greater concentration of the labelled streptavidin receptor at the location of control peptide A and a relatively smaller concentration of the labelled streptavidin receptor at the location of control peptide B. The resulting differential fluorescent signal output from the locations of each of the control peptides is therefore characteristic of the interaction of the receptor with the control peptides. In particular, the signal output due to the streptavidin receptor affinity for the Strep-tag binder sequence is indicative of the fidelity of incorporation of the amino acid His into the control peptide A both in general and, more particularly, at the defined position (third amino acid from the N-terminus) within the Strep-tag binder sequence. If each of the control peptides synthesized to have the Strep-tag binder sequence are interrogated and found to bind the streptavidin receptor more weakly than would be expected, it can be inferred that the greater population of peptides comprising the control peptides may also include synthesis errors related to the quality or delivery of the amino acid His.

Notably, a synthetic peptide population can include a population of peptide features that is synthesized to include alternative building blocks such as non-natural amino acids, amino acid derivatives, or other monomer units altogether. In this case, one or more binder sequences can be prepared with each of the selected alternative building blocks. The binder sequences can then be used to interrogate the fidelity of incorporation of each of the alternative building blocks into a corresponding binder sequence. For example, it may be useful to synthesize a population of peptide features where at least some of the peptide features include the non-natural amino acid citrulline. In order to monitor whether citrulline was successfully incorporated into the population of peptide features, a binder sequence including at least one citrulline at a defined position within the binder sequence can be identified. The binder sequence can be included as a control peptide feature within the overall population of peptide features. Further variations and alternative methodologies for assessing the fidelity of a synthetic peptide population according to the present disclosure will become apparent from the following detailed description.

II. Peptides

According to various embodiments of the instant disclosure, peptides (e.g., control peptides, peptide binder sequences) are disclosed. Each of the peptides includes two or more natural or non-natural amino acids as described herein. In examples described herein, a linear form of peptide is shown. However, one of skill in the art would immediately appreciate that the peptides can be converted to a cyclic form, e.g., by reacting the N-terminus with the C-terminus as disclosed in the U.S. Pat. Pub. No. 2015/0185216 to Albert et al. and filed on Dec. 19, 2014. The embodiments of the invention therefore include both cyclic peptides and linear peptides.

As used herein, the terms "peptide," "oligopeptide," and "peptide binder" refer to organic compounds composed of amino acids, which may be arranged in either a linear chain (joined together by peptide bonds between the carboxyl and amino groups of adjacent amino acid residues), in a cyclic form (cyclized using an internal site) or in a constrained form (e.g., "macrocycle" of head-to-tail cyclized form). The terms "peptide" or "oligopeptide" also refer to shorter polypeptides, i.e., organic compounds composed of less than 50 amino acid residues. A macrocycle (or constrained peptide), as used herein, is used in its customary meaning for describing a cyclic small molecule such as a peptide of about 500 Daltons to about 2,000 Daltons.

The term "natural amino acid" or "canonical amino acid" refers to one of the twenty amino acids typically found in proteins and used for protein biosynthesis as well as other amino acids which can be incorporated into proteins during translation (including pyrrolysine and selenocysteine). The twenty natural amino acids include the L-stereoisomers of histidine (His; H), alanine (Ala; A), valine (Val; V), glycine (Gly; G), leucine (Leu; L), isoleucine (Ile; I), aspartic acid (Asp; D), glutamic acid (Glu; E), serine (Ser; S), glutamine (Gln; Q), asparagine (Asn; N), threonine (Thr; T), arginine (Arg; R), proline (Pro; P), phenylalanine (Phe; F), tyrosine (Tyr; Y), tryptophan (Trp; W), cysteine (Cys; C), methionine (Met; M), and lysine (Lys; K). The term "all twenty amino acids" refers to the twenty natural amino acids listed above.

The term "non-natural amino acid" refers to an organic compound that is not among those encoded by the standard genetic code, or incorporated into proteins during translation. Therefore, non-natural amino acids include amino acids or analogs of amino acids, but are not limited to, the D-stereoisomers of all twenty amino acids, the beta-amino-analogs of all twenty amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

According to embodiments of the instant disclosure, peptides are presented immobilized on a support surface (e.g., a microarray, a bead, or the like). In some embodiments, peptides selected for use as control peptides may optionally undergo one or more rounds of extension and maturation processes to yield the control peptides disclosed herein.

III. Microarrays

The control peptides disclosed herein can be generated using oligopeptide microarrays. As used herein, the term "microarray" refers to a two dimensional arrangement of features on the surface of a solid or semi-solid support. A single microarray or, in some cases, multiple microarrays (e.g., 3, 4, 5, or more microarrays) can be located on one solid support. For a solid support having fixed dimensions, the size of the microarrays depends on the number of microarrays on the solid support. That is, the higher the number of microarrays per solid support, the smaller the arrays have to be to fit on the solid support. The arrays can be designed in any shape, but preferably they are designed as squares or rectangles. The ready to use product is the oligopeptide microarray on the solid or semi-solid support (microarray slide).

The terms "peptide microarray" or "oligopeptide microarray," or "peptide chip," or "peptide epitope microarray" refer to a population or collection of peptides displayed on a microarray, i.e., a solid surface, for example a glass, carbon composite or plastic array, slide, or chip.

The term "feature" refers to a defined area on the surface of a microarray. The feature comprises biomolecules, such as peptides (i.e., a peptide feature), nucleic acids, carbohydrates, and the like. One feature can contain biomolecules with different properties, such as different sequences or orientations, as compared to other features. The size of a feature is determined by two factors: i) the number of features on an array, the higher the number of features on an array, the smaller is each single feature, ii) the number of individually addressable aluminum mirror elements which are used for the irradiation of one feature. The higher the number of mirror elements used for the irradiation of one feature, the bigger is each single feature. The number of features on an array may be limited by the number of mirror elements (pixels) present in the micromirror device. For example, the state of the art micromirror device from Texas Instruments, Inc. (Dallas, Tex.) currently contains 4.2 million mirror elements (pixels), thus the number of features within such exemplary microarray is therefore limited by this number. However, higher density arrays are possible with other micromirror devices.

The term "solid or semi-solid support" refers to any solid material, having a surface area to which organic molecules can be attached through bond formation or absorbed through electronic or static interactions such as covalent bonds or complex formation through a specific functional group. The support can be a combination of materials such as plastic on glass, carbon on glass, and the like. The functional surface can be simple organic molecules but can also comprise of co-polymers, dendrimers, molecular brushes, and the like.

The term "plastic" refers to synthetic materials, such as homo- or hetero-co-polymers of organic building blocks (monomer) with a functionalized surface such that organic molecules can be attached through covalent bond formation or absorbed through electronic or static interactions such as through bond formation through a functional group. Preferably the term "plastic" refers to polyolefin, which is a polymer derived by polymerization of an olefin (e.g., ethylene propylene diene monomer polymer, polyisobutylene). Most preferably, the plastic is a polyolefin with defined optical properties, like TOPAS® or ZEONOR/EX®.

The term "functional group" refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol, and nitril. Potentially reactive functional groups include, for example, amines, carboxylic acids, alcohols, double bonds, and the like. Preferred functional groups are potentially reactive functional groups of amino acids such as amino groups or carboxyl groups.

Various methods for the production of oligopeptide microarrays are known in the art. For example, spotting prefabricated peptides or in situ synthesis by spotting reagents (e.g., on membranes) exemplify known methods. Other known methods used for generating peptide arrays of higher density are the so-called photolithographic techniques, where the synthetic design of the desired biopolymers is controlled by suitable photolabile protecting groups (PLPG) releasing the linkage site for the respective next component (amino acid, oligonucleotide) upon exposure to electromagnetic radiation, such as light (Fodor et al., (1993) Nature 364:555-556; Fodor et al., (1991) Science 251:767-773). Two different photolithographic techniques are known in the state of the art. The first is a photolithographic mask, used to direct light to specific areas of the synthesis surface effecting localized deprotection of the PLPG. "Masked" methods include the synthesis of polymers utilizing a mount (e.g., a "mask") which engages a substrate and provides a reactor space between the substrate and the mount. Exemplary embodiments of such "masked" array synthesis are described in, for example, U.S. Pat. Nos. 5,143,854 ad 5,445,934, the disclosures of which are hereby incorporated by reference. Potential drawbacks of this technique, however, include the need for a large number of masking steps resulting in a relatively low overall yield and high costs, e.g., the synthesis of a peptide of only six amino acids in length could require over 100 masks. The second photolithographic technique is the so-called maskless photolithography, where light is directed to specific areas of the synthesis surface effecting localized deprotection of the PLPG by digital projection technologies, such as micromirror devices (Singh-Gasson et al., Nature Biotechn. 17 (1999) 974-978). Such "maskless" array synthesis thus eliminates the need for time-consuming and expensive production of exposure masks. It should be understood that the embodiments of the systems and methods disclosed herein may comprise or utilize any of the various array synthesis techniques described above.

The use of PLPG (photolabile protecting groups), providing the basis for the photolithography based synthesis of oligopeptide microarrays, is well known in the art. Commonly used PLPG for photolithography based biopolymer synthesis are for example α-methyl-6-nitropiperonyl-oxycarbonyl (MeNPOC) (Pease et al., Proc. Natl. Acad. Sci. USA (1994) 91:5022-5026), 2-(2-nitrophenyl)-propoxycarbonyl (NPPOC) (Hasan et al. (1997) Tetrahedron 53: 4247-4264), nitroveratryloxycarbonyl (NVOC) (Fodor et al. (1991) Science 251:767-773) and 2-nitrobenzyloxycarbonyl (NBOC).

Amino acids have been introduced in photolithographic solid-phase peptide synthesis of oligopeptide microarrays, which were protected with NPPOC as a photolabile amino protecting group, wherein glass slides were used as a support (U.S. App. Pub. No. 20050101763). The method using NPPOC protected amino acids has the disadvantage that the half-life upon irradiation with light of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing oligomers increases with increasing and excessive light dose requirement.

As understood by one of skill in the art, peptide microarrays comprise an assay principle whereby thousands (or in the case of the instant disclosure, millions) of peptides (in some embodiments presented in multiple copies) are linked or immobilized to the surface of a solid support (which in some embodiments comprises a glass, carbon composite or plastic chip or slide).

In some embodiments, a peptide microarray is exposed to a sample of interest such as a receptor, antibody, enzyme, peptide, oligonucleotide, or the like. The peptide microarray exposed to the sample of interest undergoes one or more washing steps, and then is subjected to a detection process. In some embodiments, the array is exposed to an antibody targeting the sample of interest (e.g. anti IgG human/mouse or anti-phosphotyrosine or anti-myc). Usually, the secondary antibody is tagged by a fluorescent label that can be detected by a fluorescence scanner. Other detection methods are chemiluminescence, colorimetry, or autoradiography. In other embodiments, the sample of interest is biotinylated, and then detected by streptavidin conjugated to a fluorophore. In yet other embodiments, the protein of interest is tagged with specific tags, such as His-tag, FLAG-tag, Myc-tag, etc., and detected with a fluorophore-conjugated antibody specific for the tag.

After scanning the microarray slides, the scanner records a 20-bit, 16-bit or 8-bit numeric image in tagged image file format (*.tif). The tif-image enables interpretation and quantification of each fluorescent spot on the scanned microarray slide. This quantitative data is the basis for performing statistical analysis on measured binding events or peptide modifications on the microarray slide. For evaluation and interpretation of detected signals an allocation of the peptide spot (visible in the image) and the corresponding peptide sequence has to be performed.

A peptide microarray is a slide with peptides spotted onto it or assembled directly on the surface by in situ synthesis. Peptides are ideally covalently linked through a chemoselective bond leading to peptides with the same orientation for interaction profiling. Alternative procedures include unspecific covalent binding and adhesive immobilization.

According one specific embodiment of the instant disclosure, the specific peptide binders are identified using maskless array synthesis in the fabrication of the peptide binder probes on the substrate. According to such embodiments, the maskless array synthesis employed allows ultra-high density peptide synthesis of up to 2.9 million unique peptides. Each of the 2.9 million features/regions having up to 107 reactive sites that could yield a full-length peptide. Smaller arrays can also be designed. For example, an array representing a comprehensive list of all possible 5-mer peptides using 19 natural amino acids excluding cysteine will have 2,476,099 peptides. In other examples, an array may include non-natural amino acids as well as natural amino acids. An array of 5-mer peptides by using all combinations of 18 natural amino acids excluding cysteine and methionine may also be used. Additionally, an array can exclude other amino acids or amino acid dimers. In some embodiments, an array may be designed to exclude any dimer or a longer repeat of the same amino acid, as well as any peptide containing HR, RH, HK, KH, RK, KR, HP, and PQ sequences to create a library of 1,360,732 unique peptides. Smaller arrays may have replicates of each peptide on the same array to increase the confidence of the conclusions drawn from array data.

In various embodiments, the peptide arrays described herein can have at least $1.6 \times 10^5$ peptides, or up to about $1.0 \times 10^8$ peptides or any number in-between, attached to the solid support of the peptide array. As described herein, a peptide array comprising a particular number of peptides can mean a single peptide array on a single solid support, or the peptides can be divided and attached to more than one solid support to obtain the number of peptides described herein.

Arrays synthesized in accordance with such embodiments can be designed for peptide binder discovery in the linear or cyclic form (as noted herein) and with and without modification such as N-methyl or other post-translational modifications. Arrays can also be designed for further extension of potential binders using a block-approach by performing iterative screens on the N-terminus and C-terminus of a potential hit (as is further described in detail herein). Once a hit of an ideal affinity has been discovered it can be further matured using a combination of maturation arrays (described further herein), that allow a combinatorial insertion, deletion and replacement analysis of various amino acids both natural and non-natural.

The peptide arrays of the instant disclosure are used to identify the specific binders or binder sequences of the invention as well as for maturation and extension of the binder sequences for use in the design and selection of control peptides.

IV. Peptide Binder Discovery

In one aspect, the present disclosure provides for the discovery of novel binders (e.g., control peptides, binder sequences, and the like). Turning now to FIG. 1, according to one embodiment of the instant disclosure, a peptide array 100 may be designed comprising a population of hundreds, thousands, tens of thousands, hundreds of thousands and even millions of peptides 102. In some embodiments, the population of peptides 102 can be configured such that the peptides 102 collectively represent an entire protein, gene, chromosome, or even an entire genome of interest (e.g., a human proteome). Additionally, the peptides 102 can be configured according to specific criteria, whereby specific amino acids or motifs are excluded. Furthermore, the peptides 102 can be configured such that each of the peptides 102 comprises an identical length. For example, in some embodiments the population of peptides 102 immobilized on an array substrate 104 may all comprise 3-, 4-, 5-, 6-, 7-, 8-, 9-, 10-, 11-, or even 12-mers, or more. In some embodiments, the peptides 102 can also each comprise an N-terminal sequence (N-term 106) or a C-terminal sequence (C-term 108), where each peptide 102 comprises both an N-terminal sequence and a C-terminal peptide sequence of a specific and identical length (e.g., 3-, 4-, 5-, 6-, 7- or even 8-mers or more). Notably, the sequences of the peptides at specific locations on the array are known.

According to some embodiments, a peptide array 100 is designed including a population of up to 2.9 million peptides 102, configured such that the 2.9 million peptides 102 represents a comprehensive list of all possible 5-mer probe peptides 110 of a genome, immobilized on the array substrate 104. In some such embodiments, the 5-mer probe peptides 110 (comprising the 2.9 million peptides of the array) may exclude one or more of the twenty amino acids. For example, Cys could be excluded in order to aid in controlling unusual folding of the peptide. The amino acid Met could be excluded as a rare amino acid within the proteome. Other optional exclusions are amino acid repeats of two or more of the same amino acid (in order to aide in controlling non-specific interactions such as charge and hydrophobic interactions); or particular amino acid motifs (e.g., in case of streptavidin binders), those consisting of His-Pro-Gln sequence, where His-Pro-Gln is a known streptavidin binding motif. With continued reference to FIG. 1, in some illustrative embodiments, the 5-mer probe peptides 110 may exclude one, or more than one of the amino acids or amino acid motifs listed above. One embodiment of the invention includes a peptide array 100 comprising a population of up to 2.9 million peptides 102, where the 5-mer probe peptides 110 portions of the peptides 102 represent the entire human genome. In one example, the 5-mer probe peptides 110 do not include the amino acids Cys and Met, do not include amino acid repeats of two or more amino acids, and do not include the amino acid motif His-Pro-Gln. Another embodiment of the invention includes a peptide array comprising up to 2.9 million peptides 102 including the 5-mer probe peptides 110, representing the protein content encoded by the entire human genome, wherein the 5-mer probe peptides 110 do not include the amino acids Cys and Met, and do not include amino acid repeats of two or more amino acids.

According to further embodiments, each 5-mer probe peptide 110 comprising the population of up to 2.9 million peptides 102 of the peptide array 100 may be synthesized with five cycles of wobble synthesis in each of the N-term 106 and the C-term 108 as shown in FIG. 1. As used herein "wobble synthesis" refers to synthesis (through any of the means disclosed herein) of a sequence of peptides (either constant or random) which are positioned at the N-terminus or C-terminus of the 5-mer probe peptides 110 of interest. As illustrated in FIG. 1, the specific amino acids comprising the wobble synthesis at either the N-term 106 or the C-term 108 are represented by a "Z." According to various embodiments, wobble synthesis may include any number of amino acids or other monomer units at the N-term 106 and the C-term 1-8. For example, each of the N-term 106 and the C-term 108 can include 1, 2, 3, 4, 5, 6, 7, 8, 9, 10, or more (e.g., 15-20) amino acids. Furthermore, wobble synthesis may comprise N-termini and C-termini having the same or differing number of wobble synthesized amino acids.

According to various embodiments, the wobble oligopeptide compositions of the N-term 106 and the C-term 108 are flexible in terms of amino acid composition and in terms of amino acid ratios or concentrations. For example, the wobble oligopeptide compositions may comprise a mixture of two or more amino acids. An illustrative embodiment of a flexible wobble mix includes a wobble oligopeptide composition of Gly and Ser at a ratio of 3:1 (Gly:Ser). Other examples of a flexible wobble mixture include equal concentrations (e.g., equal ratios) of amino acids Gly, Ser, Ala, Val, Asp, Pro, Glu, Leu, Thr, equal concentrations (e.g., equal ratios) of amino acids Leu, Ala, Asp, Lys, Thr, Gln Pro, Phe, Val, Tyr, and combinations thereof. Other examples include wobble oligopeptide compositions for the N-term 106 and the C-term 108 comprising any of the twenty canonical amino acids, in equal concentrations.

As disclosed herein, wobble oligopeptide synthesis of the various embodiments allows for generating a peptide on an array having a combination of random and directed synthesis amino acids. For example, an oligopeptide probe on an array may comprise a combined 15-mer peptide having a peptide sequence in the following format: ZZZZZ-[5-mer]-ZZZZZ, where Z is an amino-acid from a particular wobble amino acid mixture. In another aspect, ZZZZZ can be abbreviated as 5Z, whereas nZ corresponds to n consecutive amino acids selected from a set of amino acids comprising a wobble amino acid mixture.

In some embodiments, a feature may contain about $10^7$ peptides. In some such embodiments, the population complexity for each feature may vary depending on the complexity of the wobble mixture. As disclosed herein, creating such complexity using wobble synthesis in a semi-directed synthesis enables the screening of binders on the array, using peptides with diversity up to about $10^{12}$ unique sequences. Examples of binder screening for Streptavidin are set forth below. However, additional protein targets such as prostate specific antigen, urokinase, or tumor necrosis factor are also possible according to the methods and systems set forth.

It has further been discovered that linkers (e.g., N-term 106 and C-term 108) can vary in length and are optional. In some embodiments, instead of a 5Z linker, a 3Z or a 1Z linker can be used. In such embodiments, Z could be synthesized using a random mixture of all 20 amino acids. It has been discovered that the same target can yield additional 5-mer binder sequences when 1Z linker or no linker is used. It has been discovered that changing the length of or eliminating the linker results in identification of additional peptide binders that were not found using e.g., the original 5Z linker.

In practice, with reference to FIG. 1, a peptide array 100 includes an array substrate 104 comprising a solid support 112 having a reactive surface 114 (e.g., a reactive amine layer) with a population of peptides 102 (such as a population of 5-mers representing the entire human proteome) immobilized thereto. The exemplary 5-mer peptides comprising the population of peptides 102, according to such embodiment, does not include any of the amino acids Cys and Met, does not include amino acid repeats of two or more amino acids and does not include the amino acid motif His-Pro-Gln. According to embodiment illustrated in FIG. 1, the population of peptides 102 representing the entire human proteome would comprise 1,360,732 individual peptides comprising the population of peptides 102. In some embodiments, duplicates or repeats may be placed on the same array. For example, a population of peptides 102 comprising a single duplicate would comprise 2,721,464 individual features. Additionally, the peptides 102 each comprise an N-terminal and C-terminal wobble synthesis oligopeptide (i.e., N-term 106 and C-term 108). In one example, the N-term 106 and C-term 108 each have five amino acids, where each of the amino acids is randomly selected from a mixture of Gly and Ser in a 3:1 ratio (Gly:Ser). The wobble oligopeptides forming the N-term 106 and the C-term 108 can be omitted or replaced with a single amino acid selected from a random mixture of all twenty amino canonical acids, non-natural amino acids (e.g., 6-amino-hexanoic acid), or a combination thereof. Some embodiments can include non-amino acid moieties (e.g., polyethylene glycol).

Figure 2:
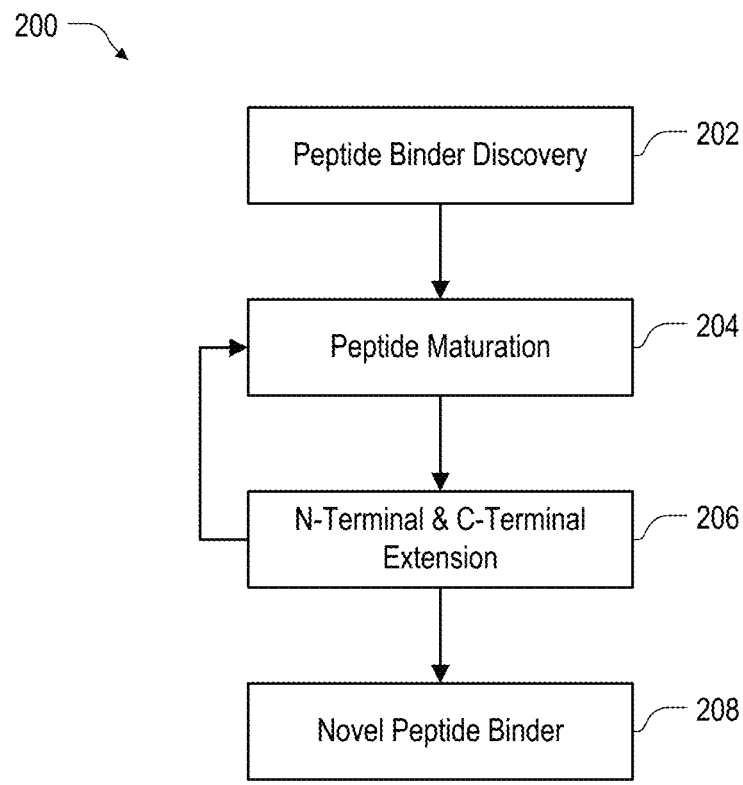
FIG. 2 is an example of a method for identifying peptide binders according to the present disclosure.

Referring generally now to FIG. 2, a process 200 for preparing a peptide array (e.g. peptide array 100 as shown in FIG. 1) includes a step 202 of peptide binder discovery. In one example of the step 202, a peptide array is exposed to a concentrated, purified protein of interest (as with standard microarray practice), whereby the protein of interest may bind or otherwise interact with one or more of the population of peptides (e.g. the population of peptides 102 as shown in FIG. 1). In one aspect, the protein of interest may bind a selected one of the population of peptides independent of another one of the population of peptides comprising the population. After exposure to the protein of interest, binding of the protein of interest to the peptide binders is assayed, for example, by way of exposing the array to an antibody (specific for the protein) which has a reportable label (e.g., peroxidase) attached thereto. Because the peptide sequence of each 5-mer at each location on the array is known, it is possible to chart, or quantify, or compare and contrast the sequences (and binding strengths) of the binding of the protein to specific 5-mer peptide sequences. One such method of comparing the protein binding to the peptides comprising the population is to review the binding in a principled analysis distribution-based clustering, such as described by White et al. (Standardizing and Simplifying Analysis of Peptide Library Data, Chem. Inf. Model., 2013, 53(2), pp 493-499), and illustrated herein. As is exemplified herein, the clustering of protein-5-mer binding (a.k.a., "hits"; shown in a principled analysis distribution-based clustering) indicates 5-mers having overlapping peptide sequences. As demonstrated in greater detail below, from the overlapping peptide sequences (of each cluster), a "core hit" peptide sequence (e.g., a peptide sequence shared by the prominent protein-peptide binding events of the array) can be identified, or at least hypothesized and constructed for further evaluation. In one aspect, an array as exemplified herein may identify more than one core hit peptide sequence. Further, it is possible for the core hit peptide sequence to comprise more amino acids than, for example, the 5-mer peptide binders comprising the population of peptides due to possible identification of overlapping and adjacent sequences during principled analysis distribution-based clustering.

V. Peptide Maturation

With continued reference to FIG. 2, upon identification of a core hit peptide sequence (through the process of peptide binder discovery 202 disclosed, described and exemplified herein), a step 204 of the process 200 includes peptide maturation whereby the core hit peptide sequence is modified in various ways (through amino acid substitutions, deletions and insertions) at each position of the core hit peptide in order to further optimize or verify the proper core hit sequence. For example, according to some embodiments (e.g., where the core hit peptide sequence comprises a given number of amino acids), a maturation array is produced. According to the instant disclosure, the maturation array may have, immobilized thereto, a population of core hit peptides whereby each amino acid in the core hit peptide has undergone an amino acid substitution at each position.

In order to further describe the process of hit maturation or peptide maturation 204, an example or hypothetical core hit peptide is described as consisting of a 5-mer peptide having the amino acid sequence -$M_1M_2M_3M_4M_5$- (SEQ ID NO: 22). According to the instant disclosure, hit maturation 204 may involve any of, or a combination of any or all of, amino acid substitutions, deletions, and insertions at positions 1, 2, 3, 4, and 5. For example, in regard to the hypothetical core hit peptide -$M_1M_2M_3M_4M_5$- (SEQ ID NO: 22), embodiments of the instant disclosure may include the amino acid M at position 1 being substituted with each of the other 19 amino acids (e.g., $A_1M_2M_3M_4M_5$- (SEQ ID NO: 23), $P_1M_2M_3M_4M_5$- (SEQ ID NO: 24), $V_1M_2M_3M_4M_5$- (SEQ ID NO: 25), $Q_1M_2M_3M_4M_5$- (SEQ ID NO: 26), etc.). Each position (2, 3, 4, and 5) would also have the amino acid M substituted with each of the other 19 amino acids (for example, with position 2 the substitutions would resemble, $M_1A_2M_3M_4M_5$- (SEQ ID NO: 27). $M_1Q_2M_3M_4M_5$- (SEQ ID NO: 28), $M_1P_2M_3M_4M_5$- (SEQ ID NO: 29), $M_1N_2M_3M_4M_5$- (SEQ ID NO: 30), etc.). It should be understood that a peptide (immobilized on an array) is created comprising a core hit peptide including one or more substitutions, deletions, insertions, or a combination thereof.

In some embodiments of the process 200, the step 204 of peptide maturation includes the preparation of a double amino acid substitution library. A double amino acid substitution includes altering the amino acid at a first position in combination with substitution of an amino acid at a second position with each of the other nineteen amino acids. This process is repeated until all possible combinations of the first and second positions are combined. By way of example, referring back to the hypothetical core hit peptide having a 5-mer peptide with amino acid sequence -$M_1M_2M_3M_4M_5$- (SEQ ID NO: 22), a double amino acid substitution with regard to positions 1 and 2 may include, for example, an M→P substitution at position 1, and then a substitution of all 20 amino acids at position 2 (e.g., -$P_1A_2M_3M_4M_5$- (SEQ ID NO: 31), -$P_1F_2M_3M_4M_5$- (SEQ ID NO: 32), -$P_1V_2M_3M_4M_5$- (SEQ ID NO: 33), -$P_1E_2M_3M_4M_5$- (SEQ ID NO: 34), etc.), an M→V substitution at position 1, and then a substitution of all 20 amino acids at position 2 (e.g., -$V_1A_2M_3M_4M_5$- (SEQ ID NO: 35), -$V_1F_2M_3M_4M_5$- (SEQ ID NO: 36), -$V_1V_2M_3M_4M_5$- (SEQ ID NO: 37), -$V_1E_2M_3M_4M_5$- (SEQ ID NO: 38), etc.), M→A substitution at position 1, and then a substitution of all 20 amino acids at position 2 (e.g., -$A_1A_2M_3M_4M_5$- (SEQ ID NO: 39), -$A_1F_2M_3M_4M_5$- (SEQ ID NO: 40), -$A_1V_2M_3M_4M_5$- (SEQ ID NO: 41), -$A_1E_2M_3M_4M_5$- (SEQ ID NO: 42), etc.).

In some embodiments of the step 204 of peptide maturation according to the instant disclosure, an amino acid deletion for each amino acid position of the core hit peptide may be performed. An amino acid deletion includes preparing a peptide including the core hit peptide sequence, but deleting a single amino acid from the core hit peptide sequence (such that a peptide is created in which the amino acid at each position is deleted). By way of example, referring back to the hypothetical core hit peptide having a 5-mer peptide with amino acid sequence -$M_1M_2M_3M_4M_5$- (SEQ ID NO: 22), an amino acid deletion would include preparing a series of peptides having the following sequences -$M_2M_3M_4M_5$- (SEQ ID NO: 43); -$M_1M_3M_4M_5$- (SEQ ID NO: 43); -$M_1M_2M_4M_5$- (SEQ ID NO: 43); -$M_1M_2M_3M_5$- (SEQ ID NO: 43); and -$M_1M_2M_3M_4$- (SEQ ID NO: 43). It should be noted that, following an amino acid deletion of the hypothetical 5-mer, 5 new 4-mers are created. According to some embodiments of the instant disclosure an amino acid substitution or a double amino acid substitution scan can be performed for each new 4-mer generated.

Similar to the amino acid deletion scan discussed above, some embodiments of the step 204 of peptide maturation disclosed herein may include an amino acid insertion scan, whereby each of the twenty amino acids is inserted before and after every position of the core hit peptide. By way of example, referring back to the hypothetical core hit peptide having a 5-mer peptide with amino acid sequence -$M_1M_2M_3M_4M_5$- (SEQ ID NO: 22), an amino acid insertion scan would include the following sequences, -$XM_1M_2M_3M_4M_5$- (SEQ ID NO: 44); -$M_1XM_2M_3M_4M_5$- (SEQ ID NO: 45); -$M_1M_2XM_3M_4M_5$- (SEQ ID NO: 46); -$M_1M_2M_3XM_4M_5$- (SEQ ID NO: 47); -$M_1M_2M_3M_4XM_5$- (SEQ ID NO: 48); and -$M_1M_2M_3M_4M_5X$- (SEQ ID NO: 49) (where X represents an individual amino, selected from the twenty natural amino acids or a specific, defined subset of amino acids, whereby a peptide replicate will be created for each of the twenty amino acids or defined subset of amino acids).

It should also be understood that the amino acid-substituted peptides, double amino acid-substituted peptides, amino acid deletion scan peptides and amino acid insertion scan peptides described above may also include one, or both of, an N-terminal and C-terminal wobble amino acid sequences (similar to as described for N-term 106 and C-term 108 in FIG. 1). As with the N-terminal and C-terminal wobble amino acid sequences described in FIG. 1 (N-term 106 and C-term 108), the N-terminal and C-terminal wobble amino acid sequences may comprise as few as one amino acid or as many as fifteen or twenty amino acids, and the N-terminal wobble amino acid sequence may be the same length as, longer than, or shorter than the C-terminal wobble amino acid sequence. In another aspect, either or both of the N-terminal wobble sequence and C-terminal wobble sequence can be omitted altogether. Further, the N-terminal and C-terminal wobble amino acid sequences may comprise any defined group of amino acids at any given ratios. For example, the wobble amino acid sequences may comprise glycine and serine in a 3:1 ratio (Gly:Ser), or a random mixture of all twenty canonical amino acids.

In one embodiment of the step 204, a core hit peptide having seven amino acids undergoes exhaustive single and double amino acid screens, and includes both N-terminal and C-terminal wobble amino acid sequences. In this example, each of the N-terminal and C-terminal sequences comprise three amino acids (all glycine). In other embodiments, different terminal sequences may be added by using different mixtures of amino acids during the maturation process. Any single amino acid can be used or any mixture consisting of two or more amino acids. In yet other embodiments, a mixture of Gly and Ser at a ratio 3:1 (Gly:Ser) is used. In other embodiments, a "random mix" is used consisting of a random mixture of all twenty amino acids. In some embodiments, non-natural amino acids (e.g., 6-aminohexanoic acid) are used. Further, some embodiments include non-amino acid moieties (e.g., polyethylene glycol).

Once the various substitution, deletion, and insertion variations of the core hit peptide are prepared (e.g., in immobilized fashion on a solid support such as a microarray), the strength of binding of the purified, concentrated target protein is assayed. As shown in the Examples provided below, the process of hit maturation allows for refining the core hit peptide to an amino acid sequence demonstrating the most preferred amino acid sequence for binding the target protein with the highest affinity.

VI. Peptide Extension (N-Terminal and C-Terminal)

It is possible that motifs identified in 5-mer array experiments represent only short versions of optimal protein binders. In one aspect, the present includes a strategy of identifying longer motifs by extending sequences selected from 5-mer array experiments by one or more amino acids from one or both N- and C-terminus. Starting from a selected peptide and adding one or more amino acids on each of the N-terminus and C-terminus, one can create an extension library for further selection. For example, starting from a single peptide and using all twenty natural amino acids, one can create an extension library of 160,000 unique peptides. In some embodiments, each of the extended peptides is synthesized in replicates.

Referring now to a step 206 of the process 200 in FIG. 2, upon maturation of the core hit peptide (such that a more optimal amino acid sequence of the core hit peptide is identified for binding the target protein) in the step 204, either or both of the N-terminal and C-terminal positions undergo an extension step, whereby the length of the matured core hit peptide from the step 204 is further extended for increasing the specificity and affinity for the target peptide.

Figure 3:
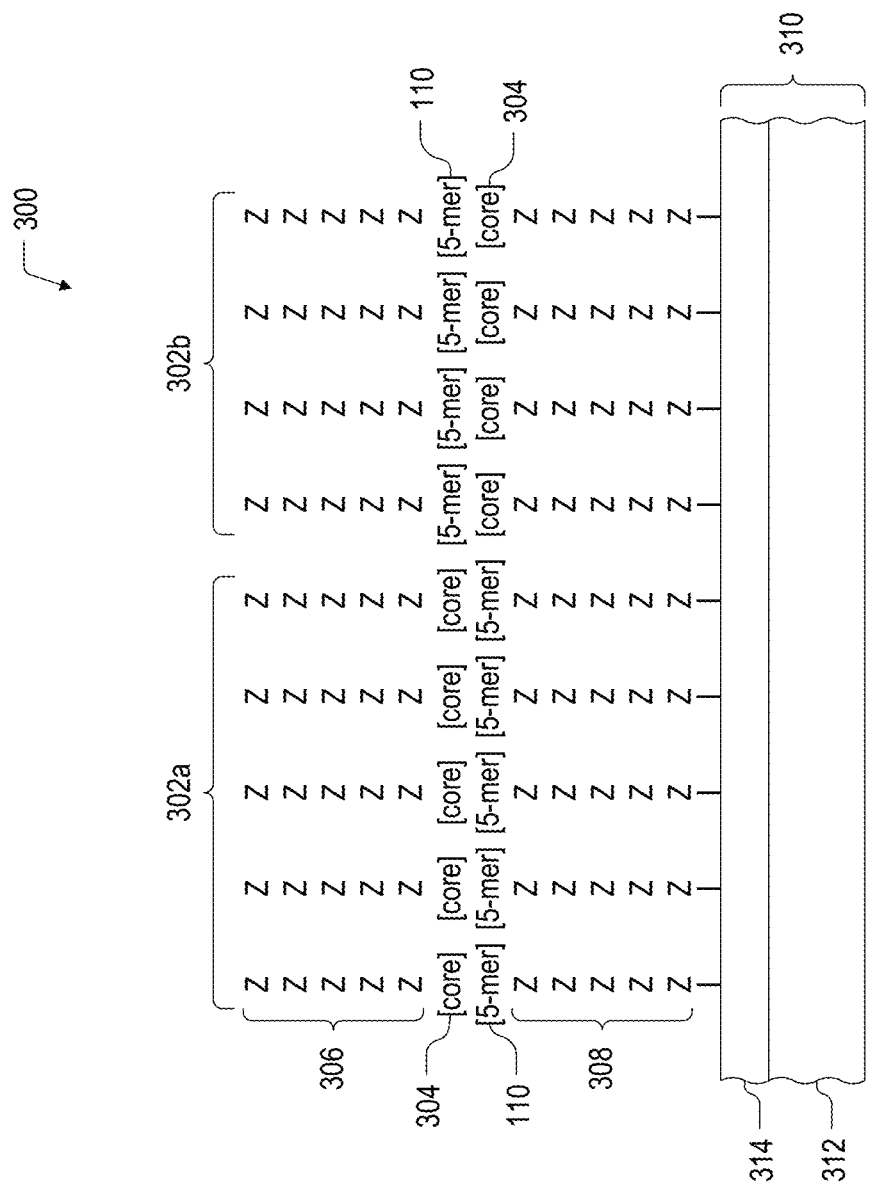
FIG. 3 is a schematic illustration of an embodiment of a maturation array including a population of peptides immobilized on solid support, where each of the peptides includes a matured core hit peptide sequence.

One example of C-terminal extension according to the instant disclosure is illustrated in FIG. 3. A peptide extension or maturation array 300 includes a first population of peptides 302a and a second population of peptides 302b. Each of the peptides 302a and the peptides 302b includes a matured core hit peptide 304 identified through the maturation process in the step 204 of the process 200 (FIG. 2). Specific peptide probes selected from the population of probe peptides (e.g., 5-mer probe peptides 110; FIG. 1) from the step 202 of peptide binder discovery is added to (or synthesized onto) the C-terminal end of a matured core hit peptide 304 of the first population of peptides 302a. In this manner, the most N-terminal amino acid of each peptide sequence is positioned directly adjacent to the most C-terminal amino acid of the matured core hit peptide 304.

Likewise, according to various embodiments of N-terminal extension of the instant disclosure, and with reference to FIG. 3, once the sequence of the matured core hit peptide 304 is identified through the maturation process (step 204; FIG. 2), each specific one of the 5-mer probe peptides 110 of the population 102 from the step 202 of peptide binder discovery (5-mer probe peptides 110, FIG. 1) is added to the N-terminal end of the matured core hit peptides 304 in the second population of peptides 302b. In this manner, the most C-terminal amino acid of each peptide sequence (5-mer probe peptides 110; FIG. 1) is added directly adjacent to the most N-terminal amino acid of the matured core hit peptide 304.

According to some embodiments of the instant disclosure (FIG. 3) one or both of the matured core hit peptides 304 used in C-terminal extension and N-terminal extension may also include either or both of an N-terminal wobble sequence (N-term 306) and a C-terminal wobble sequence (C-term 308). As with the N-term 106 and the C-term 108 in FIG. 1, the N-term 306 and C-term 308 may comprise as few as one amino acid or as many as fifteen to twenty amino acids (or more), and the N-term 306 may be the same length as, longer than, or shorter than the C-term 308. Further, the N-term 306 and C-term 308 can be added by using different mixtures of amino acids during the maturation process. Any single amino acid can be used or any "wobble mix" consisting of two or more amino acids. In yet other embodiments, a "flexible wobble mix" is used consisting of a mixture of Gly and Ser at a ratio 3:1 (Gly:Ser). In other embodiments, a "random wobble mix" is used consisting of a random mixture of all twenty amino acids. In some embodiments, non-natural amino acids (e.g., 6-aminohexanoic acid) can also be used. Some embodiments may include non-amino acid moieties (e.g., polyethylene glycol).

In FIG. 3, a peptide maturation array 300 is shown, having a population of peptides for C-terminal extension 302a and a population of peptides for N-terminal extension 302b. In the illustrated embodiment, the peptide maturation array 300 includes an array substrate 310 comprising a solid support 312 having a reactive surface 314 (e.g., a reactive amine layer for example) with the first population of peptides 302a and the second population of peptides 302b immobilized thereto. Each of the first population of peptides 302a and the second population of peptides 302b can include the full complement of 5-mer probe peptides 110 from peptide array 100 (e.g., used in the step 204 of peptide binder discovery). As further illustrated, each peptide of both the first population of peptides 302a and the second population of peptides 302b can include the same matured core hit peptide 304, each with a different 5-mer probe peptide 110 (of the population of 5-mer probe peptides 110 from the peptide binder discovery step 102, FIG. 1). Also as shown in FIG. 3, each peptide of the first population of peptides 302a and the second population of peptides 302b includes wobble amino acid sequences at the N-term 306 and the C-term 308.

In some embodiments, the maturation array 300 (including peptides 302a and peptides 302b) is exposed to a concentrated, purified protein of interest or another like receptor (as in peptide binder discovery; the step 202 of the process 200), whereby the protein may bind any peptide of either of the first population of peptides 302a and the second population of peptides 302b, independent of the other peptides comprising the first population of peptides 302a and the second population of peptides 302b. After exposure to the protein of interest, binding of the protein of interest to the peptide of the first population of peptides 302a and the second population of peptides 302b is assayed, for example, by way of exposing the complex of the individual peptide of the first population of peptides 302a and the second population of peptides 302b and protein to an antibody (specific for the protein) which has a reportable label (e.g., peroxidase) attached thereto. In another embodiment, the protein of interest may be directly labeled with a reporter molecule. Because the sequence of each of the 5-mer probe peptides 110 for each location on the array is known, it is possible to chart, quantify, compare, contrast, or a combination thereof, the sequences (and binding strengths) of the binding of the protein to the specific probe comprising the matured core hit peptide 304 with the respective one of the 5-mer probe peptides 110.

An exemplary method of comparing the protein (of interest) binding to the combination of the matured core hit peptide 304 and the 5-mer probe peptide 110 (comprising either of the first population of peptides 302a and the second population of peptides 302b) is to review the binding strength in a principled analysis distribution-based clustering, such as described by White et al., (Standardizing and Simplifying Analysis of Peptide Library Data, J Chem Inf Model, 2013, 53(2), pp 493-499). As is exemplified herein, clustering of protein binding to the respective probes (of the first population of peptides 302a and the second population of peptides 302b) shown in a principled analysis distribution-based clustering indicates 5-mer probe peptides 110 having overlapping peptide sequences. As demonstrated in greater detail below, from the overlapping peptide sequences (of each cluster), the sequence of the matured core hit peptide 304 can be identified, or at least hypothesized and constructed for further evaluation. In some embodiments of the instant application, an extended, matured core hit peptide 304 undergoes a maturation process (as described and exemplified herein and illustrated at the step 204 of FIG. 2).

Additional rounds of optimization of extended peptide binders are also possible. For example, a third round of binder optimization may include extension of the sequences identified in the extension array experiments with Gly amino acid. Other optimization may include creating double substitution or deletion libraries that include all possible single and double substitution or deletion variants of the reference sequence (i.e., the peptide binder optimized and selected in any of the previous steps).

VII. Specificity Analysis of Extended, Matured Core Hit Peptide Binders

Following identification of an extended, matured core hit peptide, a specificity analysis may be performed by any method of measuring peptide affinity and specificity available in the art. One example of a specificity analysis includes a "BIACORE™" system analysis which is used for characterizing molecules in terms of the molecules' interaction specify to a target, the kinetic rates (of "on," binding, and "off," disassociation) and affinity (binding strength). BIACORE™ is a trademark of General Electric Company and is available via the company website.

Figure 4:
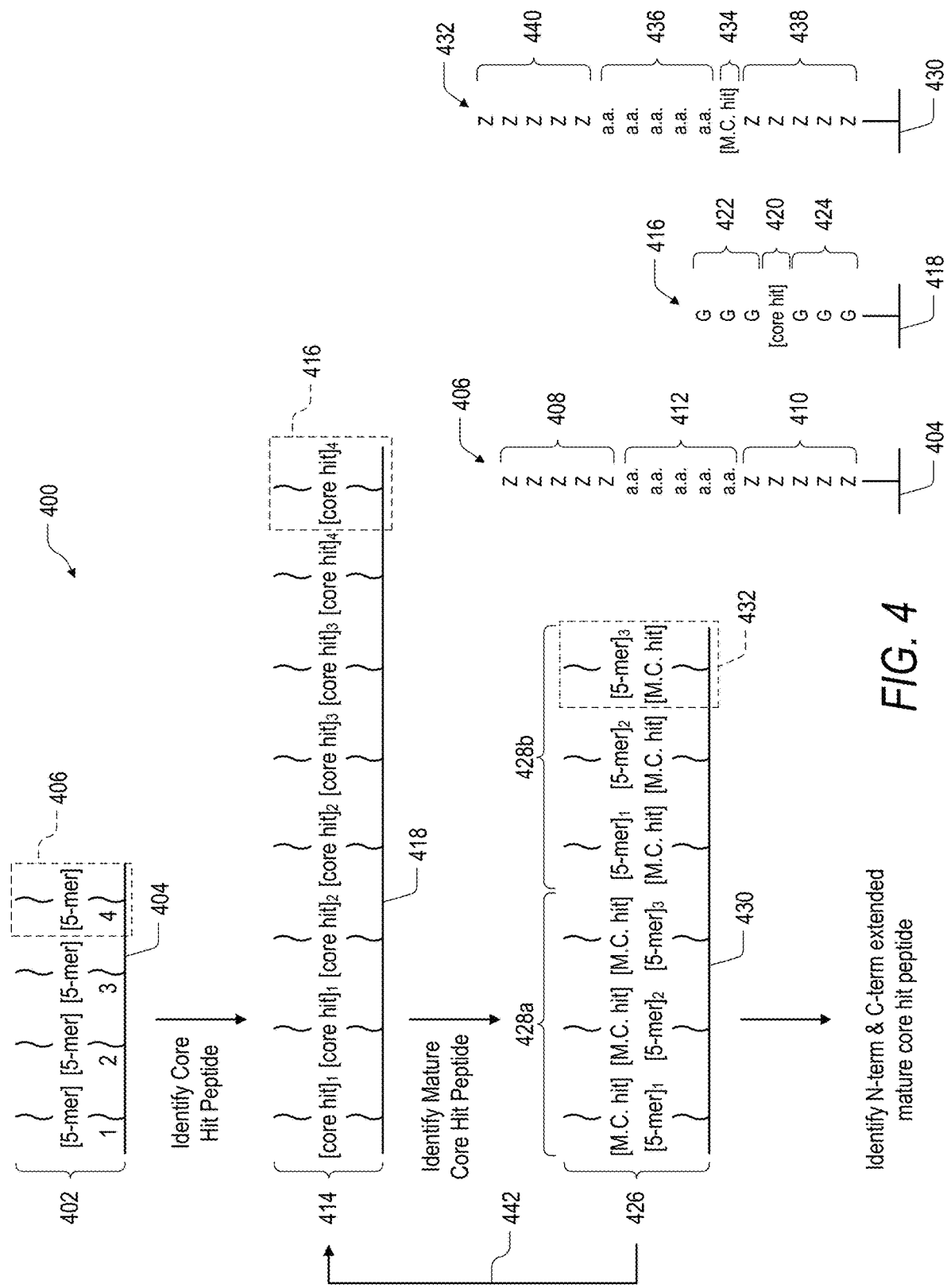
FIG. 4 is a schematic illustration of an embodiment of a method for the identification of peptide binders.

FIG. 4 is a brief schematic overview of a method 400 of novel peptide binder identification (e.g., process 200 of FIG. 2). As shown, an array 402 for peptide binder discovery is prepared by synthesizing (e.g., through maskless array synthesis) a population of peptides on an array substrate 404. As illustrated, each peptide 406 (or peptide feature) in the array 402 includes 5 cycles of wobble synthesis at the N-terminus (N-term 408) and 5 cycles of wobble synthesis at the C-terminus (C-term 410) such that each of the N-term 408 and C-term 410 comprises five amino acids. It should be understood that the wobble synthesis of the N-term 408 and C-term 410 may comprise any composition as noted above. For example, wobble synthesis can comprise only amino acids Gly and Ser, in a 3:1 ratio (Gly:Ser), or a random mixture of all 20 amino acids. Each peptide 406 is also shown as comprising a 5-mer peptide binder or probe peptide 412, which as noted above may comprise up to 2.9 million different peptide sequences such that an entire human proteome is represented. Further, it should be noted that the different probe peptides 412 may be synthesized according to specific "rules." Non-limiting example rules include the exclusion of one or more amino acids (e.g., Cys, Met, or a combination thereof), the exclusion of repeats of the same amino acid in consecutive order, the exclusion of motifs already known to bind the target protein (e.g., His-Pro-Gln amino acid motifs for streptavidin), and combinations thereof. As described above, a protein target of interest (e.g., in purified and concentrated form) is exposed to the 5-mer probe peptides 412, and binding is scored (e.g., by way of a principled clustering analysis), whereby a "core hit peptide" sequence is identified based on overlapping binding motifs.

In some embodiments, upon identification of a core hit peptide sequence, an exhaustive maturation process may be undertaken as illustrated for the maturation or maturation array 414. The maturation array 414 includes a population of peptides 416 that are immobilized to an array substrate 418. In some embodiments, the core hit peptide (exemplified as a 5-mer core hit peptide 420) is synthesized on the array substrate 418 with both an N-terminal wobble sequence (N-term 422) and a C-terminal wobble sequence (C-term 424). In the example illustrated in FIG. 4, each of the peptides 416 includes three cycles of N-terminal and C-terminal wobble synthesis of only the amino acid Gly, although the wobble amino acid may vary as noted above. In some embodiments of exhaustive maturation, a core hit peptide 416 is synthesized on the array substrate 418 wherein every amino acid position of the core hit peptide 416 is substituted with each of the other nineteen amino acids or a double amino acid substitution (as described above) is synthesized on the array substrate 418 or an amino acid deletion scan is synthesized on the array substrate 418, or an amino acid insertion scan is synthesized on the array substrate 418. In some cases, all of the above maturation processes are performed (and optionally repeated as described above for the new peptides generated as a result of the amino acid deletion and insertion scans). Upon synthesis of the maturation array 414 comprising the various peptides (inclusive of the substitutions, deletions and insertions described herein), the target protein is exposed to the modified core hit peptides 420 on the maturation array 414, and strength of binding is assayed, whereby a "matured core hit peptide" sequence is identified.

In further embodiments, after identification of a "matured core hit peptide" sequence, one or both of N-terminal and C-terminal extensions may be performed as illustrated for an extension array 426. The extension array 426 includes a first population of peptides 428a and a second population of peptides 428b that are each immobilized to an array substrate 430. As illustrated for a selected peptide 432 of the second population of peptides 428b, each of the first population of peptides 428a and the second population of peptides 428b includes a matured core hit peptide 434 (M.C. hit) coupled to an extension sequence 436 at either the N-terminus (in the case of the second population of peptides 428b) or the C-terminus (in of the case of first population of peptides 428a). N-terminal and C-terminal extensions involve the synthesis of the matured core hit peptides 434 adjacent the population of probe peptides 412 (in this example, 5-mers). The probe peptides 416 are synthesized at either the N-terminus or C-terminus of the matured core hit peptides 434. As shown for the first population of peptides 428a, C-terminal extension involves five rounds of wobble synthesis to provide a C-terminal wobble sequence (C-term 438) and the extension sequence 436 being synthesized C-terminally of the matured core hit peptide 434, followed by another 5 cycles of wobble synthesis to provide an N-terminal wobble sequence (N-term 440). Similarly, as shown for the second population of peptides 428b, N-terminal extension involves five rounds of wobble synthesis (as described above) yielding the C-term 438, which is synthesized C-terminally of the matured core hit peptide 434, then the extension sequence 436 and another 5 cycles of wobble synthesis to provide the N-term 440. Upon synthesis of the extension array 426 comprising the various C-terminal and N-terminal extension peptides (i.e., the first population of peptides 428a and the second population of peptides 428b), the target protein is exposed to the extension array 426, and binding is scored (e.g., by way of a principled clustering analysis), whereby a sequence of the C-terminally or N-terminally extended, matured core hit peptide 434 is identified. As represented by the arrow indicated at 442, according to some embodiments, after the extended, matured core hit peptide (e.g., peptide 432) is identified, the maturation process for the extended matured core hit peptide may be repeated and then the extension process may also be repeated for any altered peptide sequence resulting therefrom.

VIII. Identification of Binder Peptides for Specific Targets

According to embodiments of the instant disclosure, peptide microarrays are incubated with samples including the target proteins to yield specific binders for various receptors. Example receptors include streptavidin, Taq polymerase, human proteins such as prostate specific antigen, thrombin, tumor necrosis factor alpha, urokinase-type plasminogen activator, or the like. Methods and example peptide binders for the aforementioned receptors are described by Albert et al. (U.S. Pat. App. No. 2015/0185216 to Albert et al. and U.S. Prov. Pat. App. Ser. No. 62/150,202 to Albert et al.).

While the identified peptide binders may be used for various binder-specific purposes, some uses are common to all binders. For example, for each of the targets described herein, the peptide binders of the present invention may be used as quality control peptides for inclusion in the synthesis of a broader population of peptides (e.g., for use on a peptide array for discovery of new peptide binder sequences).

Turning now to FIG. 5, a peptide array 500 includes a plurality of peptides including a first population of peptides 502 and a second population of peptides 504. The peptides 502 and the peptides 504 are immobilized on an array substrate 506 that includes a solid support 508 having a reactive surface 510 (e.g., a reactive amine layer). Each of the peptide sequences of the peptides 502 and the peptides 504 is based on a peptide binder sequence that was previously identified as described herein. In the embodiment illustrated in FIG. 5, the identified peptide binder sequence or binder sequence is [N]-Gly-Phe-Glu-Asp-Tyr-Leu-Gly-Glu-Tyr-His-Gly-[C] (SEQ ID NO:1) as shown for the peptide binder 512. For each amino acid within the sequence of the peptide binder 512, a series of substitutions and deletions may be made, for example, to identify which amino acids have the greatest impact on the affinity of a receptor for the peptide binder 512. Accordingly, the peptide array 500 can include subsequent peptide sequences within the peptides 502 that represent amino acid substitutions for each of the amino acid positions with the peptide sequence included in the peptide binder 512. In the illustrated embodiment, the amino acid His at the tenth position 514 from the N-terminus of the peptides 502 and the peptides 504 is modified either by substitution, deletion, or the like. For example, whereas the leftmost peptide (peptide binder 512) has a His at the tenth position from the N-terminus, the next adjacent peptide sequence to the right of the peptide binder 512 includes a His→Ala substitution. Continuing to the right, the His is successively substituted with Cys, Asp, and each of the other amino acids selected from the 20 canonical amino acids as indicated by the ellipses followed by the peptide sequence including the His→Tyr substitution at the tenth position 514 from the N-terminus of the peptide binder 512.

Whereas the first population of peptides 502 includes various amino acid substitutions at the tenth position 514, the second population of peptides 504 includes amino acid deletions at the tenth position 514 achieved under various synthesis conditions. In a first example, the bracketed number 1 (i.e., [1]) indicates that solvent alone (with no amino acid present) was tested to approximate the total degradation of an amino acid reagent supply during synthesis of the peptide array 500. In a second example, the bracketed number 2 (i.e., [2]) indicates a synthesis step carried out with no reagent, solvent, or amino acid to approximate the complete failure of an amino acid pump or other supply line in communication with the peptide array 500 during synthesis. In a third example, the bracketed dash mark (i.e., [-]) indicates the synthesis of a His deletion peptide, where the His at the tenth position 514 is removed from the peptide sequence altogether.

Figure 6A:
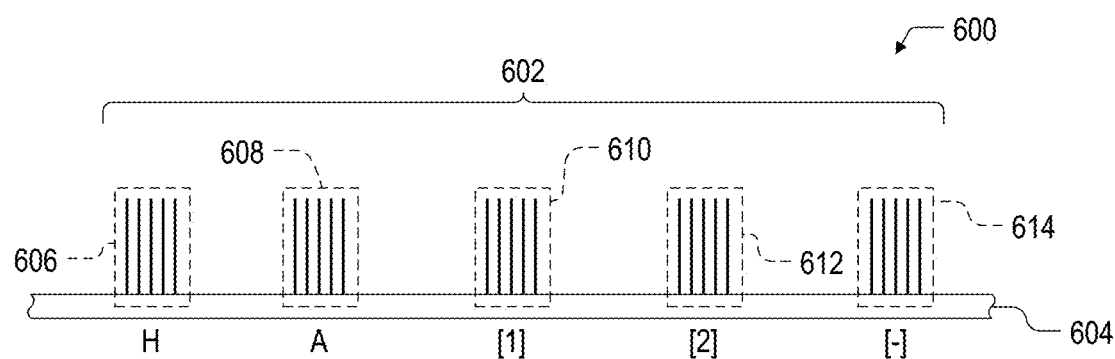
FIG. 6A is a schematic illustration of an embodiment of a peptide array including a population of peptide features for the identification and characterization of control peptides.
Figure 6B:
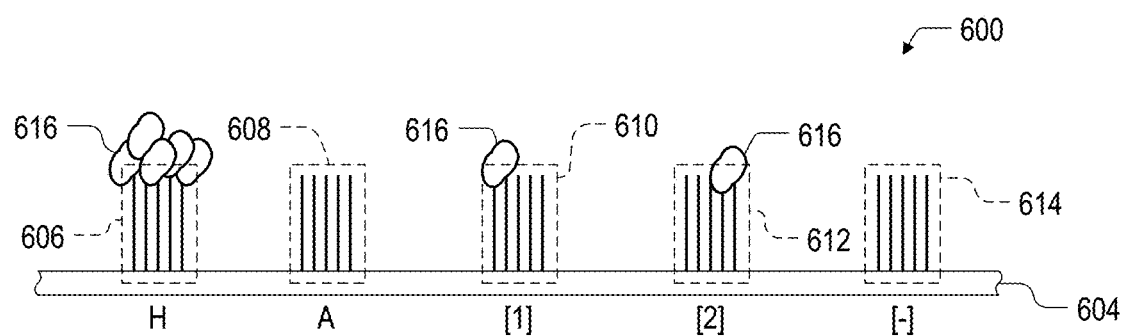
FIG. 6B is a schematic illustration of an embodiment of the peptide array of FIG. 6A following exposure of the peptide features to a plurality of receptor molecules.
Figure 6C:
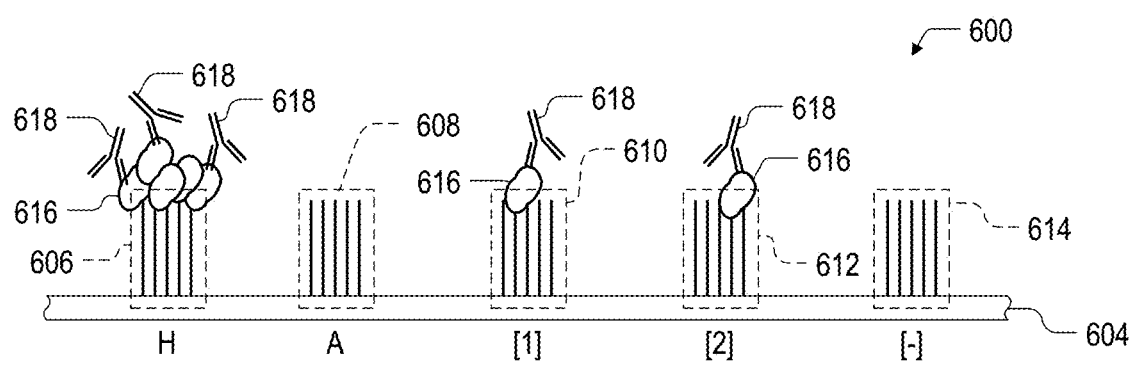
FIG. 6C is a schematic illustration of an embodiment of the peptide array of FIG. 6B following binding of a detectable tag to the receptor molecules.

With reference to FIGS. 6A-6C, a peptide array 600 includes a population of peptide features 602 immobilized on an array substrate 604. Each of the peptide features 602 includes a plurality of colocalized peptides sharing the same amino acid sequence. Depending on the synthesis method employed, a peptide feature may have a varying footprint or feature density. In one example, a peptide feature has a footprint of about 10 µm×10 µm square and includes up to about $10^7$ individual peptides. However, other footprints and feature densities are possible as will be recognized of a person of ordinary skill in the art. In the present example, the peptide feature 606 includes a plurality of peptides that each have the amino acid sequence of the peptide binder 512 of FIG. 5 (i.e., [N]-Gly-Phe-Glu-Asp-Tyr-Leu-Gly-Glu-Tyr-His-Gly-[C] (SEQ ID NO:1)). The letter 'H' beneath the peptide feature 606 indicates that the tenth amino acid from the N-terminus of each of the peptides that make up the peptide feature 606 is a His. The peptide array 600 further includes a peptide feature 608 having a plurality of peptide sequences similar to the sequences comprising the peptide feature 606 with the exception of a His→Ala substitution at the tenth amino acid position from the N-terminus as indicated by the letter 'A' beneath the peptide feature 608. Notably, the peptide array 600 can include numerous peptide features beyond the number of features shown in the embodiment illustrated in FIG. 6.

As in the case of the peptide array 500 (FIG. 5), the peptide array 600 includes a peptide feature 610, a peptide feature 612, and a peptide feature 614, where each of the peptide feature 610, the peptide feature 612, and the peptide feature 614 includes a plurality of peptides that each have the amino acid sequence similar to that of the peptides within the peptide feature 606. In one aspect, the peptide feature 610, the peptide feature 612, and the peptide feature 614 include amino acid deletions at the tenth position 514 achieved under various synthesis conditions. The peptide feature 610 (denoted with VT) indicates sequences where solvent alone (with no amino acid present) was tested to approximate the total degradation of an amino acid reagent supply during synthesis of the peptide array 600. The peptide feature 612 (denoted with '[2]') indicates sequences where a synthesis step was carried out with no reagent, solvent, or amino acid to approximate the complete failure of an amino acid pump or other supply line in communication with the peptide array 600 during synthesis. The peptide feature 614 (denoted with '[-]') indicates the synthesis of a His deletion peptide, where the His at the tenth position is removed from the peptide sequence altogether. Alternative or additional synthesis conditions and peptide feature can also be included or mimicked using a peptide array according to the present disclosure.

Once the peptide array 600 has been synthesized as illustrated in FIG. 6A, a plurality of receptor molecules known to interact with the selected peptide binder sequences can be contacted to the peptide array 600 in order to interrogate the population of peptide features 602 in the presence of the receptor molecules (FIG. 6B). A number of receptor molecules 616 are shown as interacting with the peptide feature 606. Interaction of the receptor molecules 616 with the peptide feature 606 can include binding, catalysis of (or participation in) a reaction including peptides within the peptide feature 606, digestion of the peptides within the feature 606, the like, and combinations thereof. In the present example shown in FIGS. 6A-6C, the receptor 616 was used in the identification of the peptide binder sequence represented by the peptides in the feature 606 (i.e., [N]-Gly-Phe-Glu-Asp-Tyr-Leu-Gly-Glu-Tyr-His-Gly-[C] (SEQ ID NO:1)). Accordingly, a strong degree of interaction between the peptides in the peptide feature 606 and the receptor molecules 616 would be anticipated as represented by the plurality of receptor molecules 616 associated with the feature 606. In one aspect, the interaction of the receptor molecules 616 with the population of peptide features 602 on the peptide array 600 can be detected, for example, by labelling the receptor molecules 616 with a detectable tag 618 (FIG. 6C). As shown in the illustrated embodiment, the detectable tag 618 is a labeled antibody that is specific for targeting the receptor molecules 616. However, other detection schemes are within the scope of the present disclosure.

Whereas a plurality of receptor molecules 616 are associated with the feature 606 in FIG. 6B, relatively few or no receptor molecules 616 are associated with any one of the peptide feature 608, the peptide feature 610, the peptide feature 612, and the peptide feature 614. In one aspect, a His→Ala substitution represented by the peptides in the peptide feature 608 results in little to no interaction of the receptor molecules 616 with the peptide feature 608. In another aspect, a His deletion as a result of various synthesis conditions represented by the peptides in the peptide feature 610, the peptide feature 612, and the peptide feature 614 results in little to no interaction of the receptor molecules 616 with the aforementioned peptide features. As a result, a preference of the receptor molecules for a His amino acid at the tenth position from the N-terminus can be inferred. Similarly, the degree of interaction or the relative change in the extent of interaction of the receptor molecules 616 with any of the peptide features on the peptide array 600 can be interrogated. Moreover, the results of the interrogation can be used to identify for which amino acid substitutions or deletions and at which positions in the selected peptide binder sequences a detectable and distinguishable (unique) change in the interaction of the receptor molecules 616 with the peptide features can be observed.

Figure 7A:
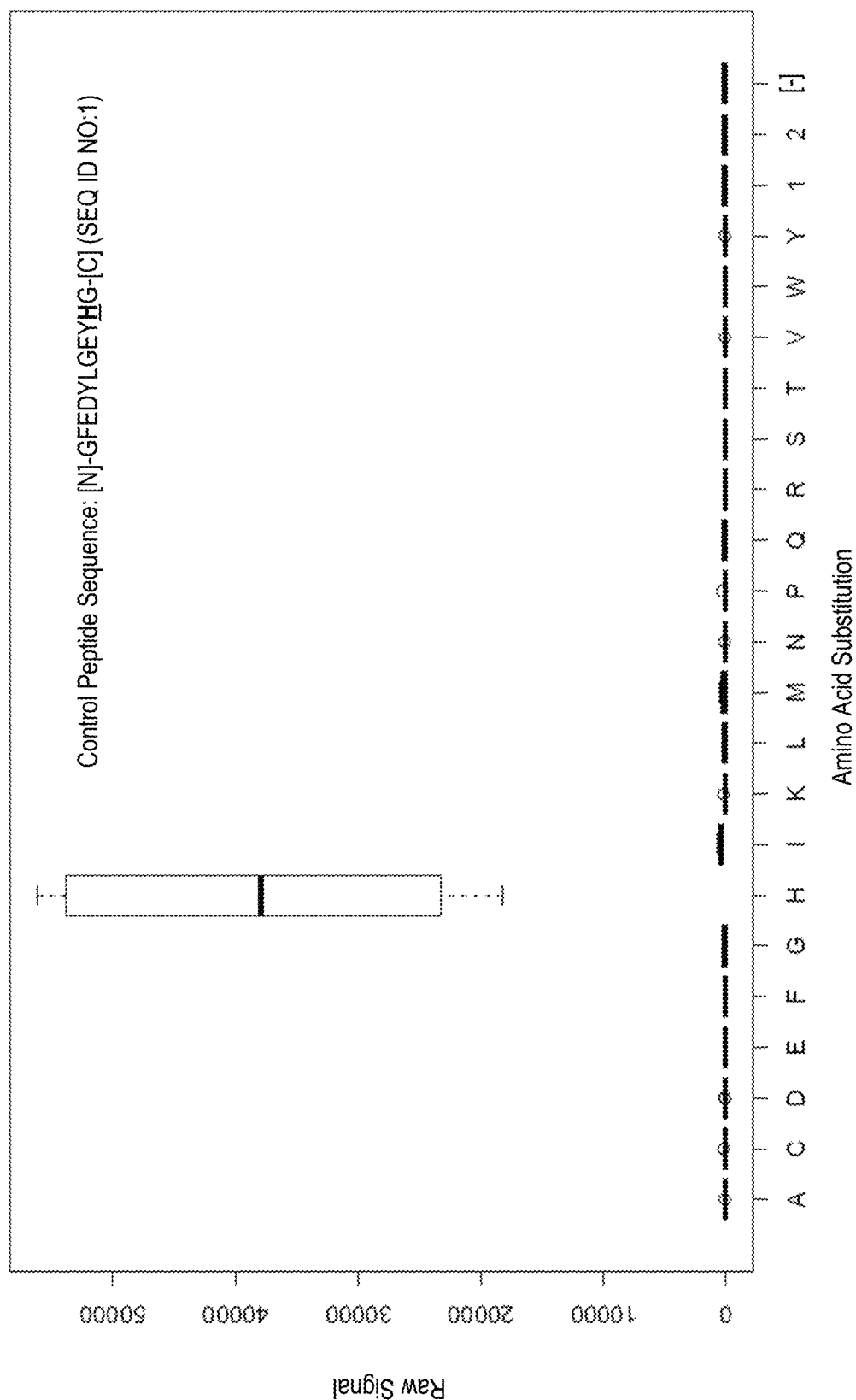
FIG. 7A is a profile of raw fluorescence signal for a control peptide having the sequence [N]-GFEDYLGEYHG-[C] (SEQ ID NO:1). Sequences comprising each possible amino acid substitution and deletion for the His at the $10^{th}$ position from the N-terminus were analyzed as indicated along the horizontal axis. The illustrated control peptide sequence can be used to assess incorporation of the amino acid His.
Figure 7B:
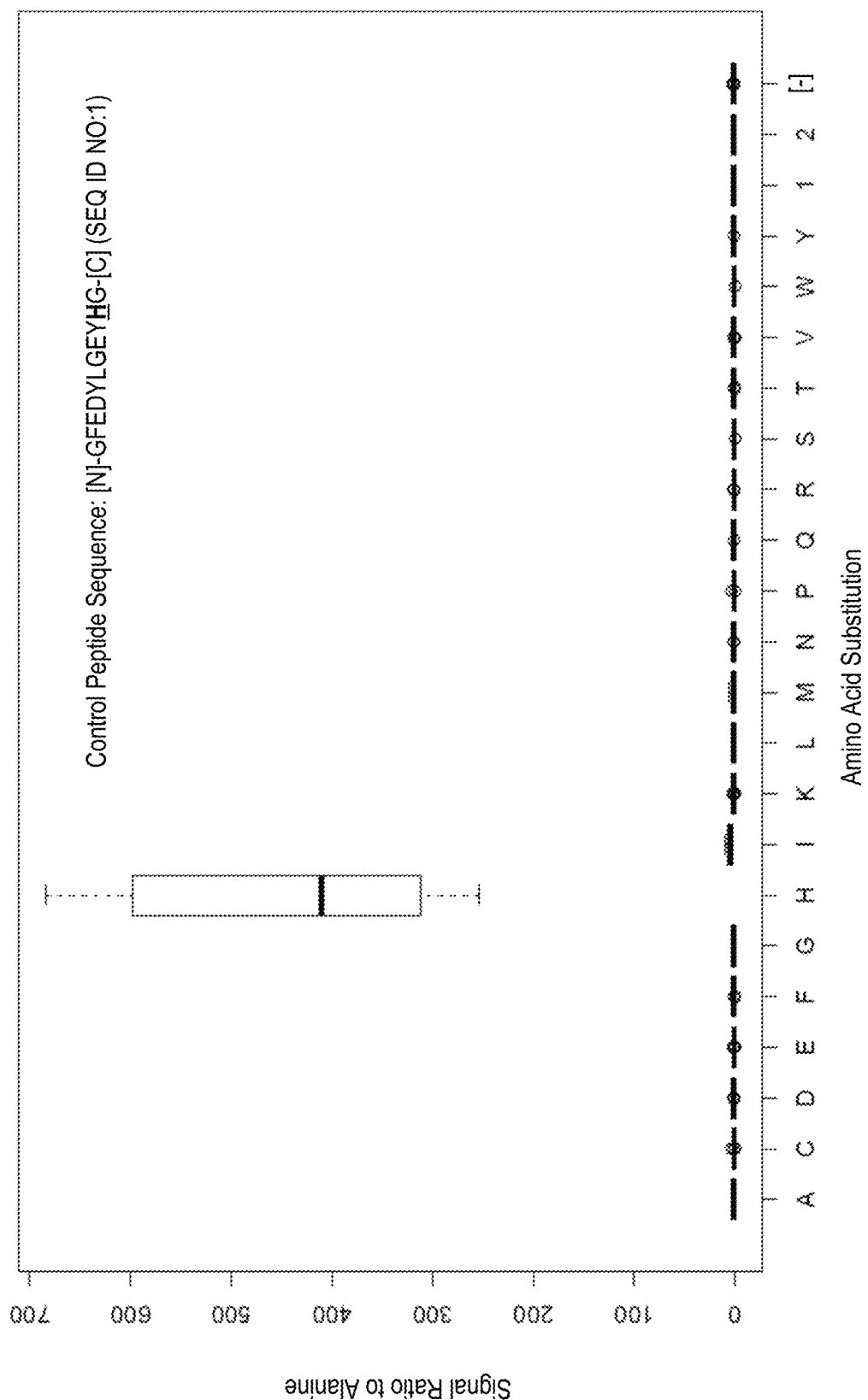
FIG. 7B is a profile of fluorescence signal ratio with respect to alanine for the control peptide of FIG. 7A. Sequences comprising each possible amino acid substitution and deletion for the His at the $10^{th}$ position from the N-terminus were analyzed as indicated along the horizontal axis.

By distinguishable or unique, it is meant that for each of the detected signal outputs (absolute or relative) associated with an interaction between the receptor molecules 616 and a selected one of the various features on the peptide array 600, a particular signal output has a unique signature or value that can be differentiated from each of the other signal outputs for a given set of peptide binder sequence variants. For example, with reference to FIGS. 7A and 7B, a substitution and deletion profile for the His amino acid in the example peptide binder sequence [N]-Gly-Phe-Glu-Asp-Tyr-Leu-Gly-Glu-Tyr-His-Gly-[C] (SEQ ID NO:1) reveals that any substitution (twenty canonical amino acids) or deletion of the His amino results in complete loss of signal for both a measure of raw signal (FIG. 7A) or relative to the signal output for an Ala substitution (FIG. 7B). Accordingly, the example peptide binder sequence in FIGS. 7A and 7B can be used as a quality control peptide to monitor the successful incorporation of the amino acid His during a peptide synthesis process. In order to monitor successful incorporation of additional amino acids other than His, it can be useful to select additional peptide binders for inclusion as quality control peptides based on the methods disclosed herein.

Figure 6D:
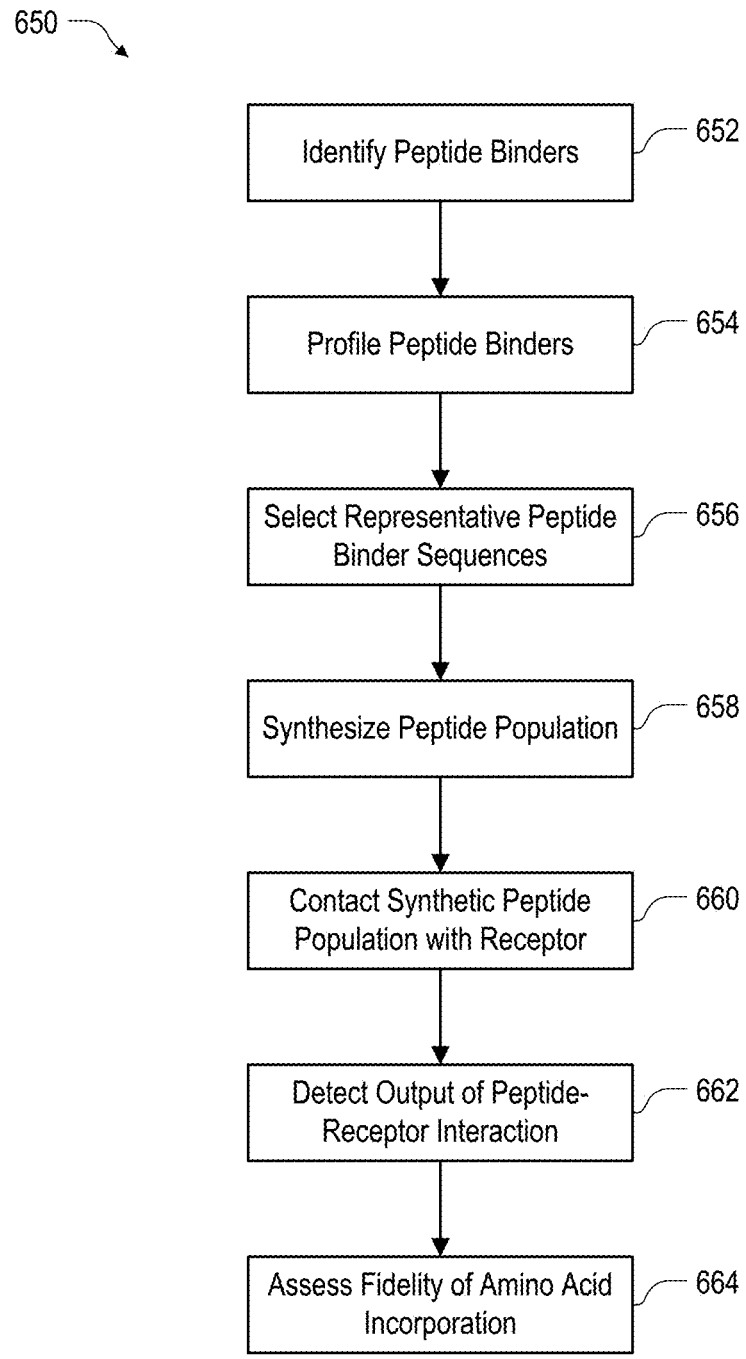
FIG. 6D is an example of a method of assessing the fidelity of a synthetic peptide population according to the present disclosure.

Turning now to FIG. 6D, a method 650 of assessing the fidelity of a synthetic peptide population includes a step 652 of identifying peptide binders. As discussed above, peptide binders can be identified using a peptide array comprised of 5-mer peptide binder sequences. One example method of identifying peptide binders is illustrated by the method 200 (FIG. 2), with peptide binders being identified in the step 208. Suitable peptide binders include binder sequences or affinity sequences that are recognizable by a receptor that has an affinity for the binder sequences. The set of binder sequences (for which there exists one or more receptors) are then profiled in a step 654 of the method 650. The step 654 can include preparing, for each of the selected binder sequences from the step 652, a series of substitution and deletion sequences in order to generate a signal output profile. In one embodiment, for each amino acid within a given binder sequence, a series of substitutions and deletions may be made to identify which modifications result in a unique or distinguishable change in the affinity of a receptor for the peptide binder. Accordingly, the peptide array for profiling can include peptide sequences having amino acid substitutions for each of the amino acid positions within the peptide binder sequence. Example illustrations of peptide arrays for profiling a selected peptide binder sequence are shown in FIGS. 5 and 6A-6C.

In a step 656 of the method 650, a set of peptide binder sequences is selected that is representative of each of the amino acid reagents to be assessed following synthesis of a subsequent peptide population. In one example, it may be useful to synthesize a synthetic peptide population using only the twenty canonical amino acids, and therefore assess the fidelity of incorporation of each of the twenty canonical amino acids. Accordingly, the step 654 can include the preparation of substitution (and deletion) profiles for each of the twenty canonical amino acids (e.g., FIGS. 7A and 7B). Thereafter, a set of peptide binder sequences can be selected in the step 656 for monitoring successful incorporation of each of the twenty canonical amino acids. In one aspect, one or more peptide binder sequences can be selected to assess a single amino acid. For example, the peptide sequence profiled in FIGS. 7A and 7B can be used solely to assess the incorporation of the amino acid His. However, peptide binder sequences can be selected to assess more than one amino acid (or other peptide monomer reagent). For example, the peptide binder sequence profiled in FIGS. 8A and 8B can be used to assess the incorporation of either or both of the amino acids Met and Gln as the interaction between each one of the of two profiled binder sequences with the corresponding binder is unique and distinguishable from the other of the two profiled binder sequences. Notably, by selecting peptide binder sequences that are useful for assessing more than one amino acid, it is possible to select fewer peptide binder sequences than the total number of amino acids (or other reagents) used for peptide synthesis.

However, an equal or greater number of peptide binder sequences can additionally (or alternatively) be selected to assess the fidelity of a synthetic peptide population. Moreover, more than one peptide binder sequence can be selected to monitor the same amino acid (e.g., see Table 1).

In a step 658 of the method 650, a synthetic peptide population is synthesized using any suitable method, including those methods described herein. The design of the synthetic peptide population includes a plurality of control peptides where each of the control peptides includes one of the peptide binder sequences selected in the step 656. In one aspect, each of the control peptides features is synthesized to have an amino acid sequence including a selected one of the binder sequences. However, it is anticipated that one or more synthesis errors may occur that will result in control peptides having a sequence that differs from the selected peptide binder sequence. Errors that may occur during synthesis can include mechanical failures that impact delivery of the various reagents to the peptide array, degradation of one or more of the reagents, and the like. For example, each of the amino acids used for peptide synthesis is delivered from a separate reservoir. If one of the fluid connections to an amino acid reservoir fails, or if the amino acid reagent in the reservoir is degraded, then synthesis errors will be present for each peptide synthesized with the amino acid reagent in question. In certain situations, even though the error occurred, the peptide array can still be generated with the errors remaining initially undetected. As a result, the actual control peptide sequence can differ from the selected control peptide sequence.

In a next step 660 of the method 650, the synthetic peptide population is interrogated in the presence of a receptor having an affinity for the peptide binder sequences encoded by the control peptides. In one aspect, the step 660 can include contacting the population of peptides with a plurality of receptor molecules (e.g., antibodies, peptides, proteins, enzymes, or the like). The receptor molecules can be unlabeled or labeled with a detectable tag such as a fluorescent marker. In another aspect, the step 660 can include labeling the receptor molecules with a detectable reporter molecule, such as a primary (and optionally a secondary) antibody, a dye, the like, or a combination thereof. Thereafter, in a step 662 of the method 650, an output of the peptide-receptor interaction is detected. The step 662 can include detecting the presence of the receptor using an optical technique (e.g., absorbance, luminescence, reflectance, etc.), a chemical technique (e.g., enzymatic assays), or another suitable method of detecting a signal output characteristic of an interaction of the receptor with the control peptides or control peptide features. In one aspect, the signal output is indicative of the fidelity of incorporation of a particular amino acid into a corresponding control peptide. Further, as the position of the particular amino acid in the control peptide sequence is known (i.e., the amino acid is at a defined position), it is further possible to assess whether the position of the amino acid is correct. Accordingly, based on the output detected in the step 662, a step 664 of the method 650 can include assessing the fidelity of amino acid incorporation. That is, for a control peptide synthesized at a known location, the detected interaction of a receptor in the presence of the control peptide is indicative of whether a particular amino acid was successfully incorporated both in general and at the correct position within the control peptide sequence.

IX. Examples

Streptavidin Binders

In some embodiments, the present disclosure provides isolated artificial control peptides with specific affinity to streptavidin. In this embodiment, the disclosure includes peptides consisting of sequences listed in Table 1. The disclosure further includes peptides comprising sequences listed in Table 1. Accordingly, shorter or longer peptides (e.g., 5, 6, 7, 8, 9, and up to 20 amino acids) comprising sequences listed in Table 1 are also part of the invention. Corresponding plots of absolute and relative signal are shown in FIGS. 7-23, with amino acids listed according to their single letter code along the horizontal axis. Synthesis conditions [1], [2], and [-] as described above are indicated as 1, 2, and [-], respectively.

TABLE 1

| Sequence | Target Position | Amino Acid(s) Queried |
| --- | --- | --- |
| GFEDYLGEYHG (SEQ ID NO: 1) | 10 | Histidine (H) |
| GWTHPMFEQKG (SEQ ID NO: 2) | 6 | Methionine (M), Glutamine (Q) |
| WKHPQAGS (SEQ ID NO: 3) | 6 | Alanine (A) |
| ASWCHPQGPC (SEQ ID NO: 4) | 4 | Cysteine (C) |
| ASYDHPQGGR (SEQ ID NO: 5) | 4 | Aspartic Acid (D), Glutamic Acid (E) |
| GNSFDDWLQKG (SEQ ID NO: 6) | 4 | Phenylalanine (F) |
| ASWPHPQSGM (SEQ ID NO: 7) | 9 | Glycine (G) |
| ASWIHPQFQG (SEQ ID NO: 8) | 4 | Threonine (T), Valine (V) |
| VWHPQSGK (SEQ ID NO: 9) | 8 | Lysine (K) |
| GNSFDDWLNKG (SEQ ID NO: 10) | 8 | Leucine (L), Isoleucine (I) |
| WWHPQNAV (SEQ ID NO: 11) | 6 | Asparagine (N) |
| WVHPQFQT (SEQ ID NO: 12) | 4 | Proline (P) |
| RYHPQ (SEQ ID NO: 13) | 4 | Arginine (R) |

TABLE 1-continued

| Sequence | Target Position | Amino Acid(s) Queried |
|---|---|---|
| ASYPHPQSGQ (SEQ ID NO: 14) | 8 | Serine (S) |
| KNTFDEWLQKG (SEQ ID NO: 15) | 3 | Threonine (T) |
| ASWVHPQFQN (SEQ ID NO: 16) | 3 | Tryptophan (W) |
| SFEDYLAEYHG (SEQ ID NO: 17) | 5 | Tyrosine (Y) |

As discussed above with respect to FIGS. 7A and 7B, a first control peptide including GFEDYLGEYHG (SEQ ID NO:1) (Table 1) can be used to identify the fidelity of incorporation of the amino acid His into a synthetic population of peptides including the first control peptide. In one aspect any substitution or deletion at the $10^{th}$ position from the N-terminus of GFEDYLGEYHG (SEQ ID NO:1) (i.e., the position of the amino acid His) results in a loss of signal corresponding to an interaction between the first control peptide and the streptavidin receptor. Moreover, the loss of signal is distinguishable relative to the signal produced from the interaction between the streptavidin receptor and the first control peptide in terms of both raw signal (FIG. 7A) and signal relative to a control peptide with the His→Ala substitution (FIG. 7B).

Figure 8A:
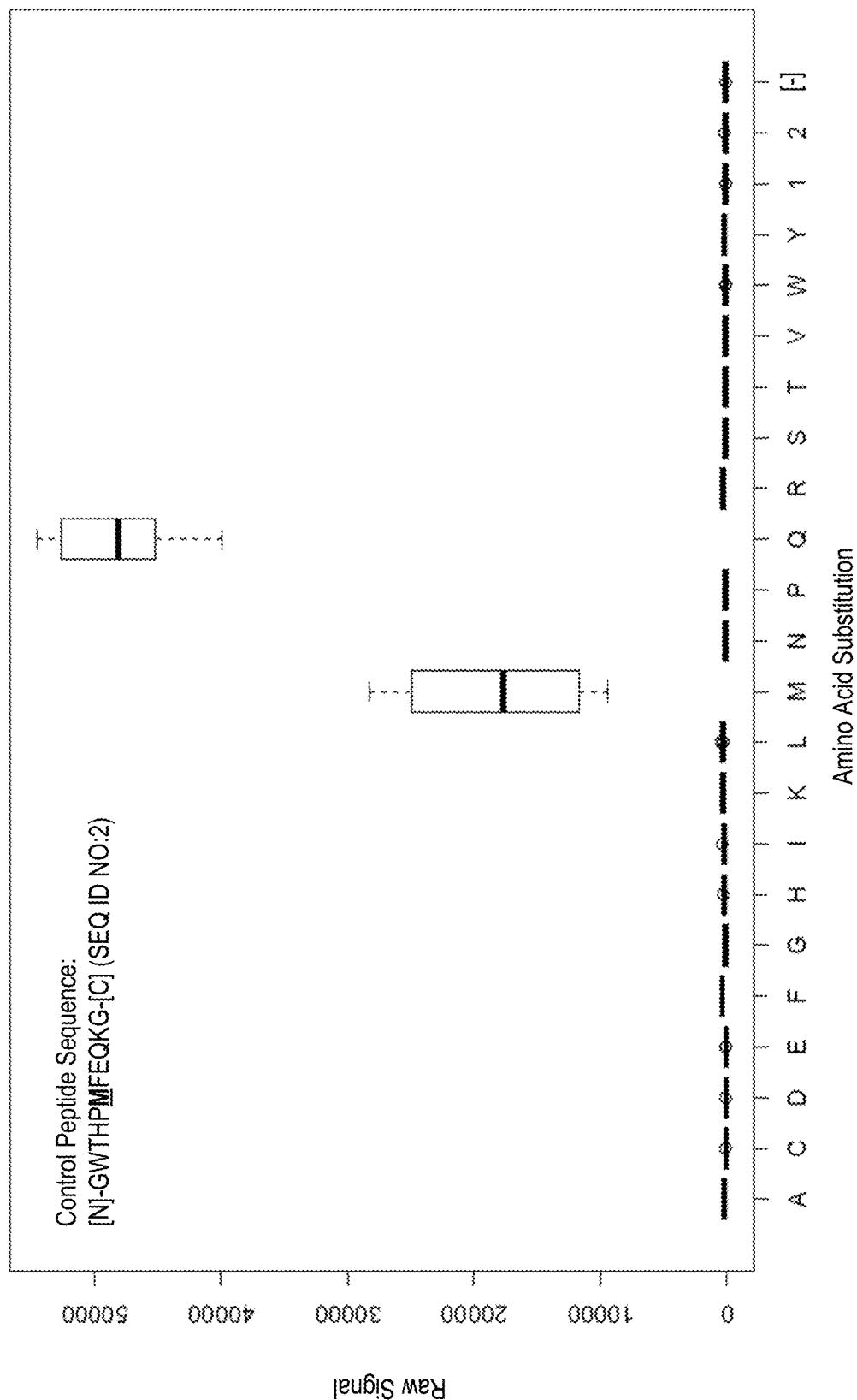
FIG. 8A is a profile of raw fluorescence signal for a control peptide having the sequence [N]-GWTHPM-FEQKG-[C] (SEQ ID NO:2). Sequences comprising each possible amino acid substitution and deletion for the Met at the $6^{th}$ position from the N-terminus were analyzed as indicated along the horizontal axis. The illustrated control peptide sequence can be used to assess incorporation of the amino acids Met and Gln.
Figure 8B:
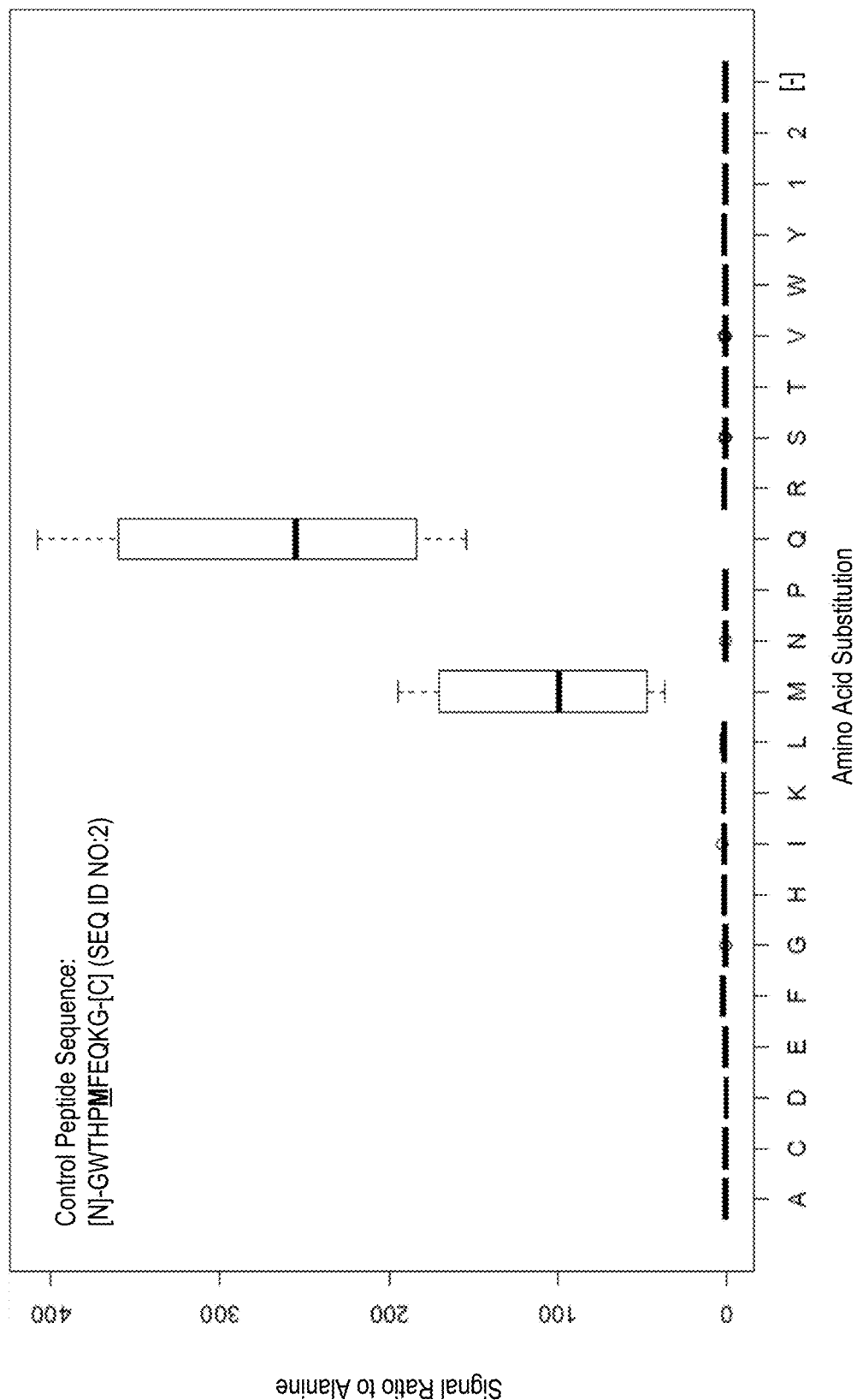
FIG. 8B is a profile of fluorescence signal ratio with respect to alanine for the control peptide of FIG. 8A. Sequences comprising each possible amino acid substitution and deletion for the Met at the $6^{th}$ position from the N-terminus were analyzed as indicated along the horizontal axis.

In another example, and with respect to FIGS. 8A and 8B, a second control peptide including GWTHPMFEQKG (SEQ ID NO:2) (Table 1) can be used to identify the fidelity of incorporation of either of the amino acids Met and Gln into a synthetic population of peptides including the second control peptide. In one aspect any substitution or deletion at the $6^{th}$ position from the N-terminus of GWTHPMFEQKG (SEQ ID NO:2) (i.e., the position of the amino acid Met) results in a change in signal corresponding to an interaction between the second control peptide and the streptavidin receptor. Moreover, the change of signal is distinguishable relative to the signal produced from the interaction between the streptavidin receptor and the second control peptide in terms of both raw signal (FIG. 8A) and signal relative to a control peptide with the Met→Ala substitution (FIG. 8B). Notably, a control peptide including GWTHPMFEQKG (SEQ ID NO:2) results in an average raw signal of 18,000 units, a control peptide including GWTHPMFEQKG (SEQ ID NO:2) with a Met→Gln substitution results in an average raw signal of 48,000, and alternative substitutions and deletions for the amino acid Met at the $6^{th}$ position from the N-terminus result in an average raw signal of about 0 units. Accordingly a control peptide including GWTHPMFEQKG (SEQ ID NO:2) is useful for distinguishing the fidelity of incorporation of each of the amino acids Met and Gln from each other in addition to each of the other amino acids.

Figure 8C:
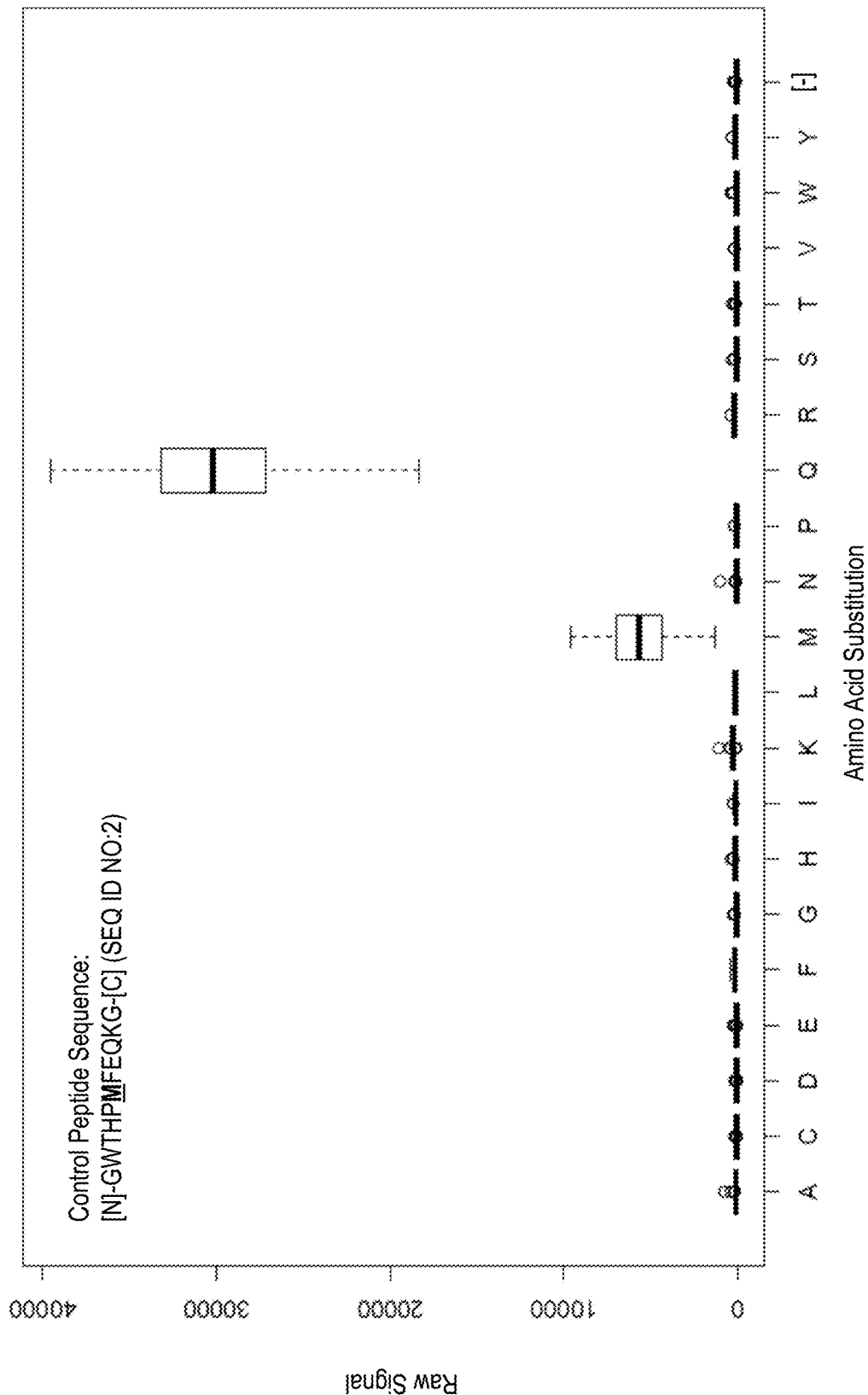
FIG. 8C is another example profile of raw fluorescence signal for the control peptide of FIG. 8A. Sequences comprising each possible amino acid substitution and deletion for the Met at the $6^{th}$ position from the N-terminus were analyzed as indicated along the horizontal axis. The illustrated control peptide sequence can be used to assess incorporation of the amino acids Met and Gln.
Figure 8D:
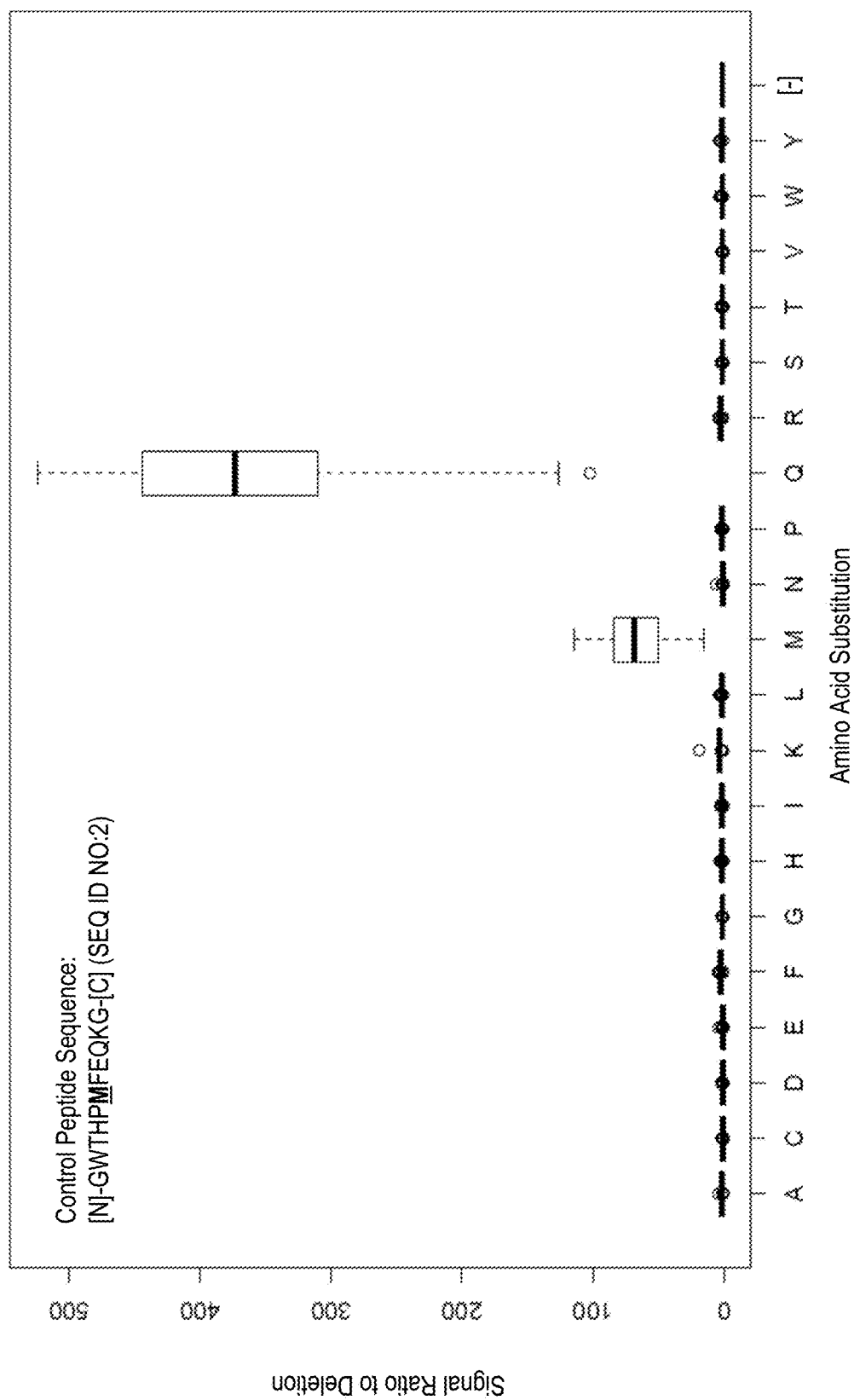
FIG. 8D is a profile of fluorescence signal ratio with respect to a deletion of the amino acid Met at the $6^{th}$ position from the N-terminus for the control peptide of FIG. 8C. Sequences comprising each possible amino acid substitution and deletion for the Met at the $6^{th}$ position from the N-terminus were analyzed as indicated along the horizontal axis.
Figure 9A:
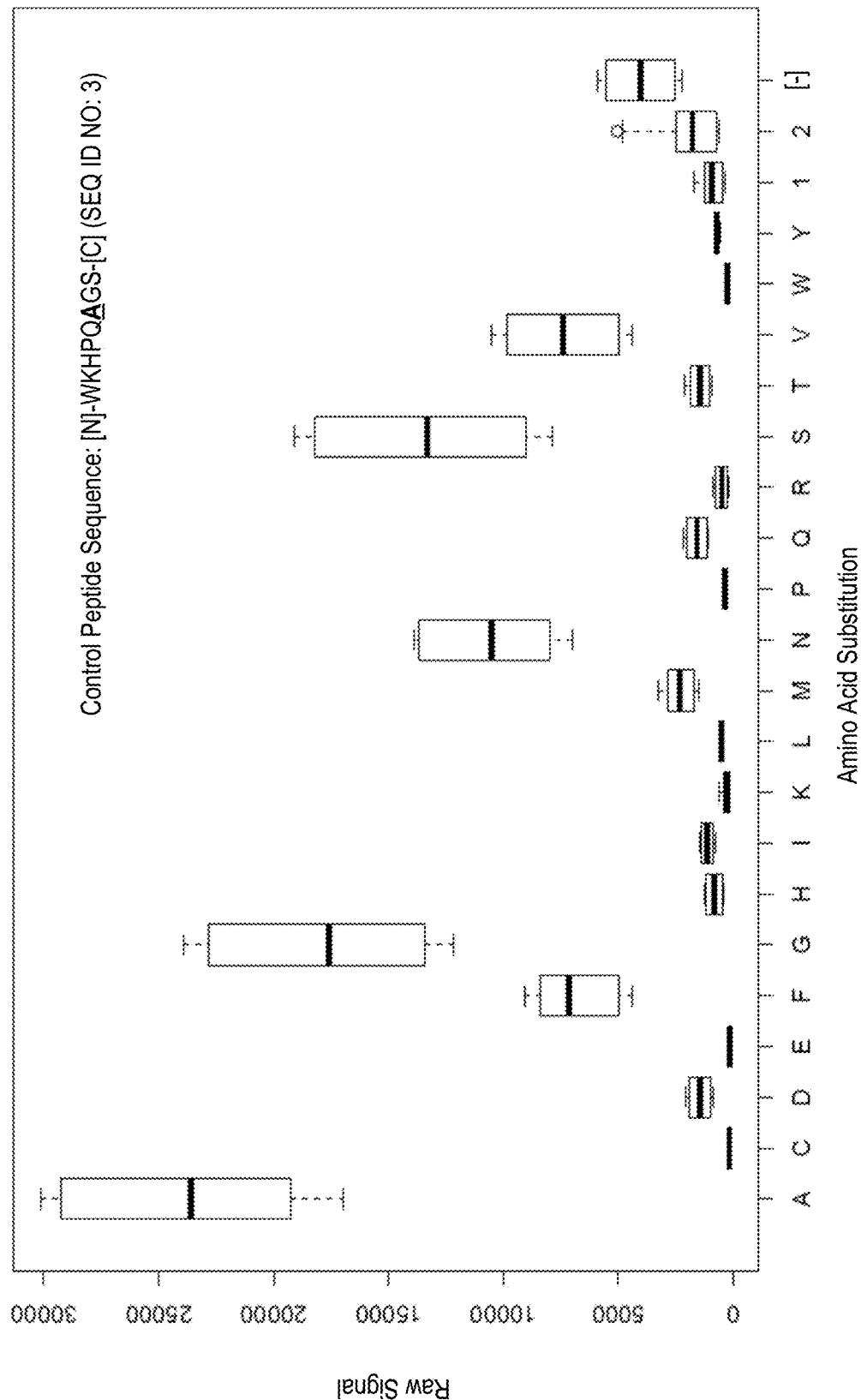
FIG. 9A is a profile of raw fluorescence signal for a control peptide having the sequence [N]-WKHPQAGS-[C] (SEQ ID NO:3). Sequences comprising each possible amino acid substitution and deletion for the Ala at the $6^{th}$ position from the N-terminus were analyzed as indicated along the horizontal axis. The illustrated control peptide sequence can be used to assess incorporation of the amino acid Ala.
Figure 9B:
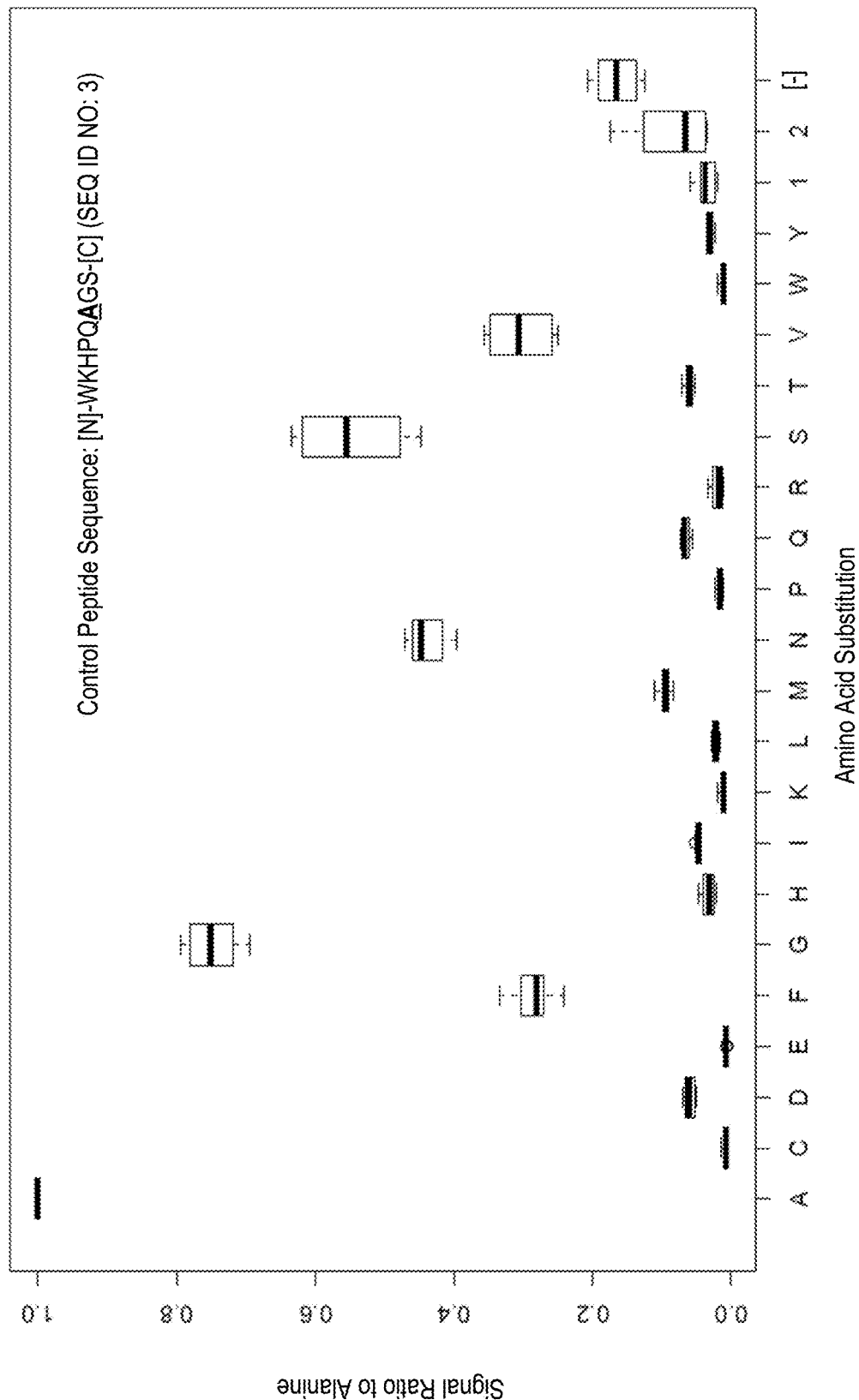
FIG. 9B is a profile of fluorescence signal ratio with respect to alanine for the control peptide of FIG. 9A. Sequences comprising each possible amino acid substitution and deletion for the Ala at the $6^{th}$ position from the N-terminus were analyzed as indicated along the horizontal axis.
Figure 10A:
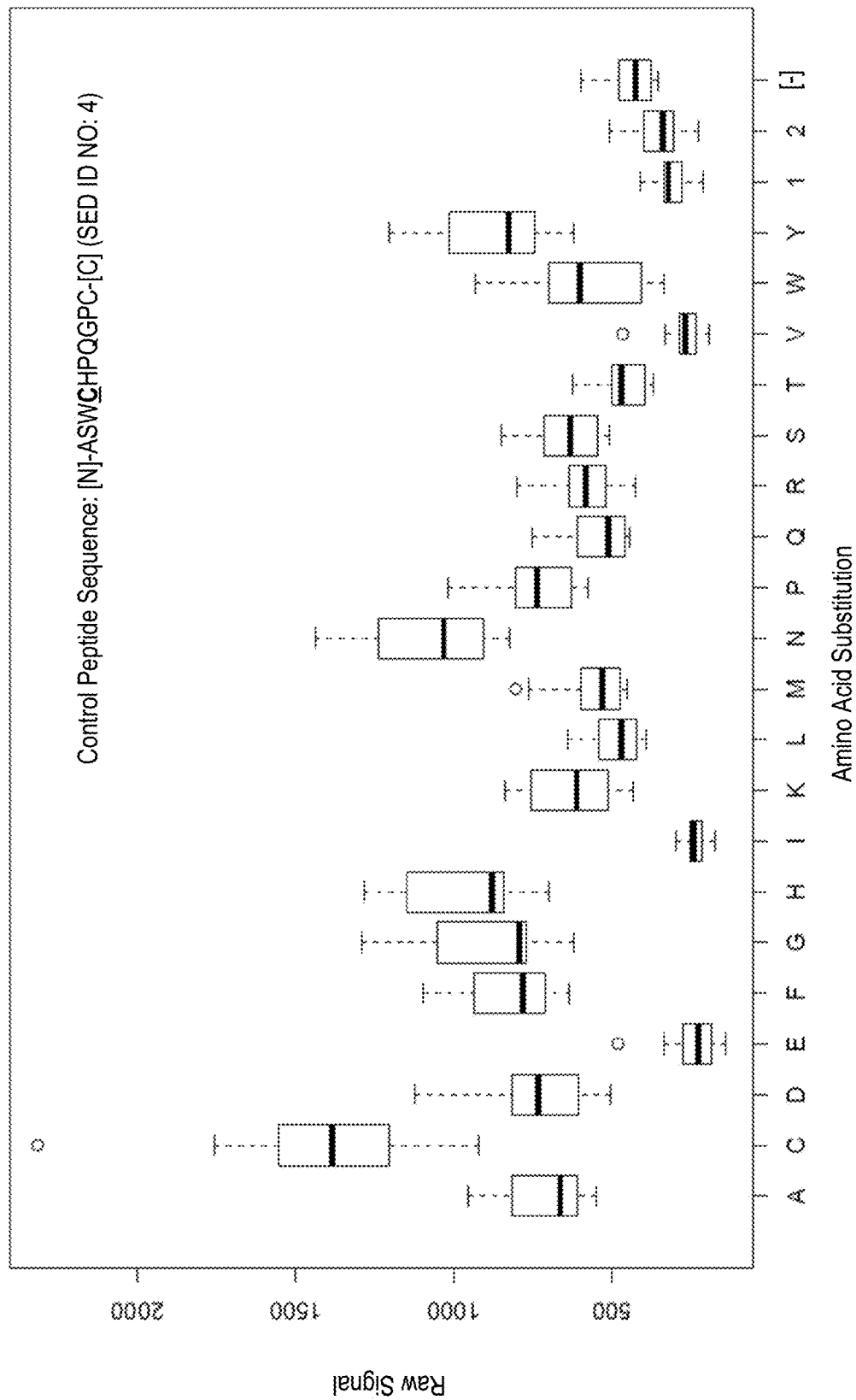
FIG. 10A is a profile of raw fluorescence signal for a control peptide having the sequence [N]-ASWCHPQGPC-[C] (SEQ ID NO:4). Sequences comprising each possible amino acid substitution and deletion for the Cys at the $4^{th}$ position from the N-terminus were analyzed as indicated along the horizontal axis. The illustrated control peptide sequence can be used to assess incorporation of the amino acid Cys.
Figure 10B:
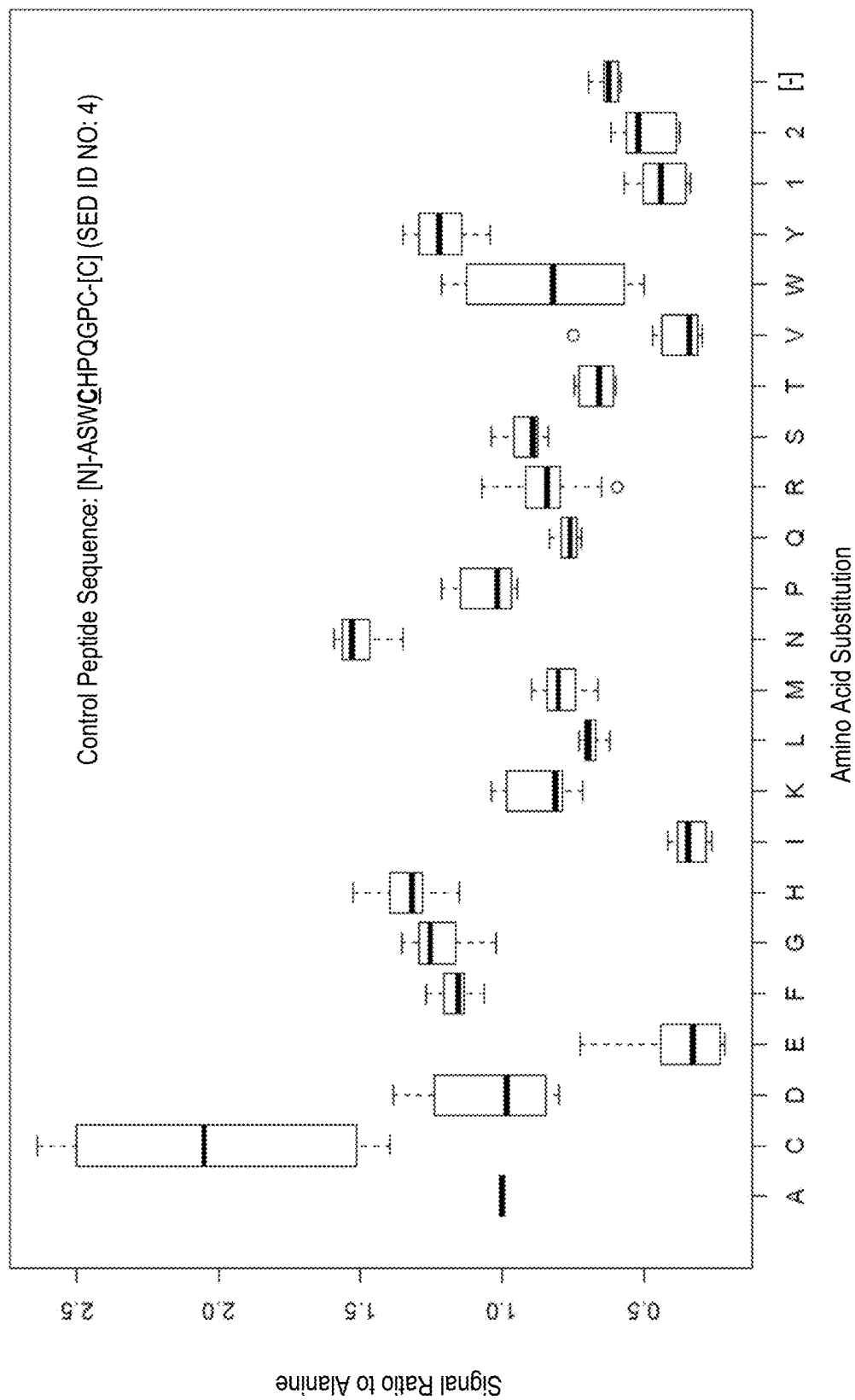
FIG. 10B is a profile of fluorescence signal ratio with respect to alanine for the control peptide of FIG. 10A. Sequences comprising each possible amino acid substitution and deletion for the Cys at the $4^{th}$ position from the N-terminus were analyzed as indicated along the horizontal axis.
Figure 11A:
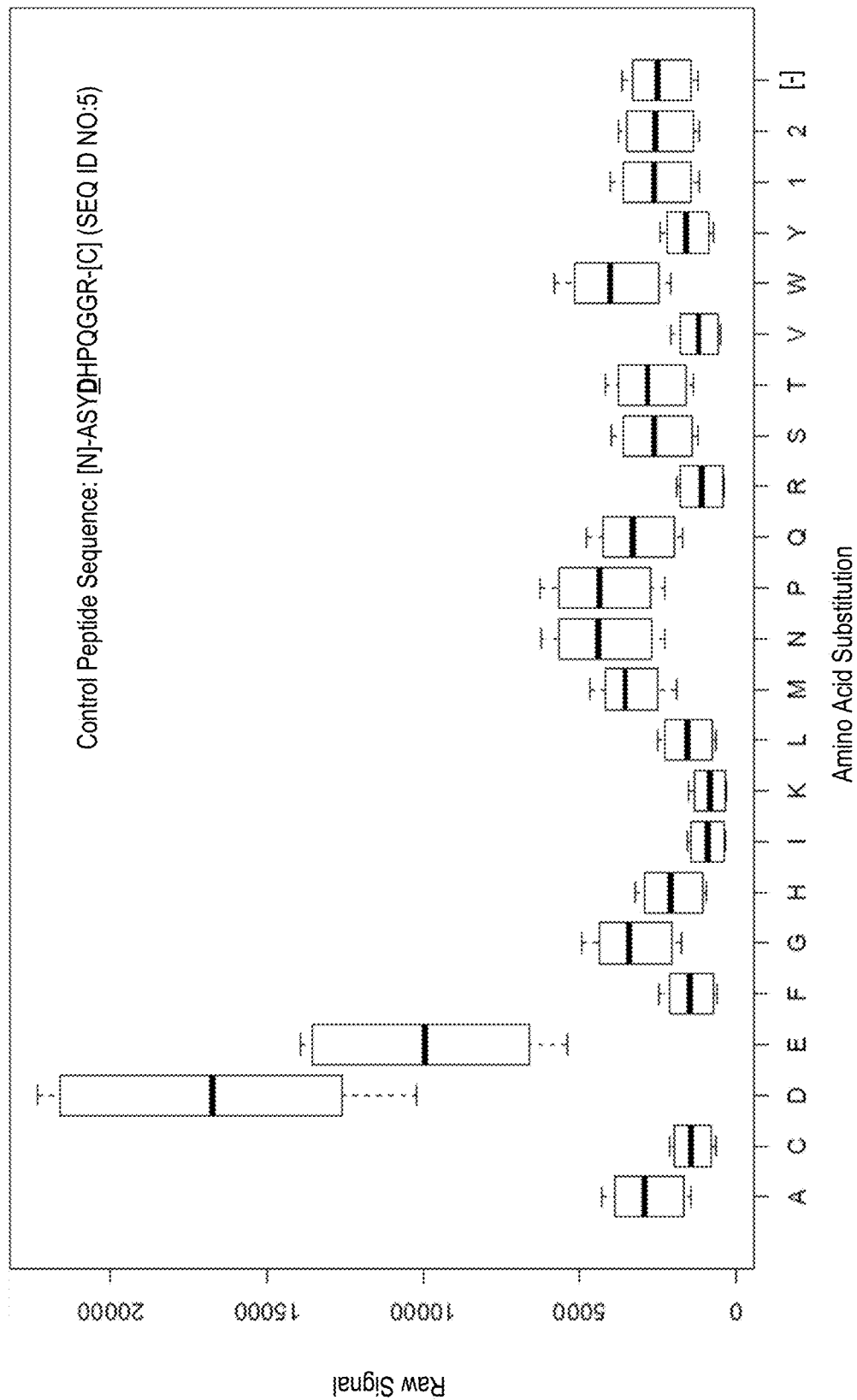
FIG. 11A is a profile of raw fluorescence signal for a control peptide having the sequence [N]-ASYDHPQGGR-[C] (SEQ ID NO:5). Sequences comprising each possible amino acid substitution and deletion for the Asp at the $4^{th}$ position from the N-terminus were analyzed as indicated along the horizontal axis. The illustrated control peptide sequence can be used to assess incorporation of the amino acids Asp and Glu.
Figure 11B:
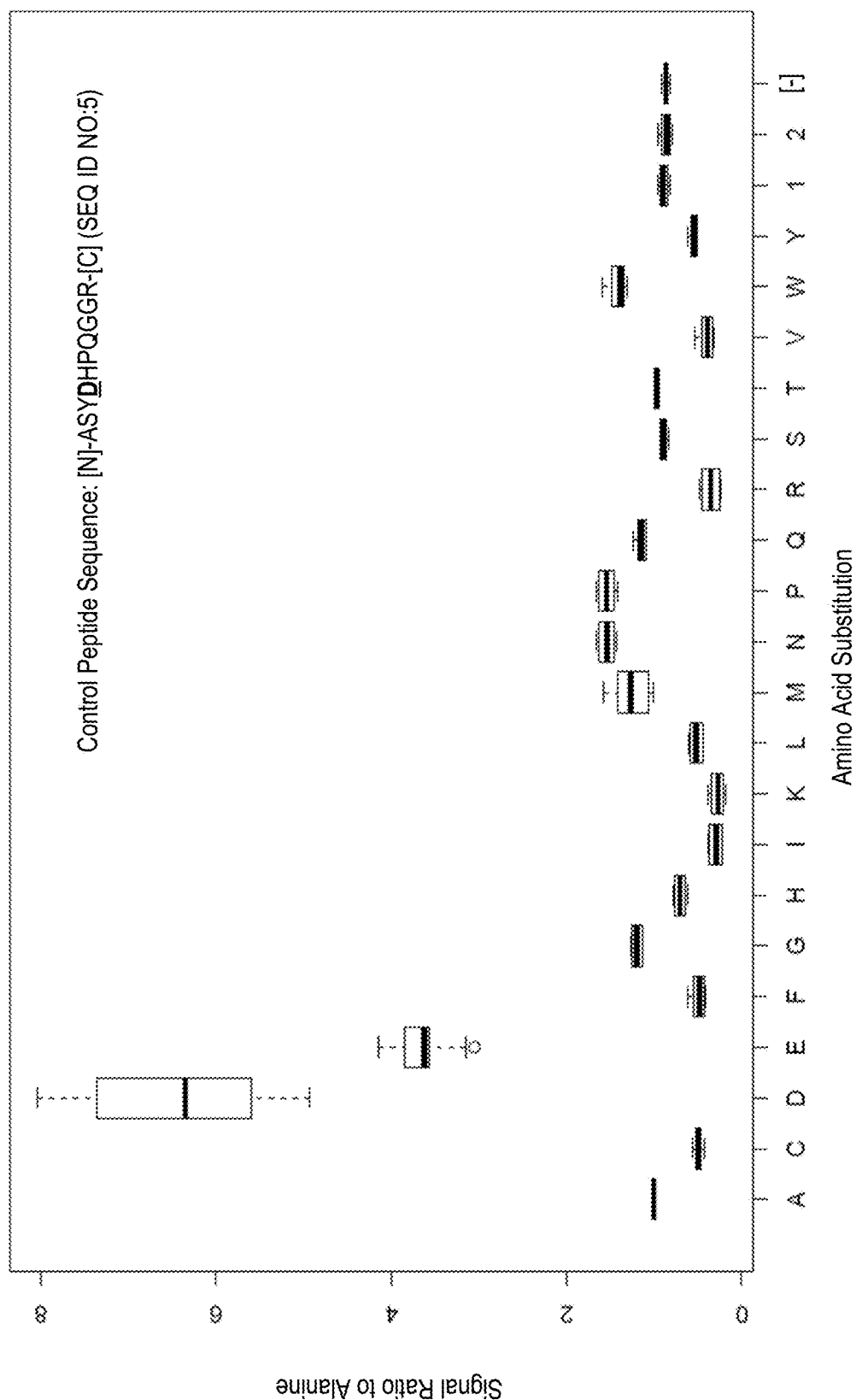
FIG. 11B is a profile of fluorescence signal ratio with respect to alanine for the control peptide of FIG. 11A. Sequences comprising each possible amino acid substitution and deletion for the Asp at the $4^{th}$ position from the N-terminus were analyzed as indicated along the horizontal axis.
Figure 12A:
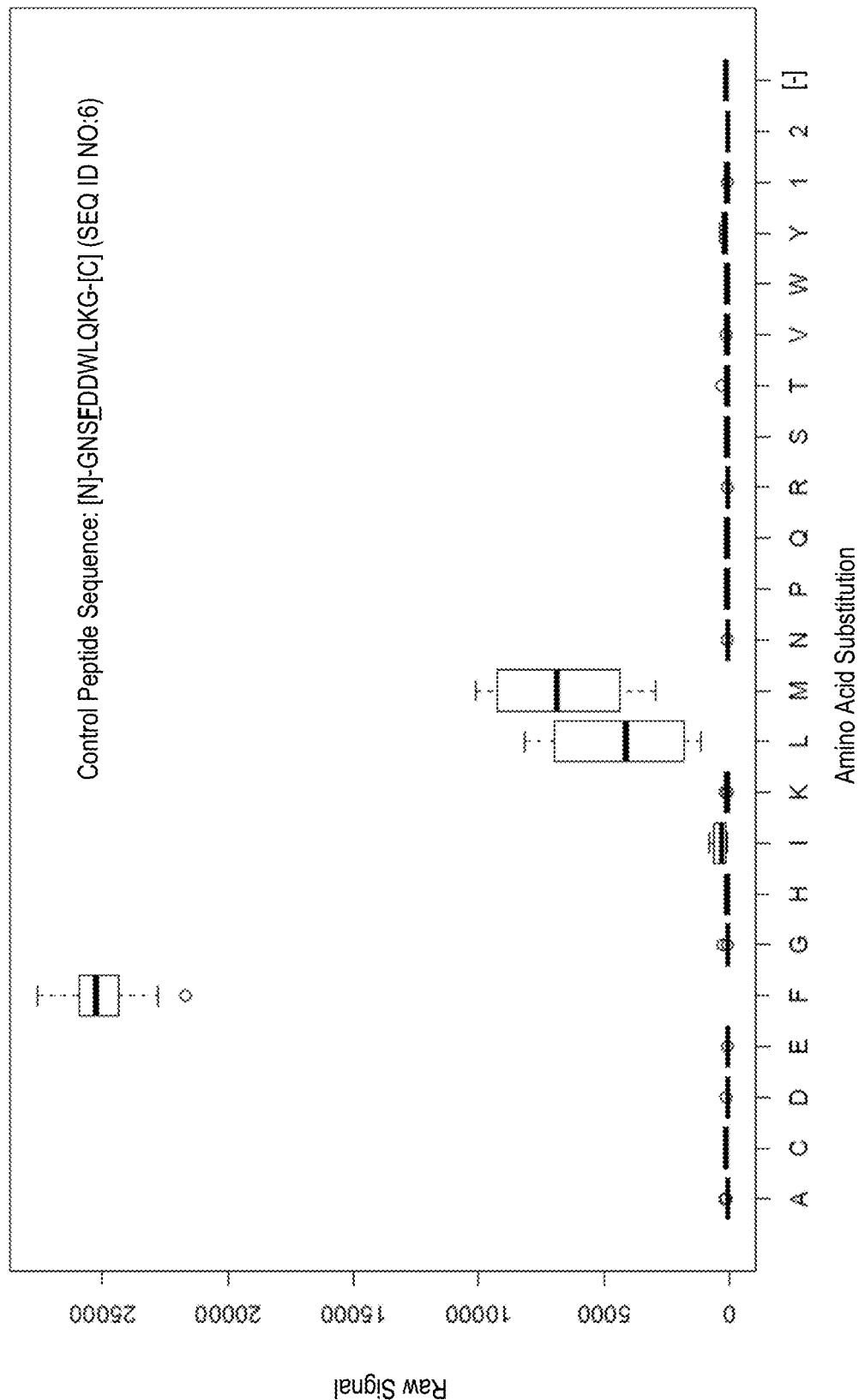
FIG. 12A is a profile of raw fluorescence signal for a control peptide having the sequence [N]-GNSFD-DWLQKG-[C] (SEQ ID NO:6). Sequences comprising each possible amino acid substitution and deletion for the Phe at the $4^{th}$ position from the N-terminus were analyzed as indicated along the horizontal axis. The illustrated control peptide sequence can be used to assess incorporation of the amino acid Phe.
Figure 12B:
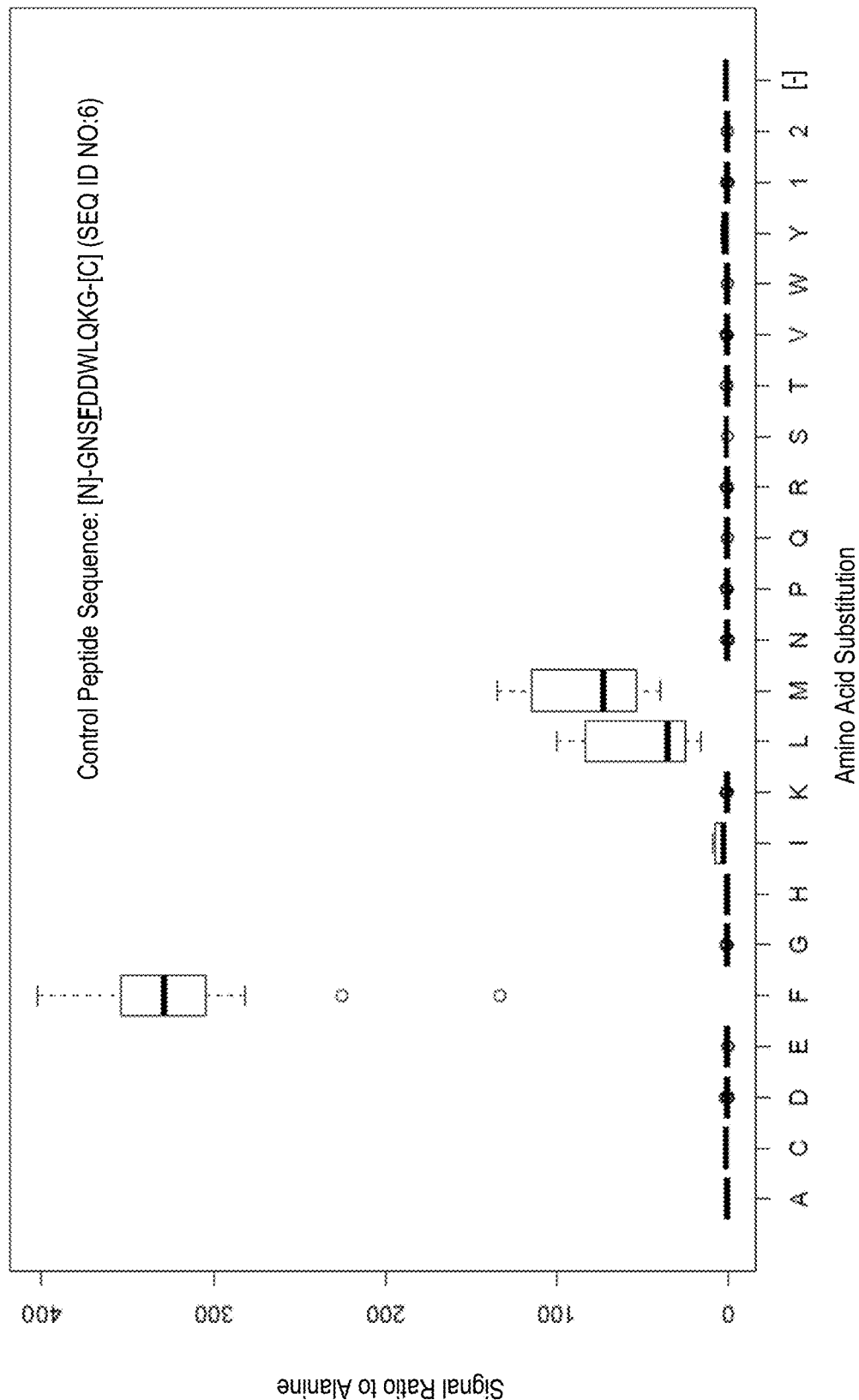
FIG. 12B is a profile of fluorescence signal ratio with respect to alanine for the control peptide of FIG. 12A. Sequences comprising each possible amino acid substitution and deletion for the Phe at the $4^{th}$ position from the N-terminus were analyzed as indicated along the horizontal axis.
Figure 13A:
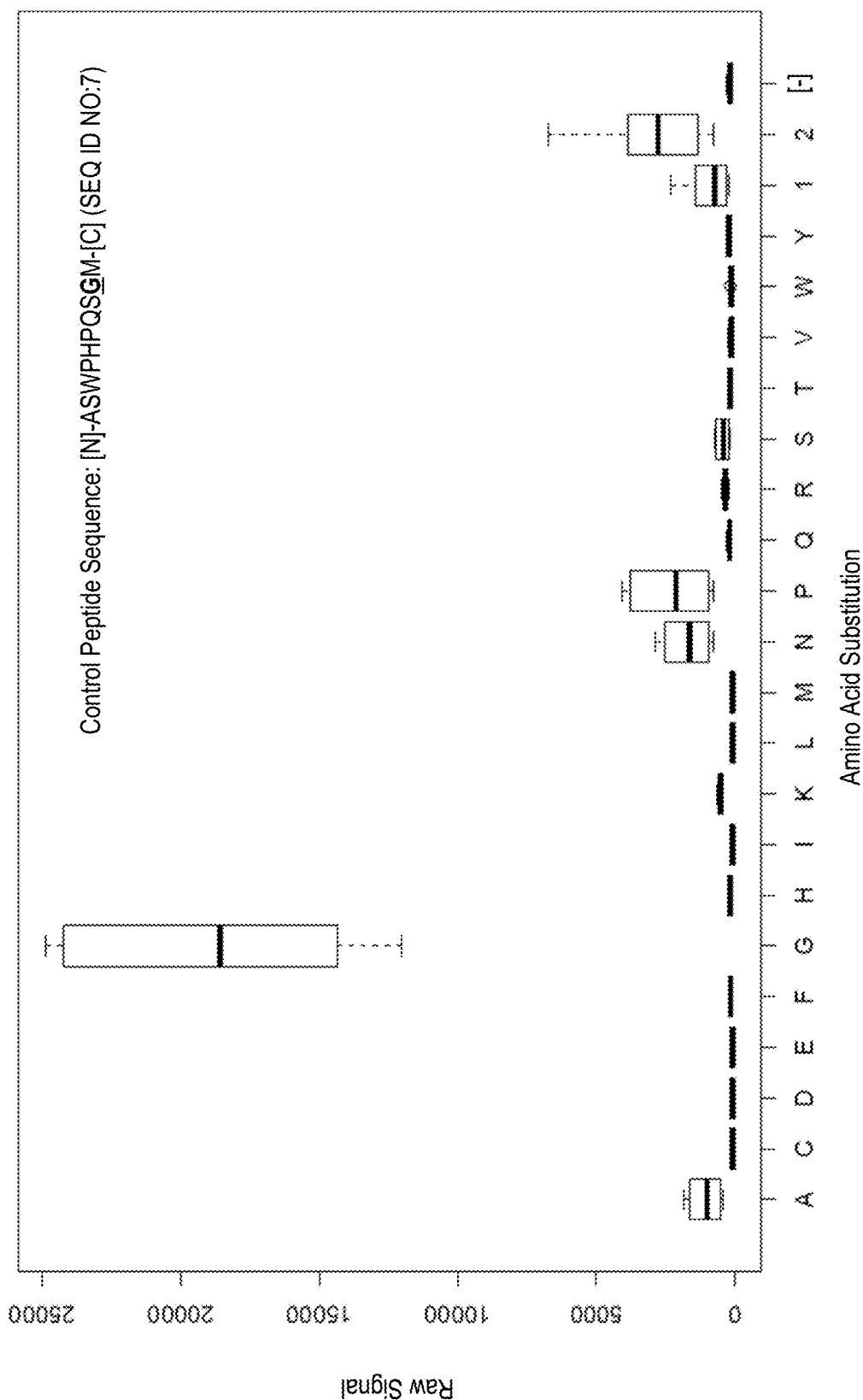
FIG. 13A is a profile of raw fluorescence signal for a control peptide having the sequence [N]-ASWPHPQSGM-[C] (SEQ ID NO:7). Sequences comprising each possible amino acid substitution and deletion for the Gly at the $9^{th}$ position from the N-terminus were analyzed as indicated along the horizontal axis. The illustrated control peptide sequence can be used to assess incorporation of the amino acid Gly.
Figure 13B:
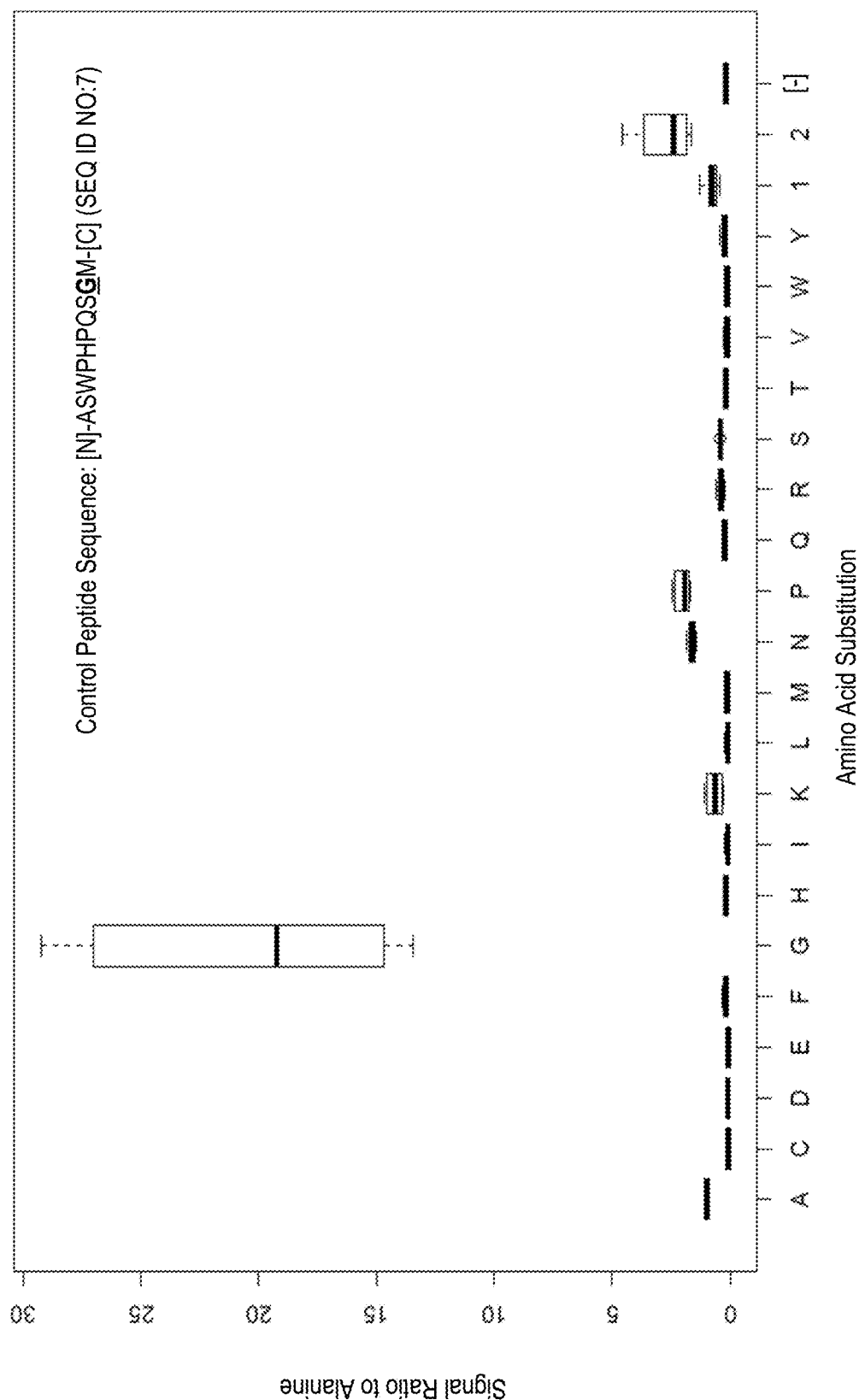
FIG. 13B is a profile of fluorescence signal ratio with respect to alanine for the control peptide of FIG. 13A. Sequences comprising each possible amino acid substitution and deletion for the Gly at the $9^{th}$ position from the N-terminus were analyzed as indicated along the horizontal axis.
Figure 14A:
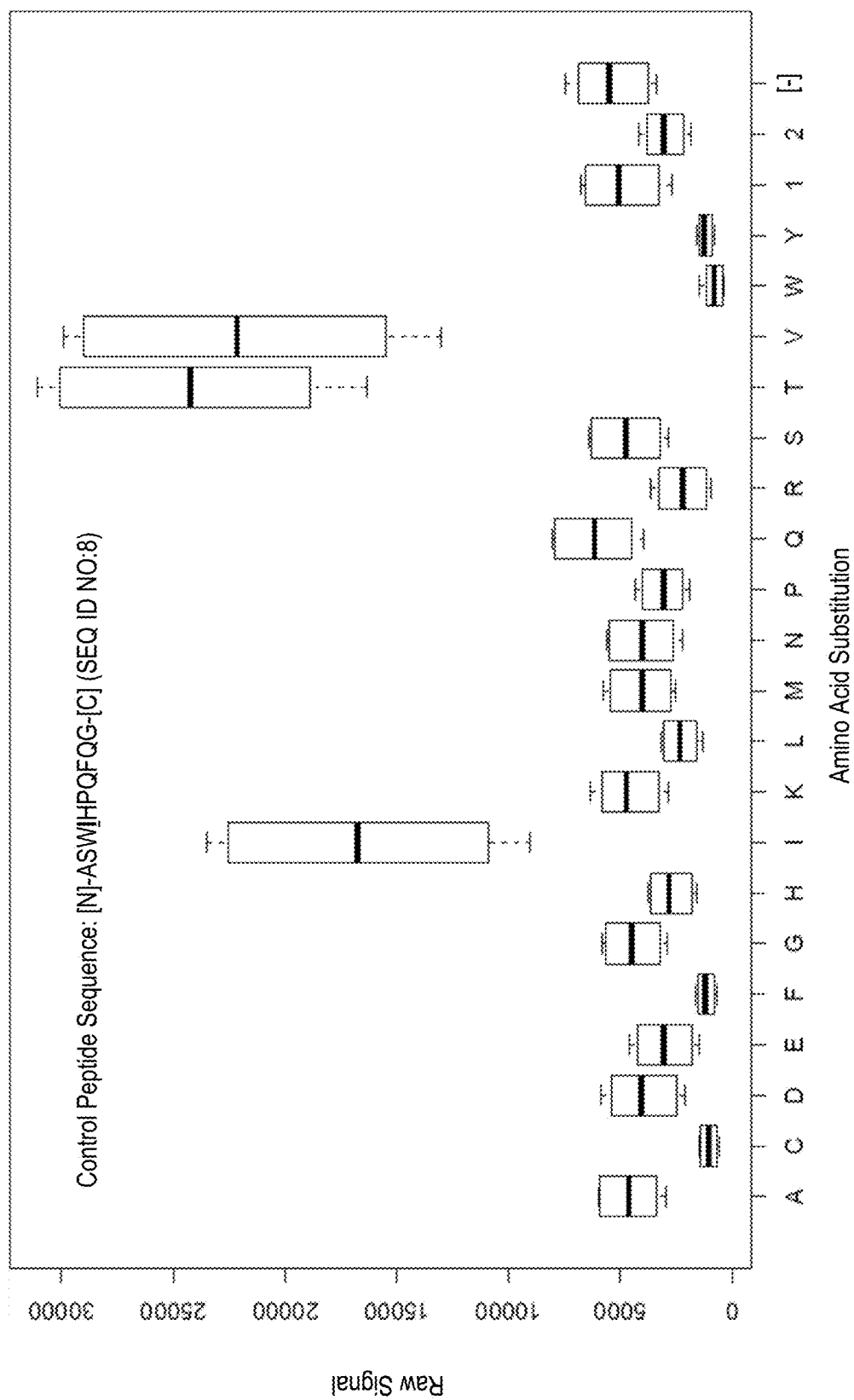
FIG. 14A is a profile of raw fluorescence signal for a control peptide having the sequence [N]-ASWIHPQFQG-[C] (SEQ ID NO:8). Sequences comprising each possible amino acid substitution and deletion for the Val at the $4^{th}$ position from the N-terminus were analyzed as indicated along the horizontal axis. The illustrated control peptide sequence can be used to assess incorporation of the amino acids Thr and Val.
Figure 14B:
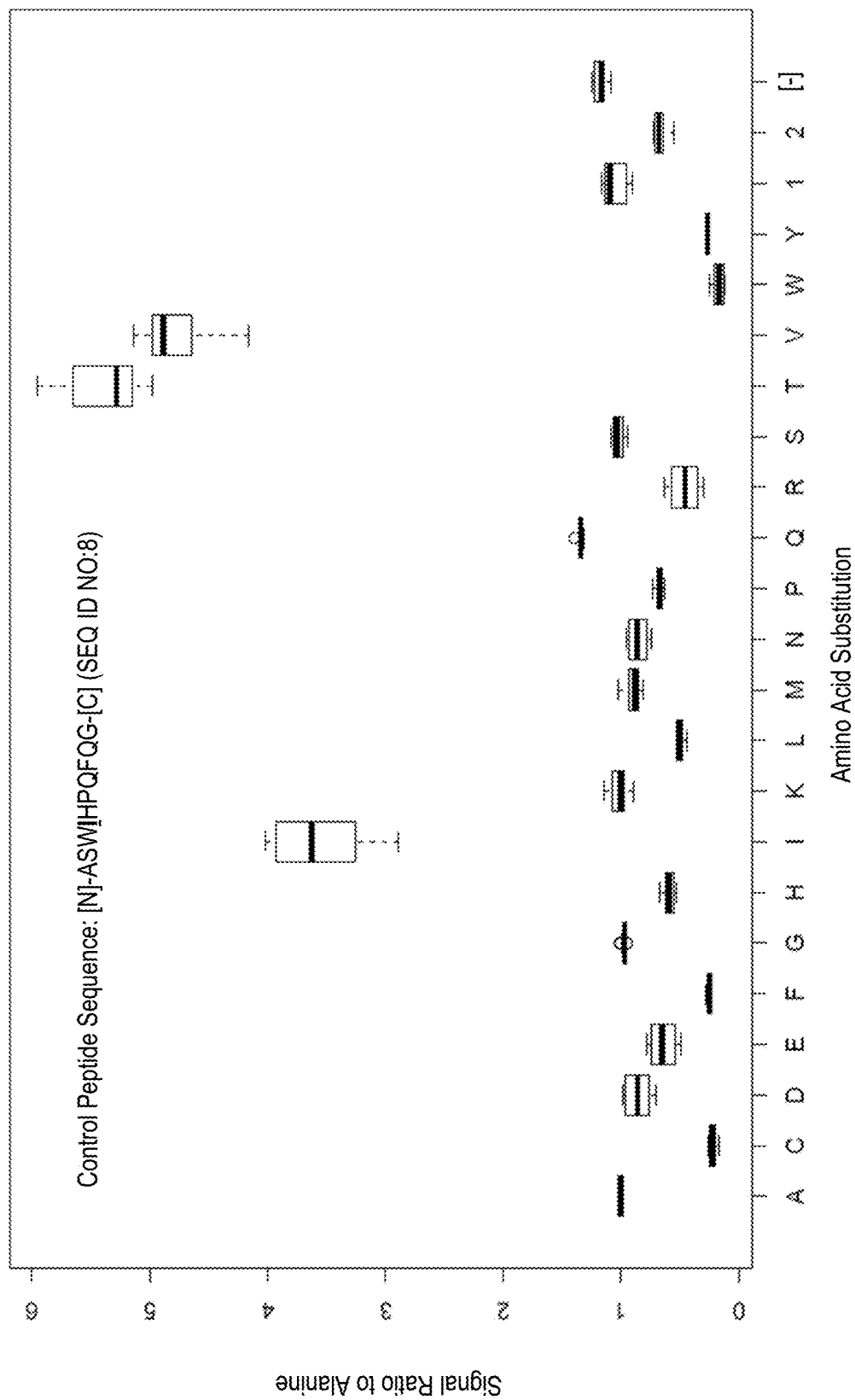
FIG. 14B is a profile of fluorescence signal ratio with respect to alanine for the control peptide of FIG. 14A. Sequences comprising each possible amino acid substitution and deletion for the Val at the $4^{th}$ position from the N-terminus were analyzed as indicated along the horizontal axis.
Figure 15A:
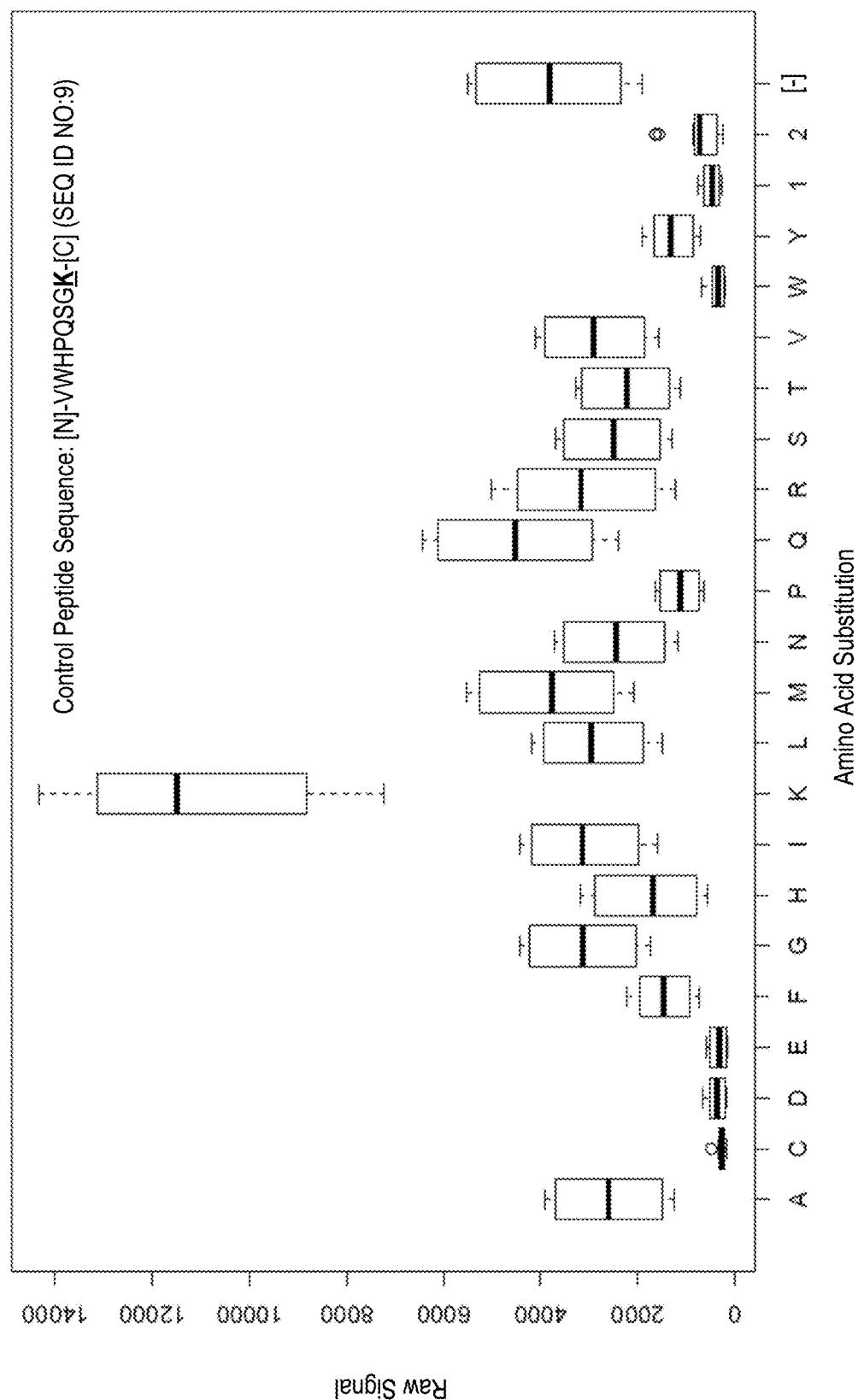
FIG. 15A is a profile of raw fluorescence signal for a control peptide having the sequence [N]-VWHPQSGK-[C] (SEQ ID NO:9). Sequences comprising each possible amino acid substitution and deletion for the Lys at the 8$^{th}$ position from the N-terminus were analyzed as indicated along the horizontal axis. The illustrated control peptide sequence can be used to assess incorporation of the amino acid Lys.
Figure 15B:
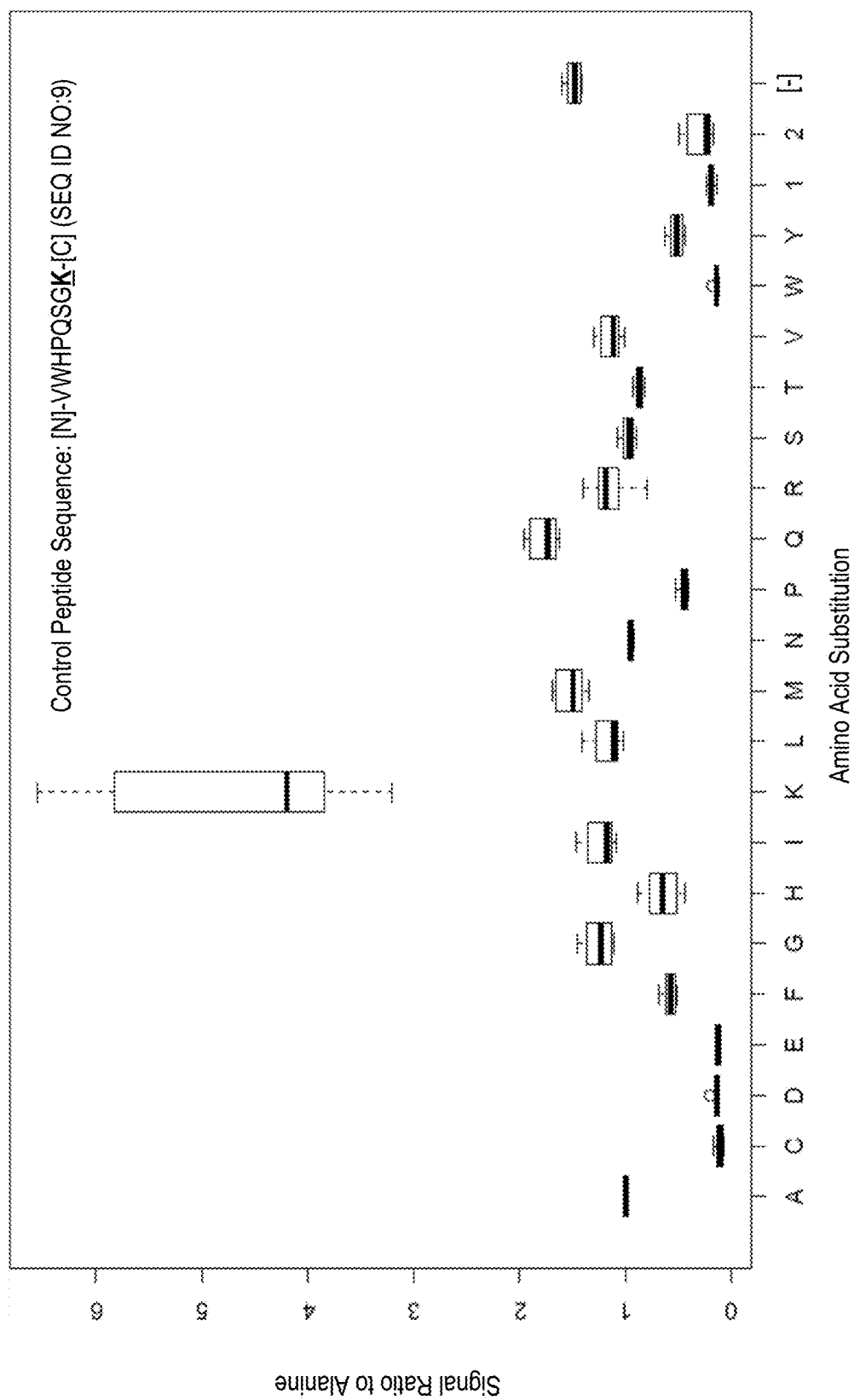
FIG. 15B is a profile of fluorescence signal ratio with respect to alanine for the control peptide of FIG. 15A. Sequences comprising each possible amino acid substitution and deletion for the Lys at the 8$^{th}$ position from the N-terminus were analyzed as indicated along the horizontal axis.
Figure 16A:
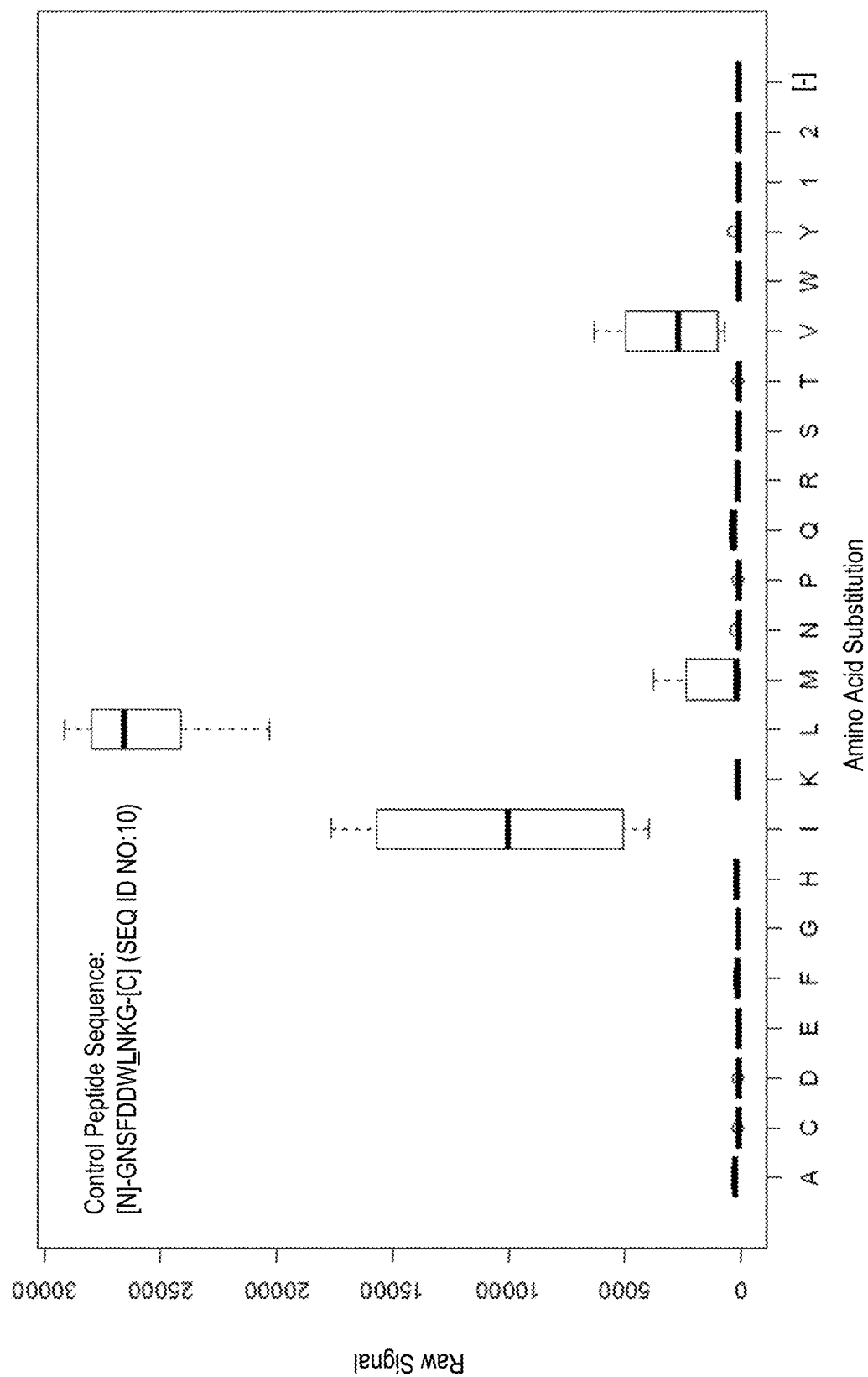
FIG. 16A is a profile of raw fluorescence signal for a control peptide having the sequence [N]-GNSFD-DWLNKG-[C] (SEQ ID NO:10). Sequences comprising each possible amino acid substitution and deletion for the Leu at the 8$^{th}$ position from the N-terminus were analyzed as indicated along the horizontal axis. The illustrated control peptide sequence can be used to assess incorporation of the amino acids Leu and Ile.
Figure 16B:
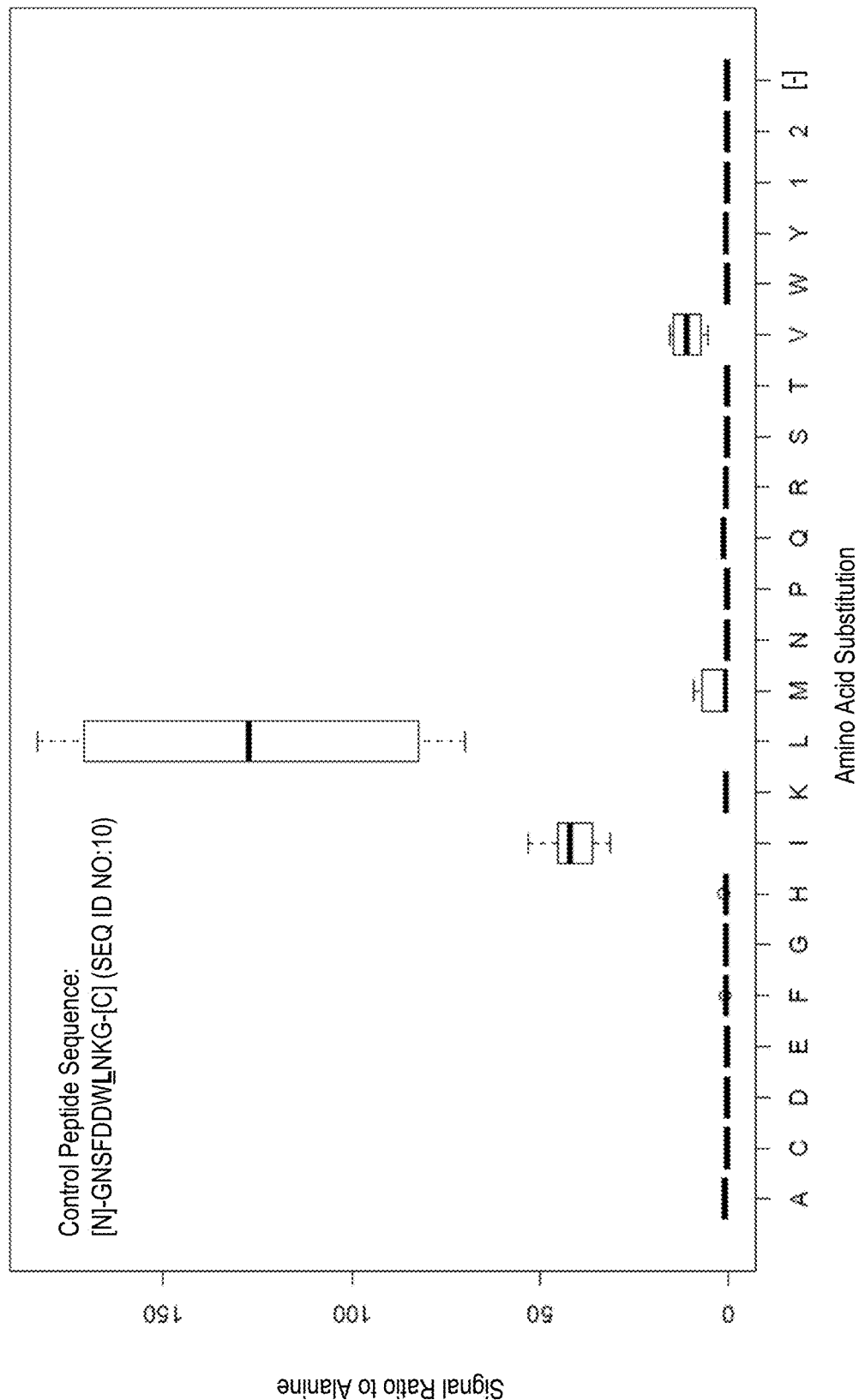
FIG. 16B is a profile of fluorescence signal ratio with respect to alanine for the control peptide of FIG. 16A. Sequences comprising each possible amino acid substitution and deletion for the Leu at the 8$^{th}$ position from the N-terminus were analyzed as indicated along the horizontal axis.
Figure 17A:
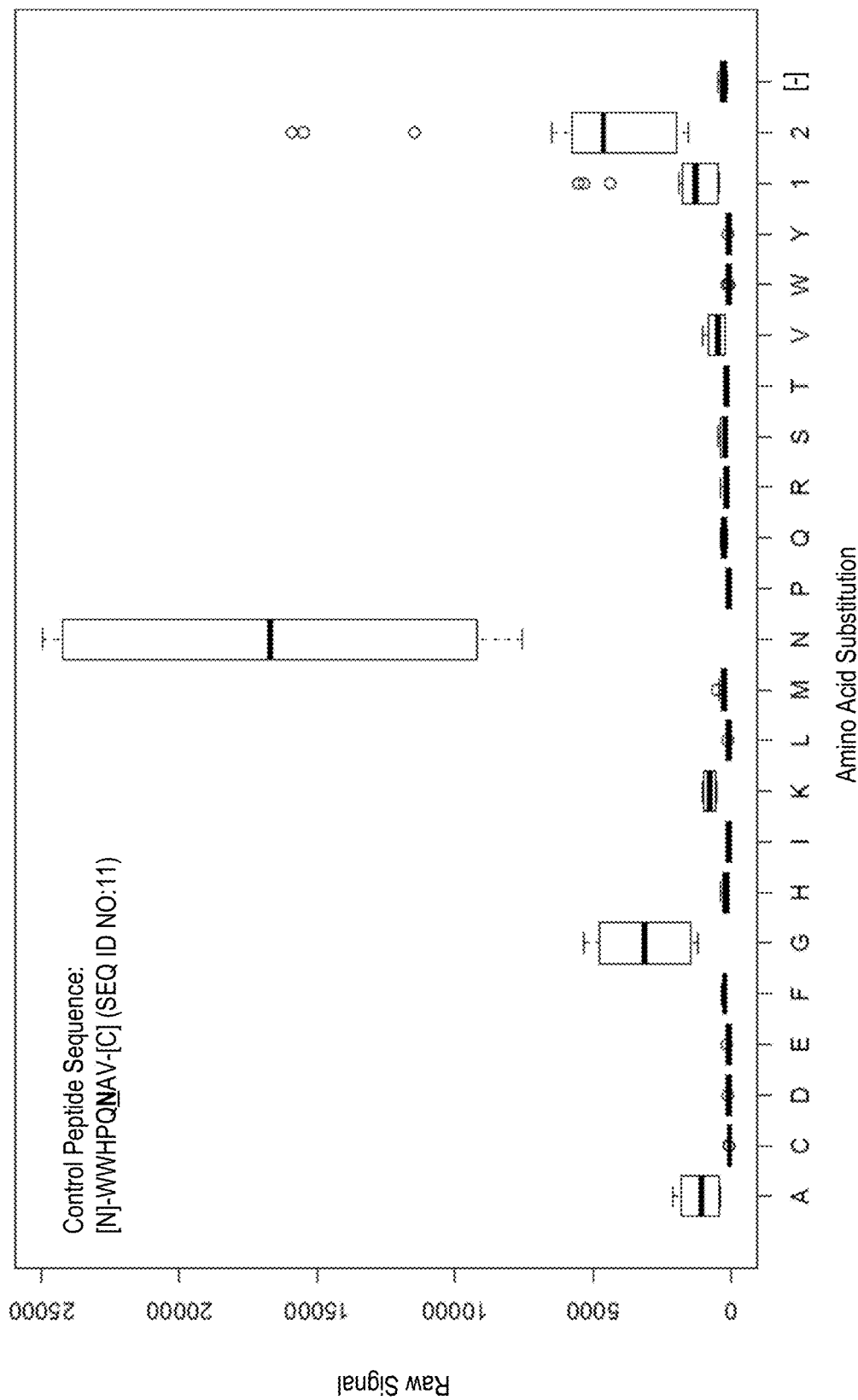
FIG. 17A is a profile of raw fluorescence signal for a control peptide having the sequence [N]-WWHPQNAV-[C] (SEQ ID NO:11). Sequences comprising each possible amino acid substitution and deletion for the Asn at the 6$^{th}$ position from the N-terminus were analyzed as indicated along the horizontal axis. The illustrated control peptide sequence can be used to assess incorporation of the amino acid Asn.
Figure 17B:
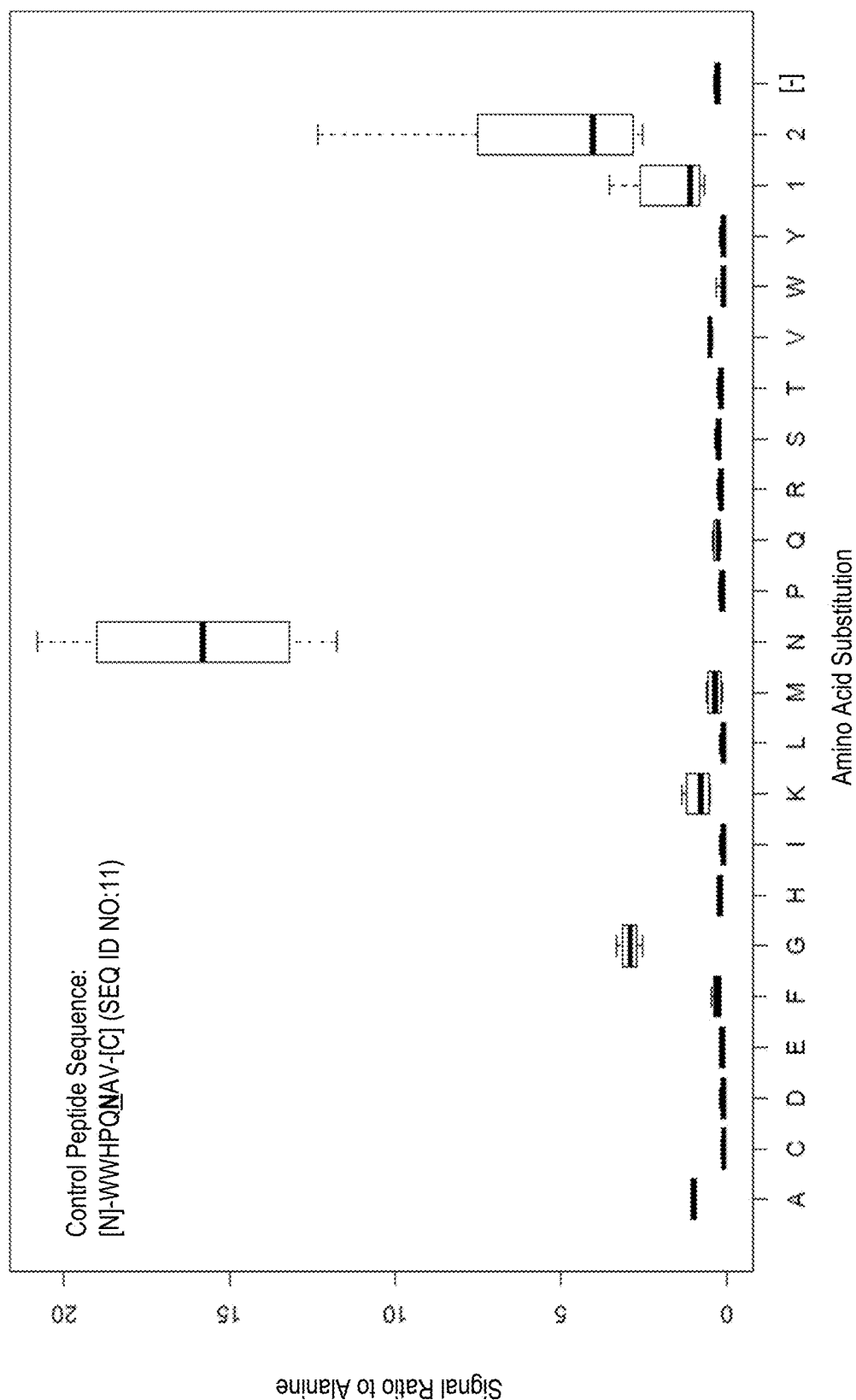
FIG. 17B is a profile of fluorescence signal ratio with respect to alanine for the control peptide of FIG. 17A. Sequences comprising each possible amino acid substitution and deletion for the Asn at the 6$^{th}$ position from the N-terminus were analyzed as indicated along the horizontal axis.
Figure 18A:
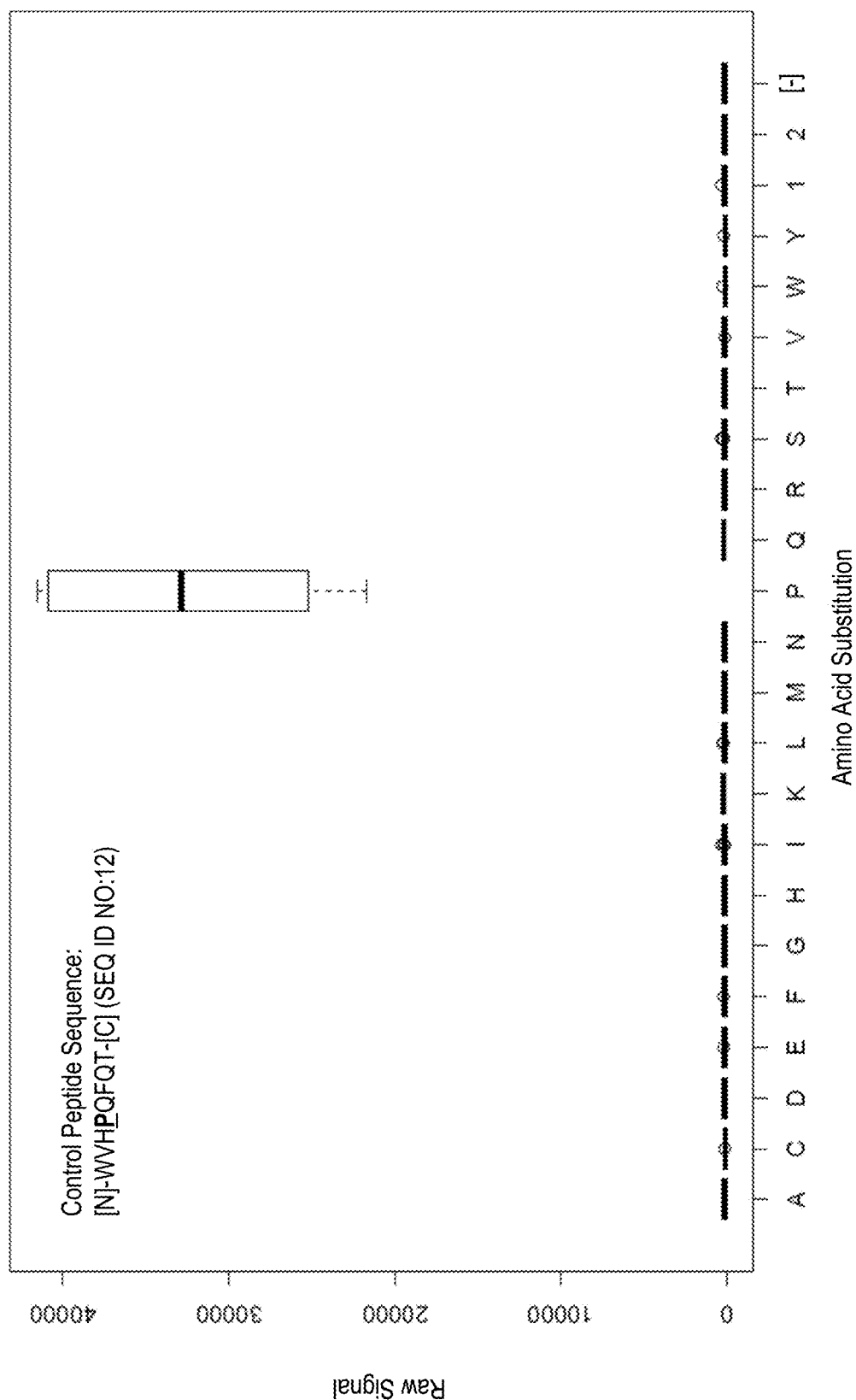
FIG. 18A is a profile of raw fluorescence signal for a control peptide having the sequence [N]-WVHPQFQT-[C] (SEQ ID NO:12). Sequences comprising each possible amino acid substitution and deletion for the Pro at the 4$^{th}$ position from the N-terminus were analyzed as indicated along the horizontal axis. The illustrated control peptide sequence can be used to assess incorporation of the amino acid Pro.
Figure 18B:
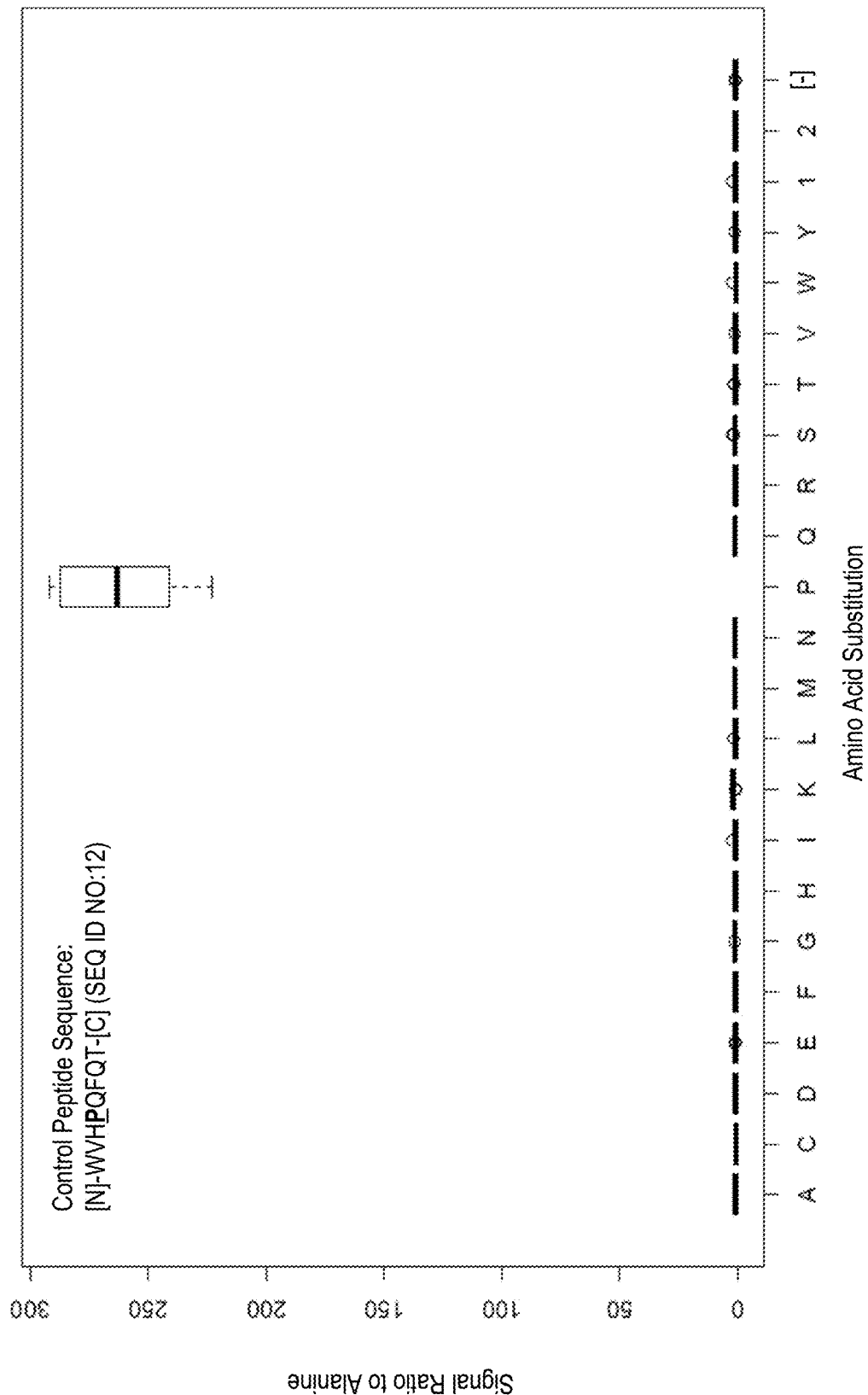
FIG. 18B is a profile of fluorescence signal ratio with respect to alanine for the control peptide of FIG. 18A. Sequences comprising each possible amino acid substitution and deletion for the Pro at the 4$^{th}$ position from the N-terminus were analyzed as indicated along the horizontal axis.

It will be appreciated that while a plot of relative signal can be prepared with respect to an alanine substitution peptide (e.g., FIGS. 7B and 8B), any other substitution sequence, deletion sequence, or other like sequence may be used to prepare a plot of relative signal for determining synthesis fidelity. For example, FIGS. 8C and 8D illustrate data collected for a set of control peptides based on GWTHPMFEQKG (SEQ ID NO:2) (Table 1; FIGS. 8A and 8B) that can be similarly used to identify the fidelity of incorporation of either of the amino acids Met and Gln into a synthetic population of peptides including the aforementioned control peptide. In this example, a plot of both raw fluorescence signal (FIG. 8C) and fluorescence signal relative to the deletion control peptide (indicated as [-] on the horizontal axis), where the deletion control peptide include a deletion of the amino acid Met at the $6^{th}$ position from the N-terminus.

The peptide binders specific for streptavidin (Table 1) can be used as quality control peptides for any application that is compatible with the detection or capture of streptavidin, a fragment of streptavidin, or a streptavidin-biotin. However, other peptide binders can be similarly developed for a given receptor molecule other than streptavidin.

In one example, a population of 2.88 million peptide features is synthesized on a 2.54 cm×7.62 cm array surface. Of the 2.88 million features synthesized, about 10,000 of the features comprise control peptides selected from Table 1. The control peptides are grouped into blocks that are replicated at various locations across the array surface. Each block of control peptides includes each of the 17 control peptide sequences shown in Table 1. In addition, for each one of the 17 control peptide sequences, a series of 20 corresponding peptides sequences are synthesized that includes 19 amino acid substitution sequences and 1 deletion sequence. For the example case of the control peptide sequence [N]-GFEDYLGEYHG-[C] (SEQ ID NO:1) in Table 1 and FIGS. 7A and 7B, peptide sequences are synthesized substituting the His at the $10^{th}$ position from the N-terminus for each of the 19 other canonical amino acids, as well as a deletion peptide sequence that omits the His at the $10^{th}$ position from the N terminus altogether for a total of 21 unique peptide features. Accordingly for each of the 17 control peptide sequences in Table 1, there are 21 unique peptides features synthesized within a block of control peptides for a total of 17×21 or 357 unique peptide features per block. In the present example, each of the 357 unique peptide features are arranged into a block of control peptide features that is repeated 27 times across a single array for a total of 357×27 or 9,639 total control peptide features per array of 2.88 million peptide features.

Figure 19A:
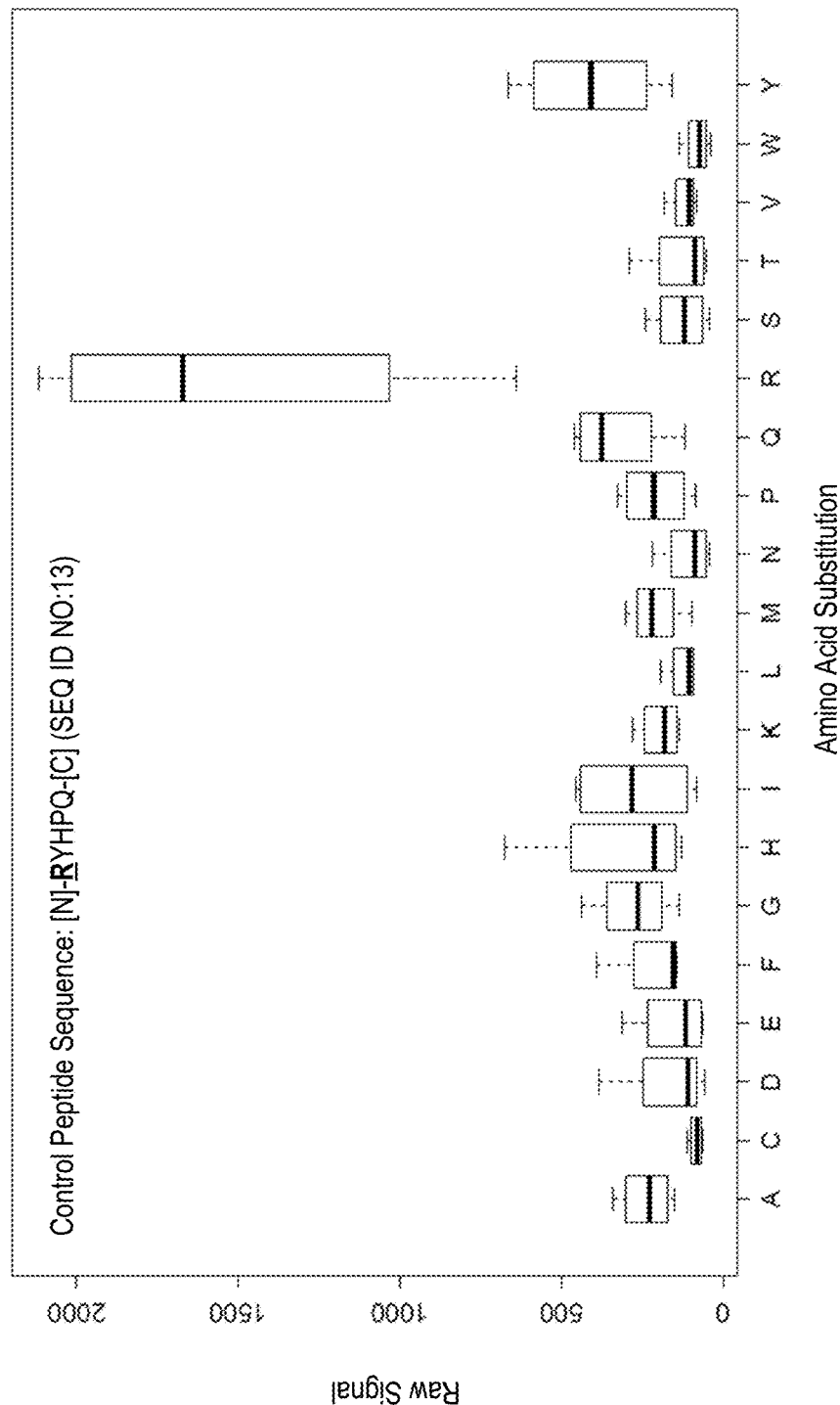
FIG. 19A is a profile of raw fluorescence signal for a control peptide having the sequence [N]-RYHPQ-[C] (SEQ ID NO:13). Sequences comprising each possible amino acid substitution and deletion for the Arg at the 1$^{st}$ position from the N-terminus were analyzed as indicated along the horizontal axis. The illustrated control peptide sequence can be used to assess incorporation of the amino acid Arg.
Figure 19B:
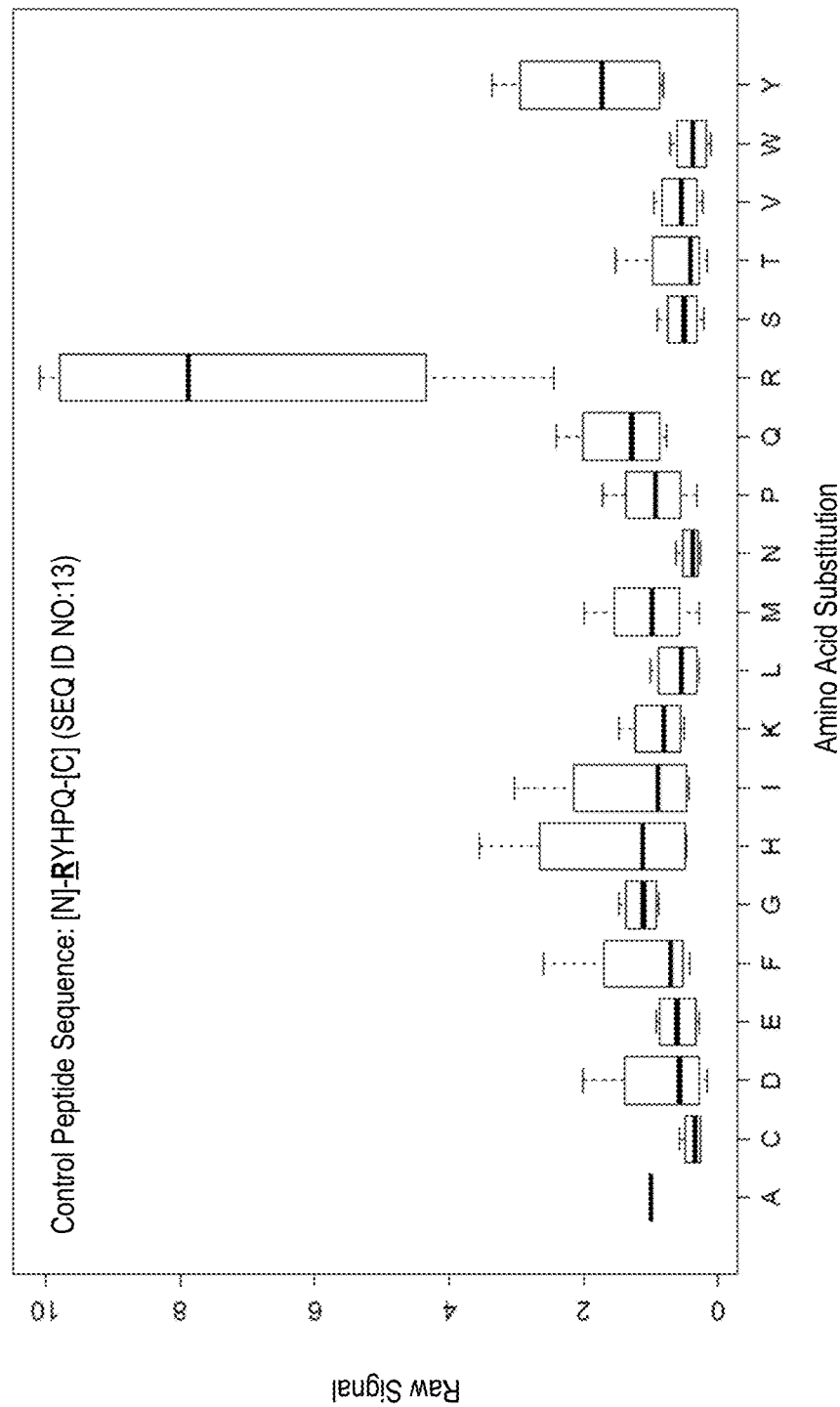
FIG. 19B is a profile of fluorescence signal ratio with respect to alanine for the control peptide of FIG. 19A. Sequences comprising each possible amino acid substitution and deletion for the Arg at the 1$^{st}$ position from the N-terminus were analyzed as indicated along the horizontal axis.
Figure 20A:
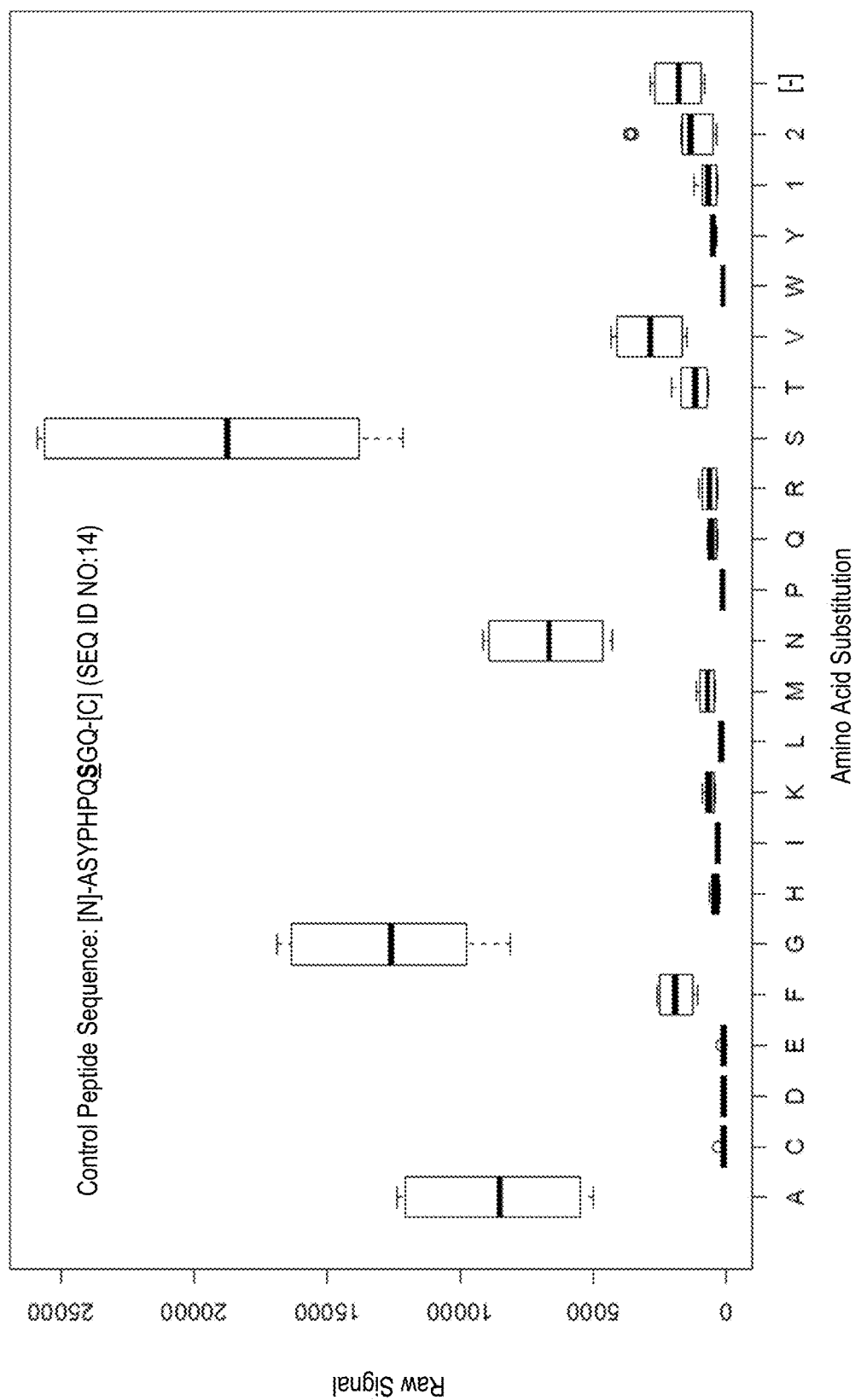
FIG. 20A is a profile of raw fluorescence signal for a control peptide having the sequence [N]-ASYPHPQSGQ-[C] (SEQ ID NO:14). Sequences comprising each possible amino acid substitution and deletion for the Ser at the 8$^{th}$ position from the N-terminus were analyzed as indicated along the horizontal axis. The illustrated control peptide sequence can be used to assess incorporation of the amino acid Ser.
Figure 20B:
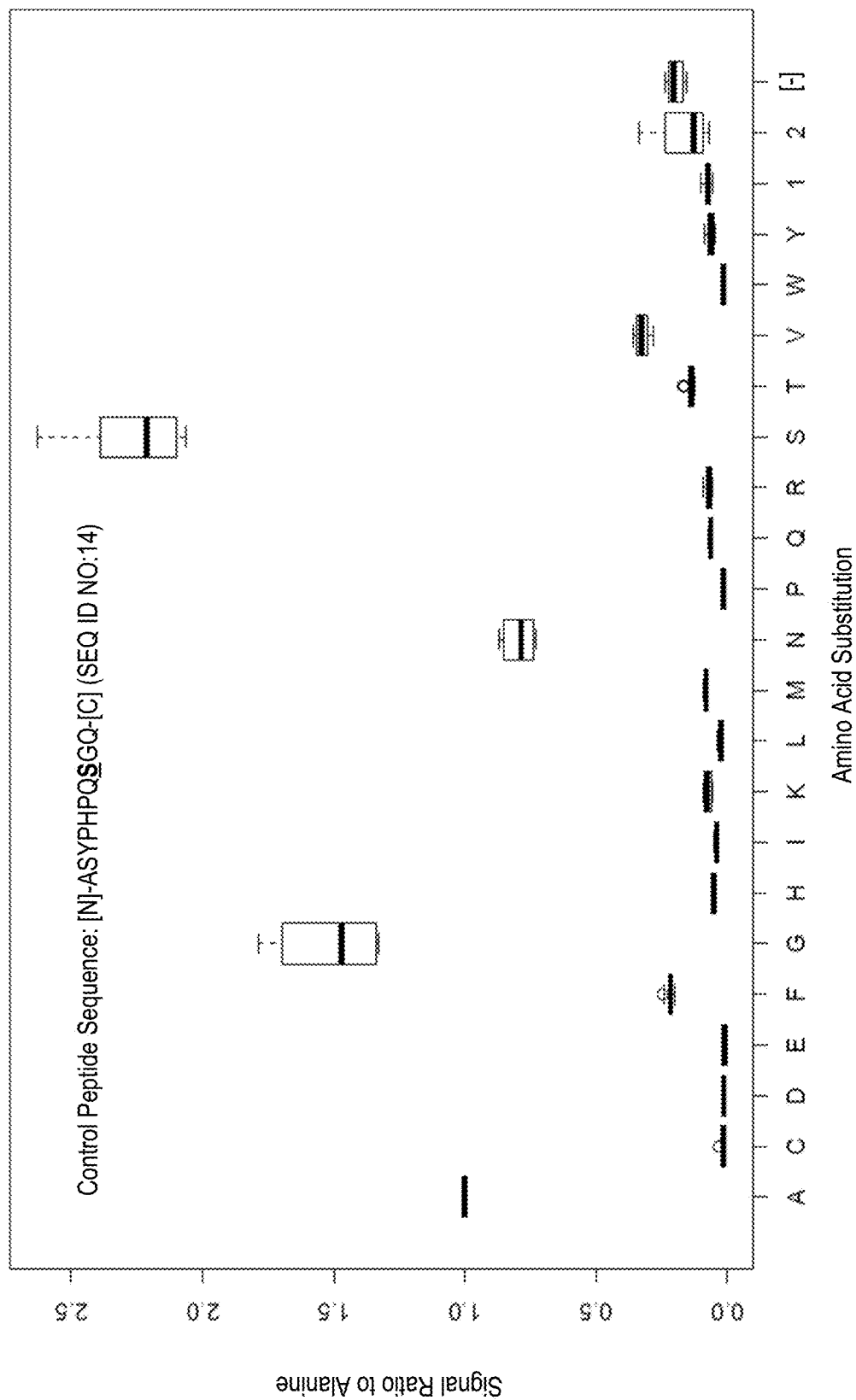
FIG. 20B is a profile of fluorescence signal ratio with respect to alanine for the control peptide of FIG. 20A. Sequences comprising each possible amino acid substitution and deletion for the Ser at the 8$^{th}$ position from the N-terminus were analyzed as indicated along the horizontal axis.
Figure 21A:
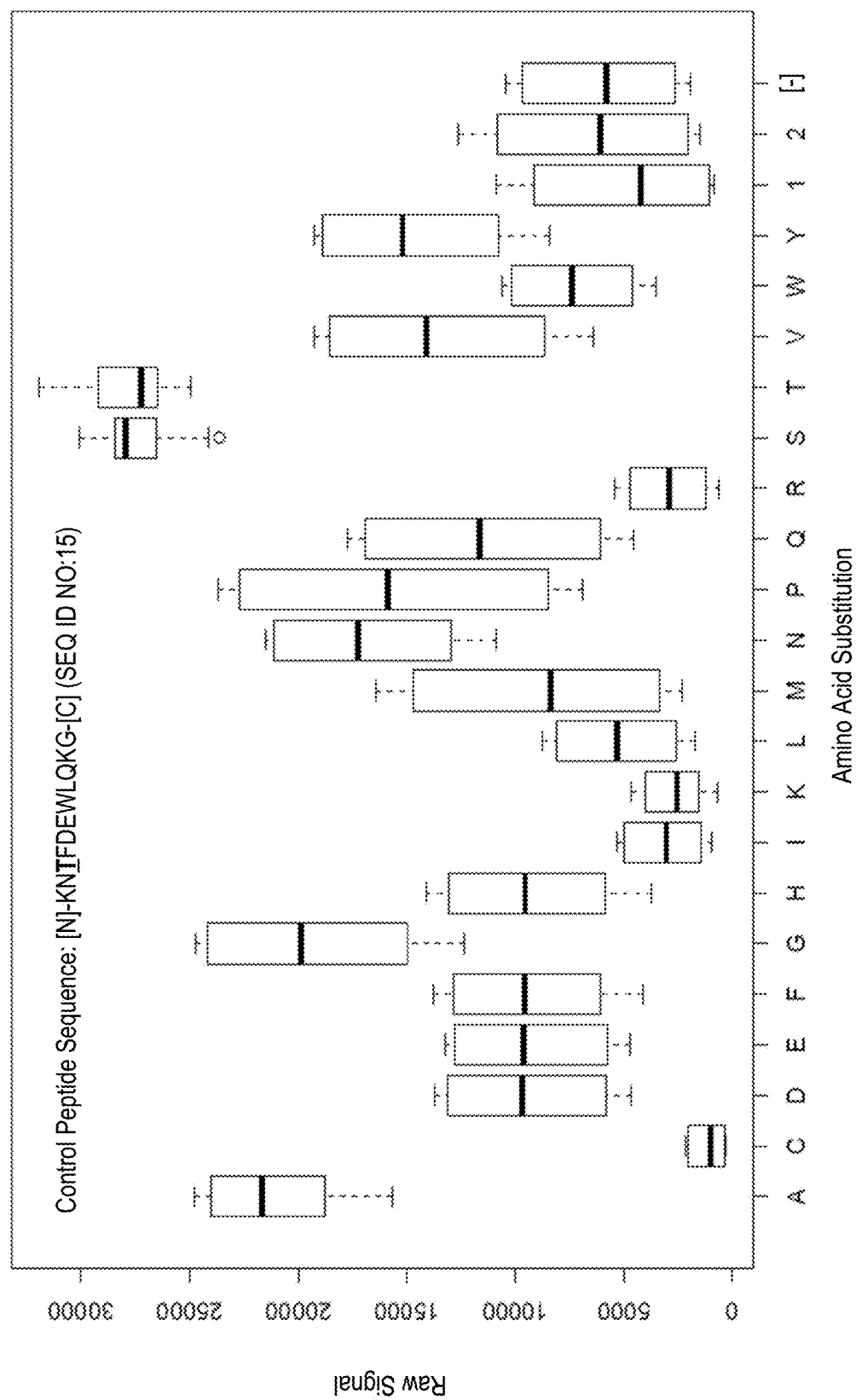
FIG. 21A is a profile of raw fluorescence signal for a control peptide having the sequence [N]-KNTFDEWLQKG-[C] (SEQ ID NO:15). Sequences comprising each possible amino acid substitution and deletion for the Thr at the 3$^{rd}$ position from the N-terminus were analyzed as indicated along the horizontal axis. The illustrated control peptide sequence can be used to assess incorporation of the amino acid Thr.
Figure 21B:
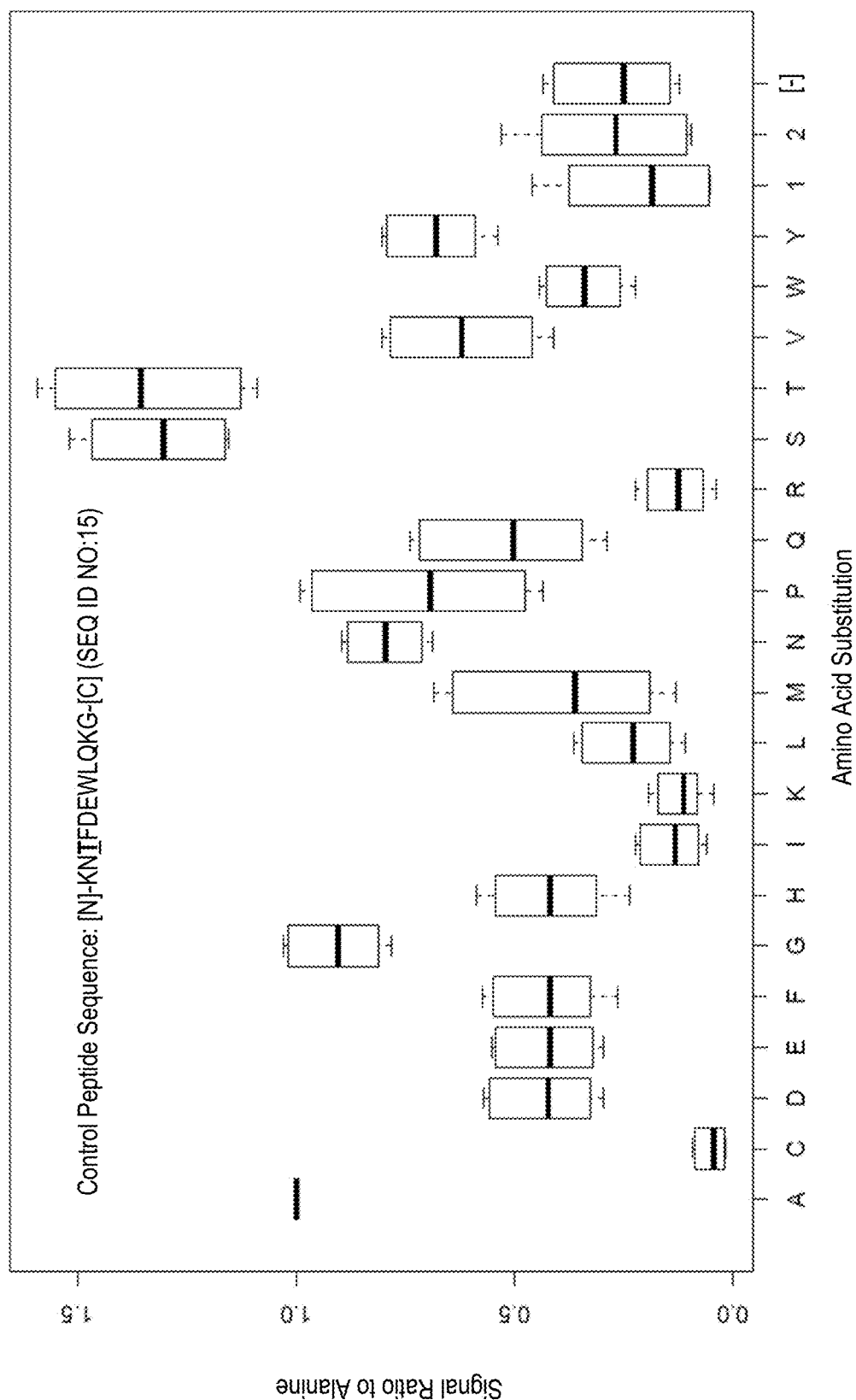
FIG. 21B is a profile of fluorescence signal ratio with respect to alanine for the control peptide of FIG. 21A. Sequences comprising each possible amino acid substitution and deletion for the Thr at the 3$^{rd}$ position from the N-terminus were analyzed as indicated along the horizontal axis.
Figure 22A:
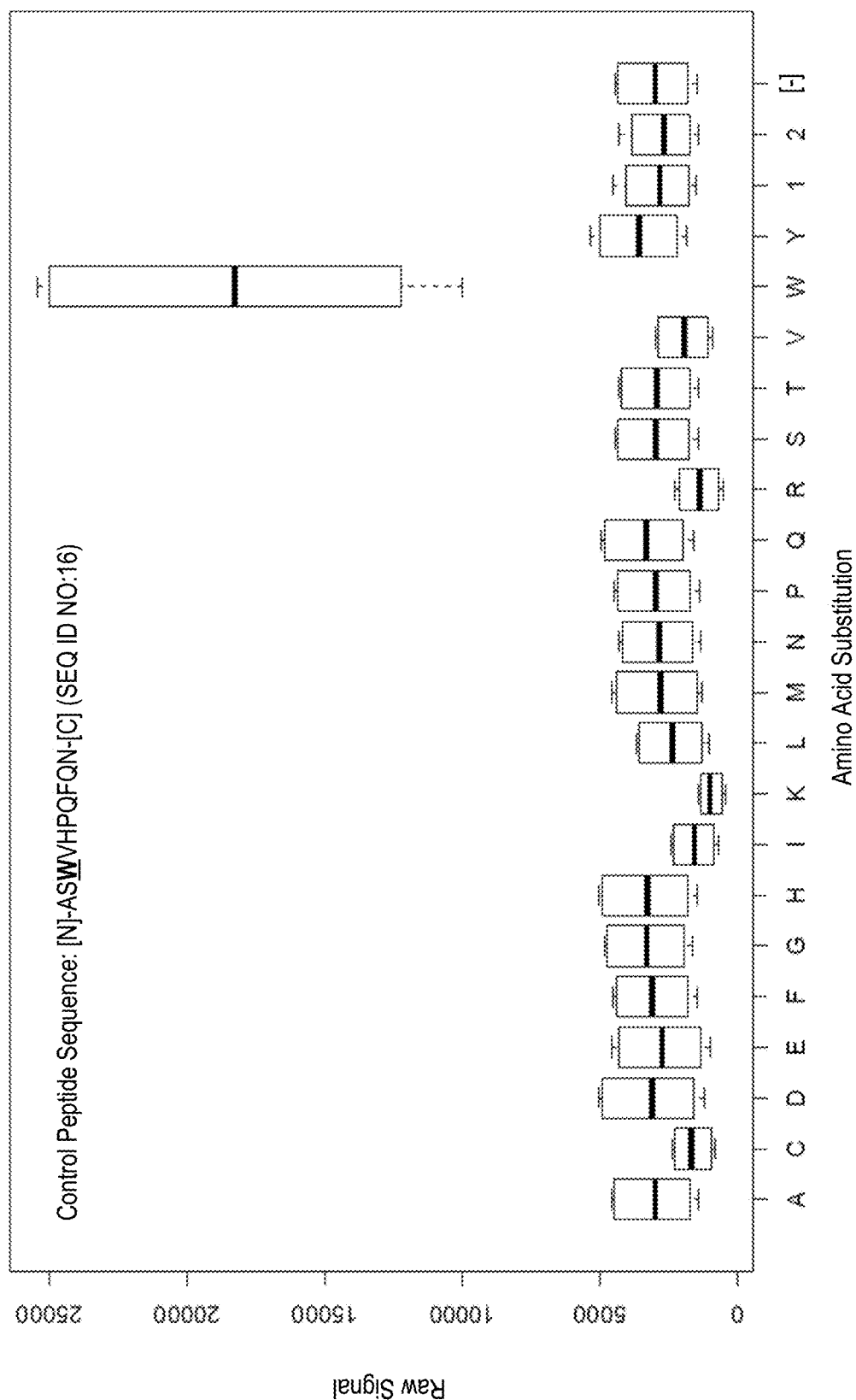
FIG. 22A is a profile of raw fluorescence signal for a control peptide having the sequence [N]-ASWVHPQFQN-[C] (SEQ ID NO:16). Sequences comprising each possible amino acid substitution and deletion for the Trp at the 3$^{rd}$ position from the N-terminus were analyzed as indicated along the horizontal axis. The illustrated control peptide sequence can be used to assess incorporation of the amino acid Trp.
Figure 22B:
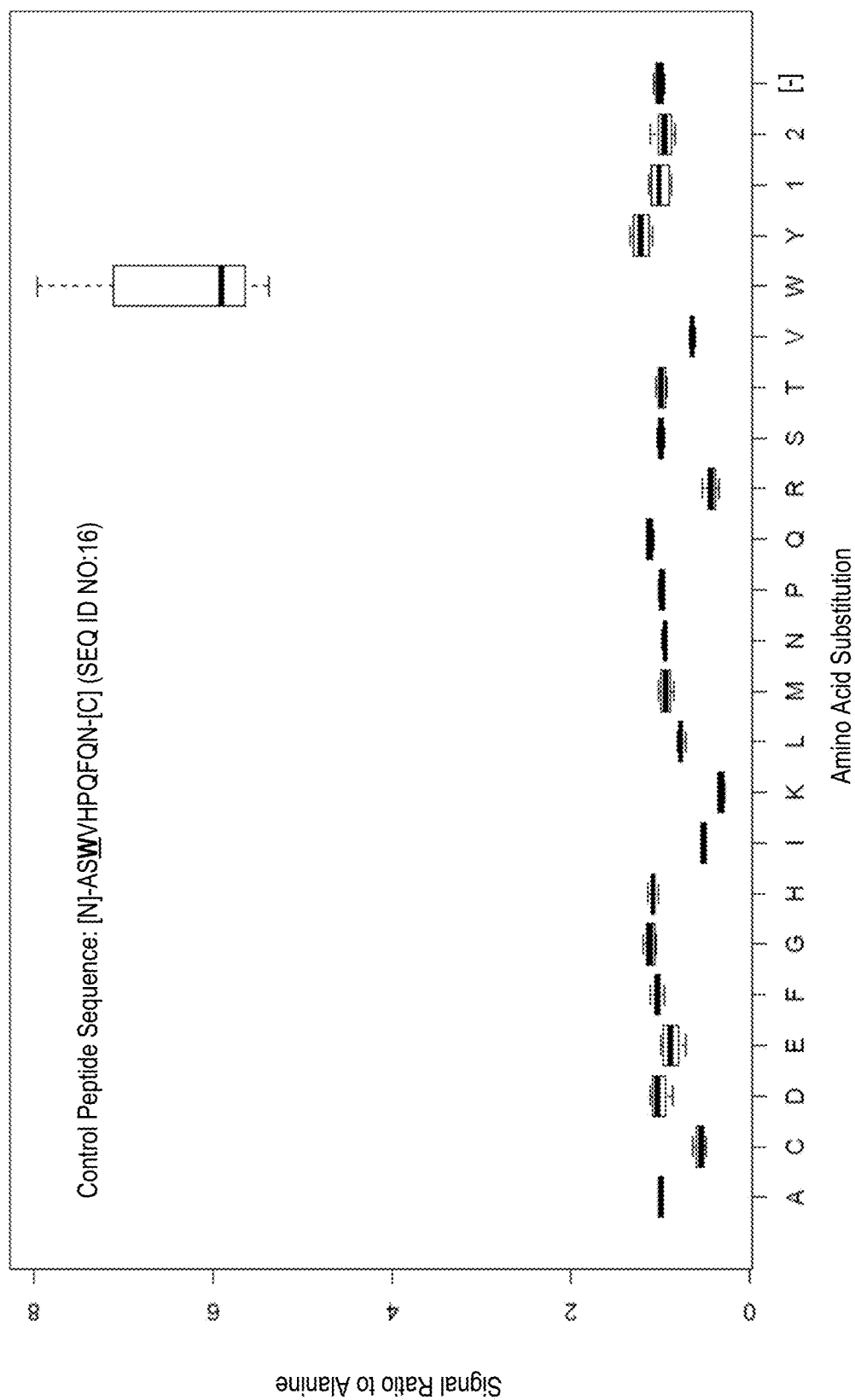
FIG. 22B is a profile of fluorescence signal ratio with respect to alanine for the control peptide of FIG. 22A. Sequences comprising each possible amino acid substitution and deletion for the Trp at the 3rd position from the N-terminus were analyzed as indicated along the horizontal axis.
Figure 23A:
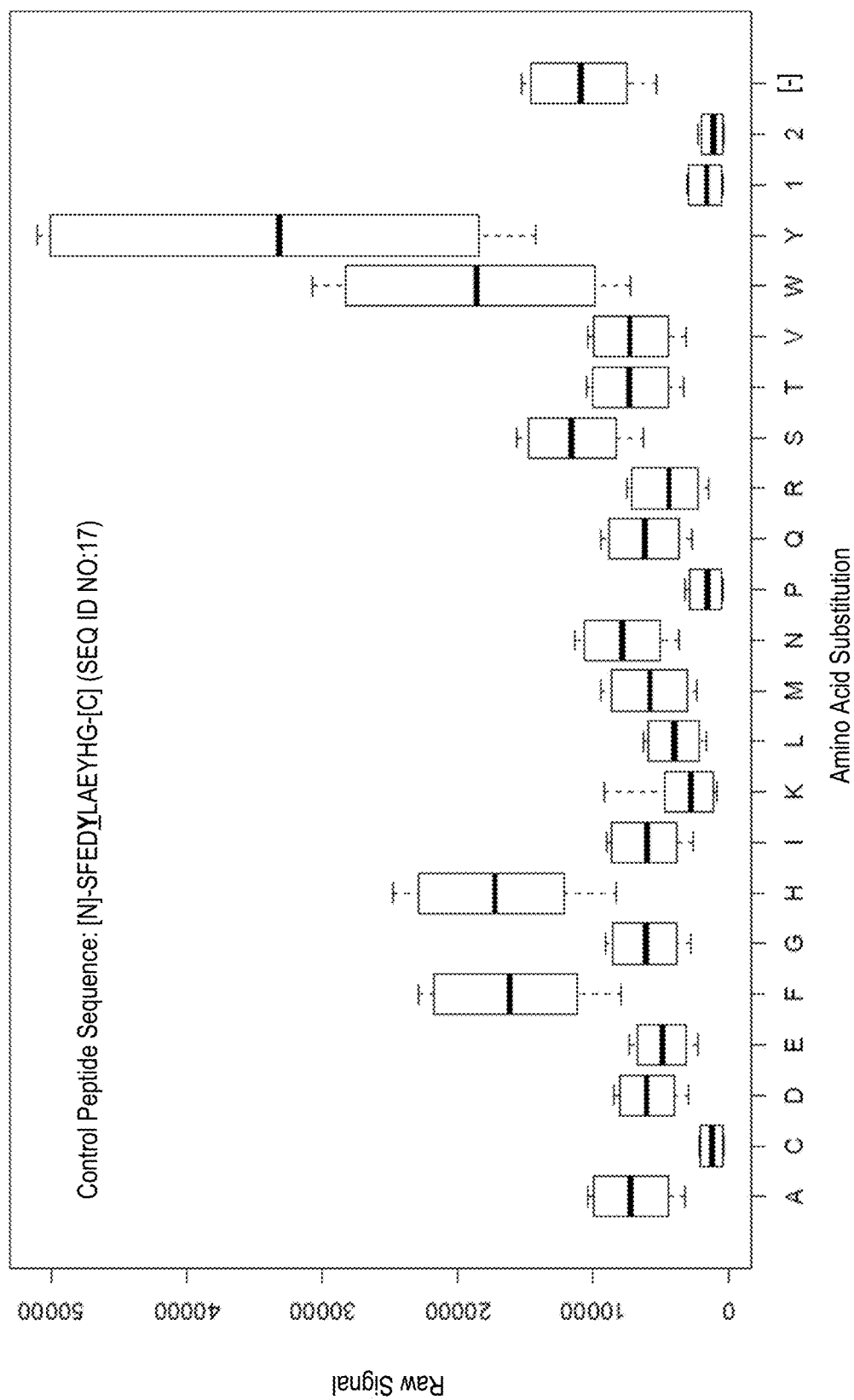
FIG. 23A is a profile of raw fluorescence signal for a control peptide having the sequence [N]-SFEDYLAEYHG-[C] (SEQ ID NO:17). Sequences comprising each possible amino acid substitution and deletion for the Tyr at the 5$^{th}$ position from the N-terminus were analyzed as indicated along the horizontal axis. The illustrated control peptide sequence can be used to assess incorporation of the amino acid Tyr.
Figure 23B:
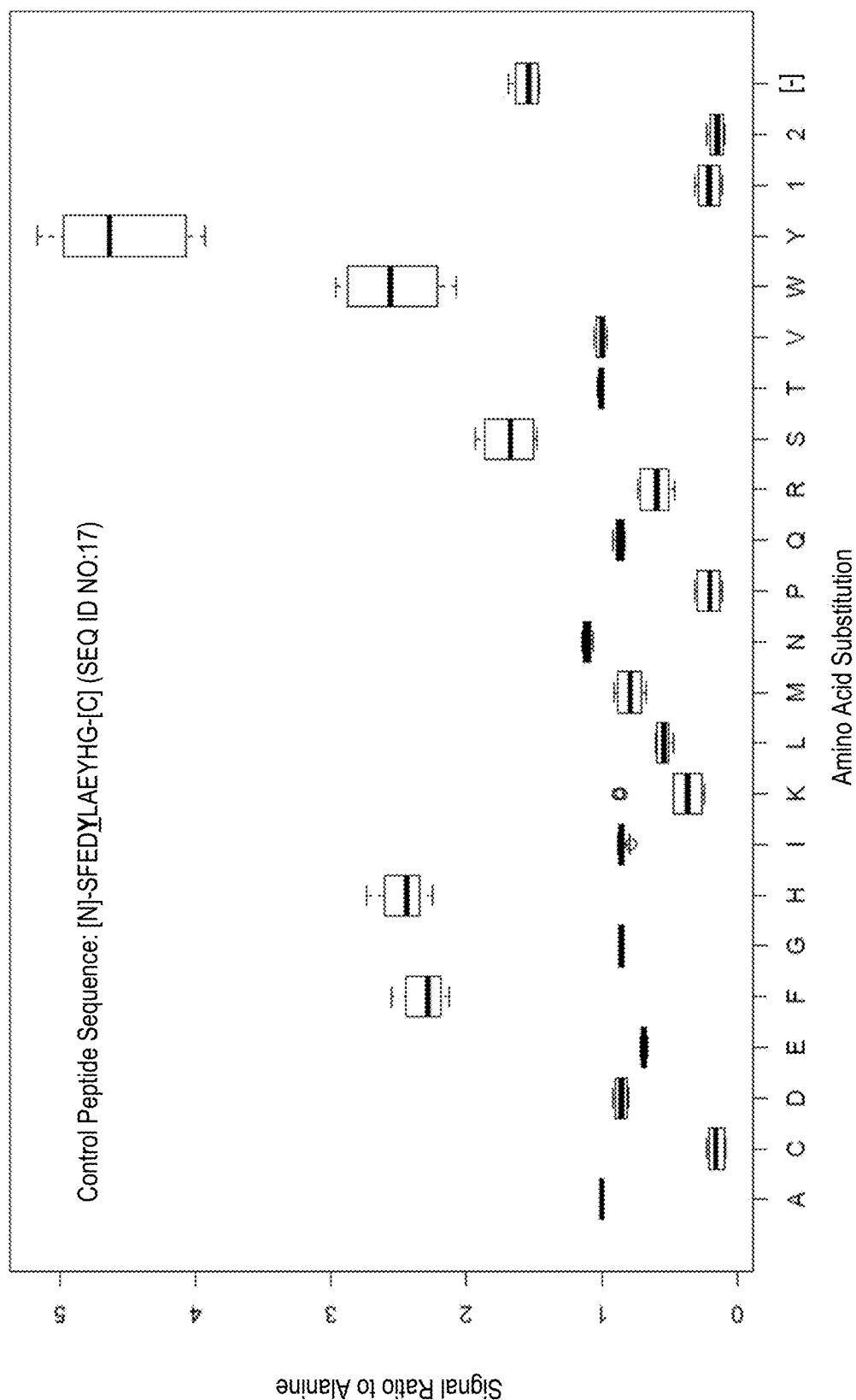
FIG. 23B is a profile of fluorescence signal ratio with respect to alanine for the control peptide of FIG. 23A. Sequences comprising each possible amino acid substitution and deletion for the Tyr at the 5$^{th}$ position from the N-terminus were analyzed as indicated along the horizontal axis.

Notably, the above example does not include features or synthesis procedures that correspond with the peptide synthesis conditions [1] and [2] illustrated in FIGS. 5-18 and FIGS. 20-23 (data for peptide synthesis conditions [1], [2] and [-] was not available for the control peptide RYHPQ (SEQ ID NO: 13) illustrated in FIGS. 19A and 19B). In one aspect, the synthesis conditions that result in the peptide data labeled [1] and [2] in, for example, FIGS. 7A and 7B can be useful for the initial characterization of a control peptide or binder sequence. However, for synthesis of peptide arrays where it is useful to prepare peptide features with high fidelity, it can be useful to avoid replicating synthesis conditions that can result in errors such as deletions. Accordingly, blocks of control peptides can be limited to the 21 unique peptide sequences excluding those sequences prepared under synthesis conditions [1] and [2] as described above. It will be appreciated, however, that a block of control peptides is not limited to the sequences described herein, and more or less than 17 control peptide sequences (and more or less than the 21 corresponding substitution or deletion sequences described) may be included in a given design for a peptide array.

Detection of Reagent Contamination

In another example according to the present disclosure, a control peptide sequence was used to identify the presence of a contaminant in the arginine synthesis reagent. Preliminarily, it was determined using the methods described herein that the control peptide sequence [N]-GYERPGWKLAG-[C] (SEQ ID NO:19) can be used to detect the presence (or absence) of acetic acid in one or more of the synthesis reagents used to synthesize a population of peptides including the control peptide sequence GYERPGWKLAG (SEQ ID NO:19). In the present example, peptide sequences were synthesized from the C-terminus to the N-terminus. Using this synthesis scheme, it was determined that the amino acid Pro in the $5^{th}$ position from the N-terminus of SEQ ID NO:19 is susceptible to acetylation in the presence of acetic acid. Without being limited by theory, it is hypothesized that as the direction of synthesis is from the C-terminus to the N-terminus, instead of addition of the amino acid Arg in the $4^{th}$ position from the N-terminus following addition of the amino acid Pro in the $5^{th}$ position, acetic acid was able to form an amino acid bond with the terminal proline. As acetic acid does not have a reactive amine group, the acetylated peptide sequence cannot be further extended through the formation of peptide bonds with additional amino acids, thereby resulting the in the truncated peptide sequence *PGWKLAG (SEQ ID NO:20), where the notation *P indicates that the N-terminal Pro is acetylated.

Figure 24:
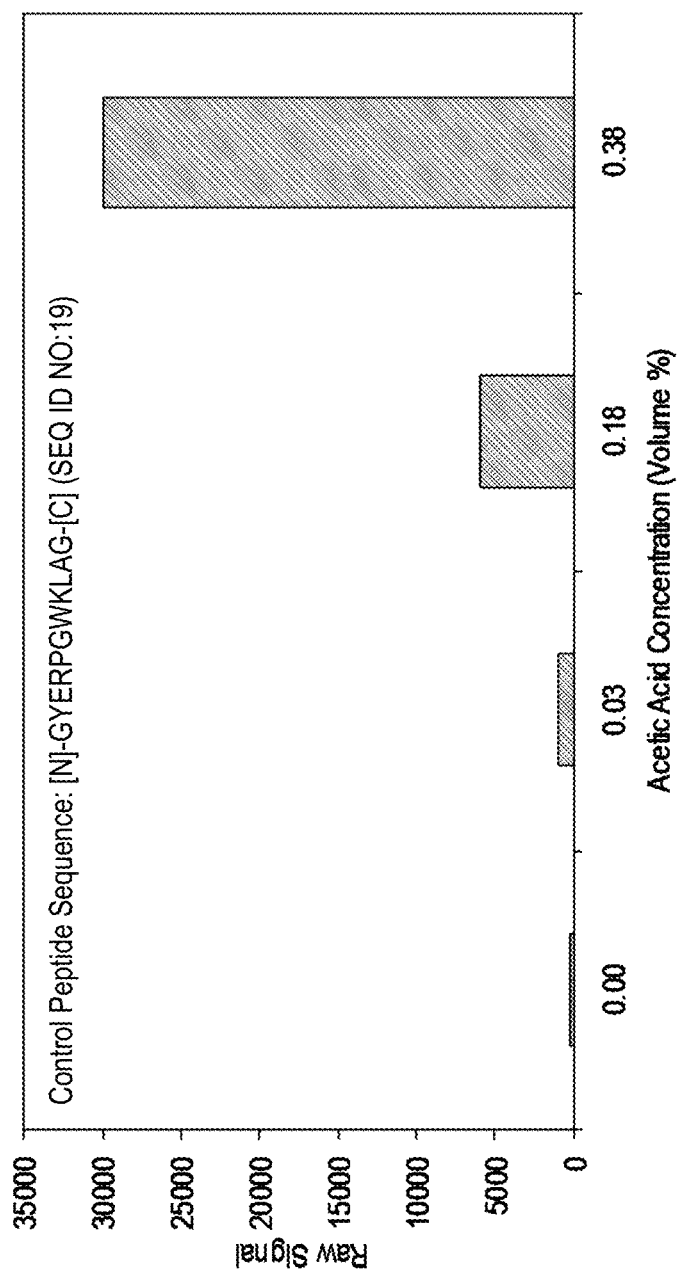
FIG. 24 is a profile of raw fluorescence signal for a control peptide having the sequence [N]-GYERPGWKLAG-[C] (SEQ ID NO:19). Data was collected for control peptides synthesized from arginine reagent solutions including different concentrations of the contaminant acetic acid ranging from 0.00 to 0.38 percent acetic acid by volume as indicated along the horizontal axis. The illustrated control peptide sequence can be used to assess the contamination of one or more amino acid synthesis reagents with acetic acid via the incorporation of the amino acid Arg at the 4$^{th}$ position from the N-terminus. Notably, the presence of the contaminant acetic acid can result in acetylation of the amino acid Pro at the 5$^{th}$ position from the N-terminus of SEQ ID NO:19, thereby resulting in the truncated peptide sequence *PGWKLAG (SEQ ID NO:20), where the notation *P indicates that the N-terminal Pro of SEQ ID NO:20 is acetylated.

Turning now to FIG. 24, the peptide *PGWKLAG (SEQ ID NO:20) was determined to exhibit intrinsic affinity towards an engineered form of the protein streptavidin, where the detection of the interaction of streptavidin with the truncated peptide *PGWKLAG (SEQ ID NO:20) was differentially detectable from the interaction of streptavidin with the full length peptide GYERPGWKLAG (SEQ ID NO:19). Moreover, the concentration of acetic acid in a synthesis reagent can be correlated with the signal output characteristic of the interaction of the streptavidin receptor with the control peptide feature (SEQ ID NO:19) or the truncated version thereof (SEQ ID NO:20). It will be further appreciated that the control peptide GYERPGWKLAG (SEQ ID NO:19) may alternatively include one or more different amino acids or other monomers in the $1^{st}$ through $4^{th}$ positions from the N-terminus, as these amino acids do not contribute to the binding of streptavidin to the acetylated control peptide of *PGWKLAG (SEQ ID NO:20). However, the amino acids at the N-terminus should be selected such that there is a detectable difference in the interaction of streptavidin with the alternative control peptide.

To illustrate the detection of varying concentrations of acetic acid in a peptide synthesis reagent, four different NPPOC-protected arginine reagent solutions were prepared with differing concentrations (volume %) of acetic acid. A first arginine solution included no detectable amount of acetic acid (i.e., about 0.00%), a second arginine solution included 0.03% acetic acid, a third arginine solution included a 0.18% acetic acid, and a fourth arginine solution included 0.38% acetic acid. Four different synthetic peptide populations were synthesized using one of the four arginine solutions, and the signal output characteristic of the interaction of the streptavidin receptor with each of the control peptide features (SEQ ID NO:19) or the truncated versions thereof (SEQ ID NO:20) was determined (FIG. 24). In one aspect, the arginine reagent solutions having a higher concentration of acetic acid exhibited a stronger signal output in comparison with the arginine reagent solutions having a lower concentration of acetic acid. In the present example, the raw signal output associated with the arginine reagent solution including 0.03% acetic acid was 1000 units, whereas the signal output associated with the arginine reagent solutions including 0.38% acetic acid was about 30,000 units. As indicated by this data, an approximately 13-fold increase in acetic acid concentration (i.e., from 0.03% to 0.38%) resulted in a 30-fold increase in raw signal. Accordingly, the control peptide GYERPGWKLAG (SEQ ID NO:19) can be included in peptide populations synthesized as described herein to detect acetic acid contamination in one or more synthesis reagents, including (but not limited to) arginine synthesis reagents.

In the context of a method of assessing the fidelity of a synthetic peptide population according to the present disclosure, contaminants such as acetic acid can have a detectable effect on the assessment of one or more control peptide features synthesized to have an amino acid sequence including a given amino acid or binder sequences. For example, during a step of detecting a signal output characteristic of an interaction of a receptor with a control peptide feature, the signal output can be indicative of the fidelity of incorporation of one or more amino acids into the control peptide at a defined position. If a contaminant affects the fidelity of incorporation of one or more amino acids into the control peptide, then this effect can be detected from the resulting signal output. In one aspect, the signal output can be indicative of the presence of the contaminant in at least one of the amino acid synthesis reagents used to synthesize one or more control peptides. In the case of the control peptide GYERPGWKLAG (SEQ ID NO:19), if the contaminant acetic acid is present at a concentration that is great enough to affect peptide synthesis, then the amino acid Arg may not be incorporated into the control peptide sequence GYERPGWKLAG (SEQ ID NO:19). Accordingly, the signal output (for control peptides synthesized in the presence of acetic acid) can be indicative of the fidelity of incorporation of at least the amino acid Arg into the control peptide at the defined position within SEQ ID NO:19 (i.e., the fourth position from the N-terminus). It will be appreciated, however, that for populations of peptides where it may be useful to incorporate acetic acid into one or more peptide sequences, the methods of the present disclosure can be used to detect the fidelity of incorporation of acetic acid into a control peptide sequence, in which case the acetic acid would not necessarily be classified as a contaminant.

In another aspect, yet other control peptide sequences can be identified as described for SEQ ID NO: 19 in order to detect other contaminants that may have an effect on the fidelity of synthesis of a population of synthetic peptides. For example, a control peptide can be prepared to detect contaminants that may cause an insertion, deletion, truncation, or augmentations of one or more synthetic peptides. Examples of insertions can include an insertion of one or monomers into a peptide sequence. Examples of deletions can include the absence of the inclusion of one or more monomers in a synthetic peptide sequence. Examples of truncations include the synthesis of a synthetic peptide having one or more terminal amino acids (or other monomers) missing due to non-incorporation of a monomer or cleavage of a terminal portion of the synthetic peptide. Examples of augmentations include the chemical or physical modifications of one or more monomers within a peptide sequence (e.g., conversion of arginine to citrulline or lysine to homocitrulline).

The schematic flow charts shown in the Figures are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the Figures are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention. Accordingly, the foregoing description is meant to be exemplary, and does not limit the scope of present inventive concepts.

Each reference identified in the present application is herein incorporated by reference in its entirety.

What is claimed is:

1. A method of assessing the fidelity of a synthetic peptide population, the method comprising:
interrogating a population of peptide features in the presence of a receptor having an affinity for a plurality of binder sequences, wherein a first amino acid is at a defined position within a first one of the binder sequences, and the population of peptide features includes a first control peptide feature synthesized to have an amino acid sequence including the first one of the binder sequences; and
detecting a signal output characteristic of an interaction of the receptor with the first control peptide feature, wherein the signal output is indicative of the fidelity of incorporation of the first amino acid into the first control peptide at the defined position within the first one of the binder sequences, and
wherein the population of peptide features is covalently bound to a solid surface in an array.

2. The method of claim 1, further comprising detecting a signal output characteristic of an interaction of the receptor with a second control peptide feature, wherein the signal output is indicative of the fidelity of incorporation of a second amino acid into the second control peptide at a defined position within a second one of the binder sequences, wherein the first amino acid is different from the second amino acid, and wherein the first one of the binder sequences is different from the second one of the binder sequences.

3. The method of claim 1, wherein the signal output is further indicative of the fidelity of incorporation of a second amino acid into the first control peptide at a defined position within the first one of the binder sequences different from that of the first amino acid within the first one of the binder sequences, wherein the first amino acid is different from the second amino acid.

4. The method of claim 1, wherein the receptor is streptavidin.

5. The method of claim 1, further comprising:
contacting the population of peptide features in the presence of the receptor with a fluorescent probe capable of binding to the receptor,
wherein the signal output is a fluorescence intensity obtained through fluorophore excitation-emission, the fluorescence intensity reflecting at least one of an abundance of a portion of the receptor associated with the first control peptide and a binding affinity of the receptor to the first control peptide.

6. The method of claim 1, wherein the peptide features are bound to the solid surface at a density of at least 100,000 features per square centimeter.

7. The method of claim 1, wherein the population of peptide features includes less than twenty unique control peptide features, each of the unique control peptide features synthesized to have an amino acid sequence including a selected one of the binder sequences, and
wherein the signal output is further characteristic of an interaction of the receptor with the less than twenty control peptide features, the signal output indicative of the fidelity of incorporation of each of the twenty natural amino acids into a selected one of the less than twenty unique control peptides at defined positions within the selected one of the binder sequences.

8. The method of claim 1, wherein the signal output is indicative of the presence of a contaminant in at least one of the amino acid synthesis reagents.

9. The method of claim 8, wherein the contaminant is acetic acid.

10. The method of claim 1, wherein the first amino acid is a D-amino acid.

11. The method of claim 1, wherein the first amino acid is an L-amino acid.

12. A method of assessing the fidelity of a synthetic peptide population, the method comprising:
synthesizing a population of peptide features on a solid surface, the population of peptide features comprising a plurality of sample peptide features and a plurality of control peptide features, the control peptide features including:
a first control peptide synthesized to have an amino acid sequence including a first one of a plurality of binder sequences having a first amino acid at a defined position within the first one of the binder sequences, and
a second control peptide synthesized to have an amino acid sequence including a second one of the plurality of binder sequences having a second amino acid at a defined position within the second one of the binder sequences;

contacting the population of peptide features on the solid surface with a receptor having an affinity for the plurality of binder sequences; and detecting an output characteristic of an interaction of the receptor with each of the first control peptide feature and the second control peptide feature, wherein the output is indicative of the fidelity of incorporation of (i) the first amino acid into the first control peptide at the defined position within the first one of the binder sequences, and (ii) the second amino acid into the second control peptide at the defined position within the second one of the binder sequences.

13. The method of claim 12, wherein the receptor is streptavidin.

14. The method of claim 12, further comprising:

contacting the population of peptide features in the presence of the receptor with a fluorescent probe capable of binding to the receptor, wherein the signal output is a fluorescence intensity obtained through fluorophore excitation-emission, the fluorescence intensity reflecting at least one of an abundance of a portion of the receptor associated with the first control peptide and a binding affinity of the receptor to the first control peptide.

15. The method of claim 12, wherein each of the sample peptide features has a defined sequence, and wherein the peptide features are bound to the solid surface at a density of at least 100,000 features per square centimeter.

16. The method of claim 12, wherein the population of peptide features includes less than twenty unique control peptide features, each of the unique control peptide features synthesized to have an amino acid sequence including a selected one of the binder sequences, and wherein the signal output is further characteristic of an interaction of the receptor with the less than twenty control peptide features, the signal output indicative of the fidelity of incorporation of each of the twenty natural amino acids into a selected one of the less than twenty unique control peptides at defined positions within the selected one of the binder sequences.

17. The method of claim 12, wherein the signal output is indicative of the presence of a contaminant in at least one of the amino acid synthesis reagents.

18. The method of claim 12, wherein the first amino acid is a D-amino acid.

19. The method of claim 12, wherein the first amino acid is an L-amino acid.

* * * * *

SEQUENCE LISTING

```
<160> NUMBER OF SEQ ID NOS: 54

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Glu Asp Tyr Leu Gly Glu Tyr His Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Trp Thr His Pro Met Phe Glu Gln Lys Gly
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Lys His Pro Gln Ala Gly Ser
1               5

<210> SEQ ID NO 4
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

Ala Ser Trp Cys His Pro Gln Gly Pro Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ser Tyr Asp His Pro Gln Gly Gly Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asn Ser Phe Asp Asp Trp Leu Gln Lys Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ser Trp Pro His Pro Gln Ser Gly Met
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ser Trp Ile His Pro Gln Phe Gln Gly
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Trp His Pro Gln Ser Gly Lys
1               5
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asn Ser Phe Asp Asp Trp Leu Asn Lys Gly
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Trp His Pro Gln Asn Ala Val
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Val His Pro Gln Phe Gln Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Tyr His Pro Gln
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ser Tyr Pro His Pro Gln Ser Gly Gln
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Asn Thr Phe Asp Glu Trp Leu Gln Lys Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ser Trp Val His Pro Gln Phe Gln Asn
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Phe Glu Asp Tyr Leu Ala Glu Tyr His Gly
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Ser His Pro Gln Phe Glu Lys
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Tyr Glu Arg Pro Gly Trp Lys Leu Ala Gly
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Gly Trp Lys Leu Ala Gly
1               5

<210> SEQ ID NO 21
<211> LENGTH: 6

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Met Met Met Met
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Met Met Met Met
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Met Met Met Met
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Met Met Met Met
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Met Met Met Met
```

```
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Ala Met Met Met
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Gln Met Met Met
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Pro Met Met Met
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Asn Met Met Met
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Ala Met Met Met
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 32

Pro Phe Met Met Met
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Val Met Met Met
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Glu Met Met Met
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Ala Met Met Met
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Phe Met Met Met
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Val Met Met Met
1               5

<210> SEQ ID NO 38

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Glu Met Met Met
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ala Met Met Met
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Phe Met Met Met
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Val Met Met Met
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Glu Met Met Met
1               5

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

```
Met Met Met Met
1
```

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 44

```
Xaa Met Met Met Met Met
1               5
```

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 45

```
Met Xaa Met Met Met Met
1               5
```

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 46

```
Met Met Xaa Met Met Met
1               5
```

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 47

```
Met Met Met Xaa Met Met
1               5
```

<210> SEQ ID NO 48
<211> LENGTH: 6
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 48

Met Met Met Met Xaa Met
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 49

Met Met Met Met Met Xaa
1               5

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Glu Asp Tyr Leu Gly Glu Tyr Ala Gly
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Phe Glu Asp Tyr Leu Gly Glu Tyr Cys Gly
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Phe Glu Asp Tyr Leu Gly Glu Tyr Asp Gly
1               5                   10

<210> SEQ ID NO 53
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 53

Gly Phe Glu Asp Tyr Leu Gly Glu Tyr Tyr Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Glu Asp Tyr Leu Gly Glu Tyr Gly
1               5                   10
```